United States Patent
Neumaier et al.

(10) Patent No.: US 10,112,974 B2
(45) Date of Patent: Oct. 30, 2018

(54) METHOD FOR THE PRODUCTION OF 18F-LABELED ACTIVE ESTERS AND THEIR APPLICATION EXEMPLIFIED BY THE PREPARATION OF A PSMA-SPECIFIC PET-TRACER

(71) Applicants: Max-Planck-Gesellschaft zur Foerderung der Wissenschaften e.V., Munich (DE); Universitat Zu Koln, Cologne (DE)

(72) Inventors: Bernd Neumaier, Hurth (DE); Boris Zlatopolskiy, Cologne (DE); Raphael Richarz, Leverkusen (DE); Phillip Krapf, Much (DE)

(73) Assignees: Max-Planck-Gesellschaft zur Foerderung der Wissenschaften e.V., Munich (DE); Universitat Zu Koln, Cologne (DE)

( * ) Notice: Subject to any disclaimer, the term of this patent is extended or adjusted under 35 U.S.C. 154(b) by 0 days.

(21) Appl. No.: 15/506,351

(22) PCT Filed: Aug. 24, 2015

(86) PCT No.: PCT/EP2015/069356
§ 371 (c)(1),
(2) Date: Feb. 24, 2017

(87) PCT Pub. No.: WO2016/030329
PCT Pub. Date: Mar. 3, 2016

(65) Prior Publication Data
US 2017/0267717 A1 Sep. 21, 2017

(30) Foreign Application Priority Data

Aug. 24, 2014 (EP) .................................. 14182053
Sep. 4, 2014 (EP) .................................. 14183635

(51) Int. Cl.
| | | |
|---|---|---|
| C07D 213/82 | (2006.01) | |
| C07K 5/062 | (2006.01) | |
| C07C 275/16 | (2006.01) | |
| C07K 1/13 | (2006.01) | |
| C07K 5/065 | (2006.01) | |
| C07B 59/00 | (2006.01) | |
| C07D 237/24 | (2006.01) | |
| C07D 241/24 | (2006.01) | |

(52) U.S. Cl.
CPC ........ *C07K 5/06026* (2013.01); *C07B 59/002* (2013.01); *C07C 275/16* (2013.01); *C07D 213/82* (2013.01); *C07D 237/24* (2013.01); *C07D 241/24* (2013.01); *C07K 1/13* (2013.01); *C07K 5/06078* (2013.01); *C07B 2200/05* (2013.01)

(58) Field of Classification Search
CPC ..................................................... C07B 59/00
See application file for complete search history.

(56) References Cited

U.S. PATENT DOCUMENTS

| | | |
|---|---|---|
| 8,487,129 B2 | 7/2013 | Babich et al. |
| 8,491,790 B2 | 7/2013 | Lemaire et al. |
| 8,778,305 B2 | 7/2014 | Pomper et al. |
| 9,044,468 B2 | 6/2015 | Pomper et al. |
| 9,056,841 B2 | 6/2015 | Pomper et al. |
| 9,226,981 B2 | 1/2016 | Pomper et al. |
| 9,309,193 B2 | 4/2016 | Babich et al. |
| 2008/0193381 A1 | 8/2008 | Babich et al. |
| 2010/0196254 A1 | 8/2010 | Lemaire et al. |
| 2011/0064657 A1 | 3/2011 | Pomper et al. |
| 2011/0142760 A1 | 6/2011 | Pomper et al. |
| 2012/0009121 A1 | 1/2012 | Pomper et al. |
| 2012/0208988 A1 | 8/2012 | Babich et al. |
| 2012/0269726 A1 | 10/2012 | Babich et al. |

(Continued)

FOREIGN PATENT DOCUMENTS

| | | | |
|---|---|---|---|
| WO | 2008/058192 A2 | 5/2008 | |
| WO | WO2008/058192 | * 5/2008 | ............... C09C 1/00 |

(Continued)

OTHER PUBLICATIONS

International Search Report dated Dec. 2, 2015 issued in corresponding PCT/EP2015/069356 application (6 pages).
Written Opinion of the International Searching Authority dated Dec. 2, 2015 issued in corresponding PCT/EP2015/069356 application (11 pages).
H.M. Shallal et al., "Heterobivalent Agents Targeting PSMA and Integrin-[alpha]v[beta]3", Bioconjugate Chemistry, vol. 25, No. 2 (2014) pp. 393-405.
R. Richarz et al., "Neither Azeotropic Drying, Nor Base Nor Other Additives: A Minimalist Approach to 18F-Labeling", Organic & Biomolecular Chemistry, vol. 12, No. 40 (2014) pp. 8094-8099.

*Primary Examiner* — Paul V Ward
(74) *Attorney, Agent, or Firm* — Millen White Zelano and Branigan, PC

(57) ABSTRACT

Novel efficient, time-saving and reliable radiofluorination procedures for the production of $^{18}$F-labelled active esters via nucleophilic substitution of the corresponding onium precursors with $^{18}$F$^-$ are described. The active ester including [$^{18}$F]F-Py-TFP and [$^{18}$F]TFB produced by one of these methods was used to prepare PSMA-specific PET tracers such as [$^{18}$F]DCFPyL. The key advantages of these inventive methods are efficiency, short time of preparation and excellent amenability to automation. A pharmaceutical composition containing at least one PSMA-specific PET tracers prepared by the inventive method is useful for positron emission tomography (PET) imaging, especially imaging prostate tumor.

35 Claims, 4 Drawing Sheets

(56) References Cited

U.S. PATENT DOCUMENTS

| | | |
|---|---|---|
| 2014/0369931 A1 | 12/2014 | Pomper et al. |
| 2015/0104387 A1 | 4/2015 | Pomper et al. |
| 2015/0246144 A1 | 9/2015 | Pomper et al. |
| 2016/0114060 A1 | 4/2016 | Pomper et al. |
| 2016/0279235 A1 | 9/2016 | Babich et al. |
| 2017/0044098 A1 | 2/2017 | Babich et al. |

FOREIGN PATENT DOCUMENTS

| | | | |
|---|---|---|---|
| WO | 2009/002529 A2 | 12/2008 | |
| WO | 2009/003251 A1 | 1/2009 | |
| WO | 2010/014933 A2 | 2/2010 | |
| WO | WO2010/014933 * | 2/2010 | ............... C09C 1/00 |
| WO | 2010/108125 A2 | 9/2010 | |

* cited by examiner

[¹⁸F]DCFPyL ([¹⁸F]1-10)

[⁶⁸Ga]HBED-CC transverse   horizontal   sagittal

METHOD FOR THE PRODUCTION OF 18F-LABELED ACTIVE ESTERS AND THEIR APPLICATION EXEMPLIFIED BY THE PREPARATION OF A PSMA-SPECIFIC PET-TRACER

Novel efficient, time-saving and reliable radiofluorination procedures for the production of $^{18}$F-labeled active esters via nucleophilic substitution of the corresponding onium precursors with $^{18}$F$^-$ are described. The active ester including [$^{18}$F]F-Py-TFP 3c and [$^{18}$F]TFB 3a produced by one of these methods was used to prepare PSMA-specific PET tracers such as [$^{18}$F]DCFPyL 1-10. The key advantages of these inventive methods are efficiency, short time of preparation and excellent amenability to automation. A pharmaceutical composition containing at least one PSMA-specific PET tracers prepared by the inventive method is useful for positron emission tomography (PET) imaging, especially imaging prostate tumor.

BACKGROUND OF THE INVENTION

Amongst imaging technologies PET (Positron Emission Tomography) plays a very important role due to its outstanding potential to visualize physiological processes at the molecular level in real time. PET is therefore essential in clinical diagnostics and has gained major significance in drug development. Beside technical improvements, PET benefits mainly from innovations in the field of tracer development, comprising both progress in labelling strategies and an intelligent design of selective molecular probes with the capability to visualize molecular targets involved in physiological and pathophysiological processes. A prerequisite for the latter is a deepened insight into the biology underlying normal or diseased states at the molecular level. Molecular probes for PET-imaging must be labeled with suitable γ$^+$-emitting nuclides. Among the spectrum of easy available radionuclides $^{18}$F-fluorine is still the nuclide with the highest impact in PET research. This is mainly based on the excellent nuclear properties of $^{18}$F in comparison to other cyclotron-produced nuclides. Decay characteristics of $^{18}$F [E(β$^+$)=630 keV, abundance: 97%; t$_{1/2}$=109.8 min] make it an ideal PET-isotope with respect to half-life and resolution.

Numerous methods for $^{18}$F labelling have been developed to prepare tailor-made probes which allow visualizing biochemical processes of interest. The vast majority of $^{18}$F-labelling techniques are based on aliphatic and aromatic nucleophilic substitution reaction with $^{18}$F$^-$. Sometimes, $^{18}$F-labeled small molecules can be obtained in one step from the proper labelling precursor. However, protecting groups are often required for functionalities in the molecule which may interfere with the radiofluorination reaction.

Relatively harsh reaction conditions for radiofluorination are normally incompatible with sensitive molecules including proteins and the majority of peptides. In this case indirect radiofluorination via $^{18}$F-labeled prosthetic groups is the only alternative. Radiofluorinated active esters—amine-reactive prosthetic groups—are among the most widely used radiolabeled building blocks.

In all previously described radiosyntheses of $^{18}$F-labelled active esters [$^{18}$F]fluoride should be preliminary taken up in an aqueous or aqueous/organic solution of moderately strong or weak bases to give the corresponding [$^{18}$F]fluoride salt. Usually K, Cs or tetraalkylammonium carbonates/bicarbonates are used. In case of K salts aminopolyethers are routinely added to enhance the nucleophilicity of $^{18}$F$^-$. In case of Cs and tetraalkylammonium salts enhancement of $^{18}$F$^-$ nucleophilicity is achieved as a result of charge separation based on the great difference between the sizes of counter ions. However, active esters are limitedly stable under basic conditions. Consequently, a majority of them including N-succinimidyl 4-[$^{18}$F]fluorobenzoate ([$^{18}$F]SFB) could not be usually prepared in one step in acceptable RCYs. Only few of them such as 6-[$^{18}$F]fluoronicotinic acid 2,3,5,6-tetrafluorophenyl ester ([$^{18}$F]F-Py-TFP) could be prepared via direct radiofluorination. Furthermore, water substantially diminishes nucleophilicity of $^{18}$F$^-$ due to tenacious hydration. Consequently, water removal using repetitive azeotropic drying with acetonitrile is usually mandatory.

[$^{18}$F]SFB is most commonly used for the preparation of radiolabelled biomolecules. However, its broad application is hampered by tedious preparation procedures. Some of them are summarized in Table 1.

TABLE 1

Selected methods for the preparation of [$^{18}$F]SFB.

| Steps | Precursor | | R | Process | Time [min] | RCY [%] | Ref |
|---|---|---|---|---|---|---|---|
| 3 | 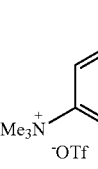 | H | | 3-step, 3-pot, 3 separations (SPE & HPLC) | 80 | 30-35 | 1 |
| | | OEt | | 3-step, 2-pot, 2 separations (SPE) | 78 | 41-51 | 2 |
| | | | | 3-step, 1-pot, 1 separation (SPE) | 60 | 44 | 3 |
| | | OtBu | | 3-step, 2-pot, 2 separations (SPE) | 68 | 34-38 | 4 |
| 2 | 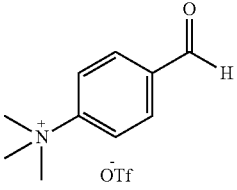 | — | | 2-step, 2-pot, 2 separations (SPEs or SPE & HPLC) | 100 (for 2 SPE); 160 (for SPE & HPLC) | 30-40 | 5 |

G. Vaidyanathan, M. R. Zalutsky, *Nucl. Med. Biol.* 1992, 19, 275-281.; H.-J. Wester, K. Hamacher, G. Stocklin, *Nucl. Med. Biol.* 1996, 23, 365-372.; S. Guhlke, H. H. Coenen, G. Stöcklin, *Appl. Radiat Isot.* 1994, 45, 715-725.; E. D. Hostetler, W. B. Edwards, C. J. Anderson, M. J. Welch, *J. Label. Compd. Radiopharm.* 1999, 42, S720-S722.; M. Glaser, E. Årstad, S. K. Luthra, E. G. Robins, *J. Label Compd. Radiopharm.* 2009, 52, 327-330.

All described [18F]SFB radiosyntheses consist of 2-3 reactions and multiple operation steps. For example, according to Wester et al. (*Nucl. Med. Biol.* 1996, 23, 365-372) [18F]SFB was prepared via ethyl 4-[18F]fluorobenzoate (Scheme 1).

dried by using MeCN. To the residue a solution of TSTA (N,N,N',N'-tetramethyl(succinimido)uronium tetrafluoroborate) in MeCN was added and the mixture was heated at 90° C. for 2 min. [18F]SFB was finally isolated by SPE using a polystyrene resin.

Scheme 1: Radiosynthesis of [18F]SFB according to Wester et al.

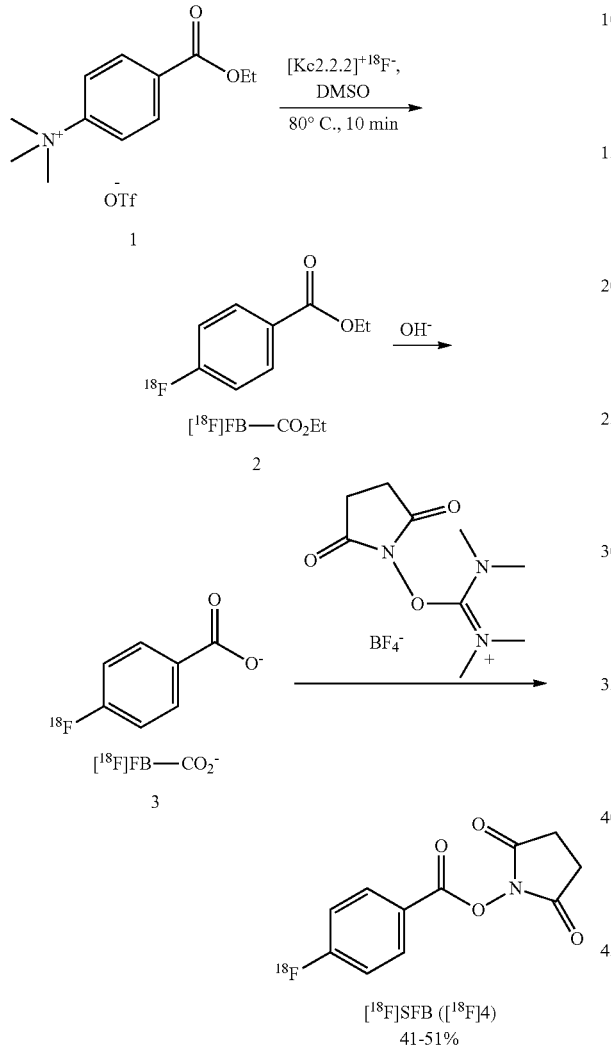

Scheme 2: Radiosynthesis of [18F]SFB according to Glaser et al.

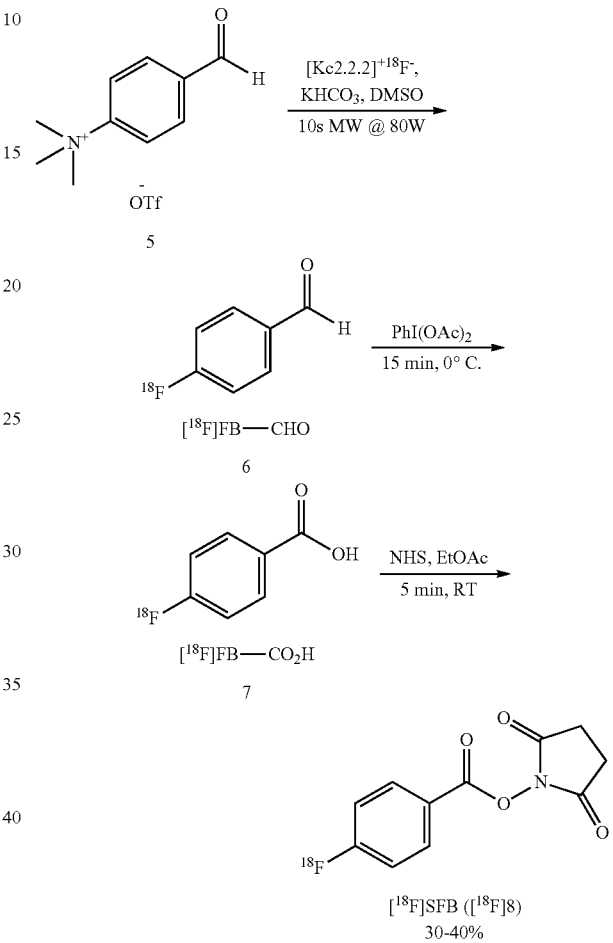

Accordingly, 18F⁻ target water was added to a solution of $K_2CO_3/K_2C_2O_4$ and K2.2.2 (Kryptofix 222) in aqueous MeCN. The solvent was removed under reduced pressure in a flow of nitrogen and the residue was two times azeotropically dried by using MeCN. The residue was taken up in a solution of N,N,N-trimethyl-4-carbomethoxyanilinium triflate in DMSO. The reaction mixture was heated at 90-110° C. for 6 min. Thereafter, 1 M NaOH was added and the mixture was heated at the same temperature for a further 10 min.

Afterwards, it was acidified with 1 M HCl and diluted with water. The intermediate 4-[18F]fluorobenzoic acid was purified by SPE (solid phase extraction) using polystyrene and cation exchange cartridges. Tetramethylammonium hydroxide was then added to the methanolic solution of the intermediate and MeOH was removed under reduced pressure at 90° C. The residue was two times azeotropically Glaser et al. (*J. Label Compd. Radiopharm.* 2009, 52, 327-330) produced [18F]SFB via 4-[18F]fluorobenzaldehyde ([18F]FB-CHO) (Scheme 2). To a solution of $K_2CO_3$ and K2.2.2 in aqueous MeCN irradiated target water was added. The solvent was removed under reduced pressure in a flow of nitrogen and the residue was three times azeotropically dried by using MeCN. The residue was taken up in a solution of N,N,N-trimethyl-4-formylanilinium triflate in DMSO or DMF. The reaction mixture was briefly heated using microwave energy. The mixture was transferred on a silica gel cartridge and most of the solvent was removed by flushing with nitrogen. The intermediate [18F]FB-CHO was fractionally eluted using anhydrous ethyl acetate. One fraction (0.5 mL) was cooled to 0 C. Iodobenzene diacetate (BAIB) was added, the mixture was stirred at 0° C. for 15 min and allowed to reach ambient temperature for 5 min. It was decanted and the supernatant was purified via SPE or HPLC to afford [18F]SFB in EtOAc/hexane solution. Before [18F]SFB can be used for labelling of EtOAc/hexane-insoluble proteins or peptides, it should be taken up in an water-miscible solvent.

Additionally, the high hydrophobicity of the fluorobenzoyl group limits its application for the labelling of small molecules and shorter peptides. Therefore, several alternatives to SFB were proposed. The most interesting one is 6-[$^{18}$F]fluoronicotinic acid 2,3,5,6-tetrafluorophenyl ester ([$^{18}$F]F-Py-TFP) first published by Olberg et al. (*J. Med. Chem.* 2010, 53, 1732-1740). [$^{18}$F]F-Py-TFP could be prepared using a one-step procedure in moderate radiochemical yield (RCYs) of 40-50% (Scheme 3). Additionally, [$^{18}$F]F-Py-TFP is more hydrolytically stable compared to [$^{18}$F]SFB. Moreover, it provides more hydrophilic radiolabelled conjugates.

Scheme 3: Preparation of [$^{18}$F]F—Py—TFP according to Olberg et al.

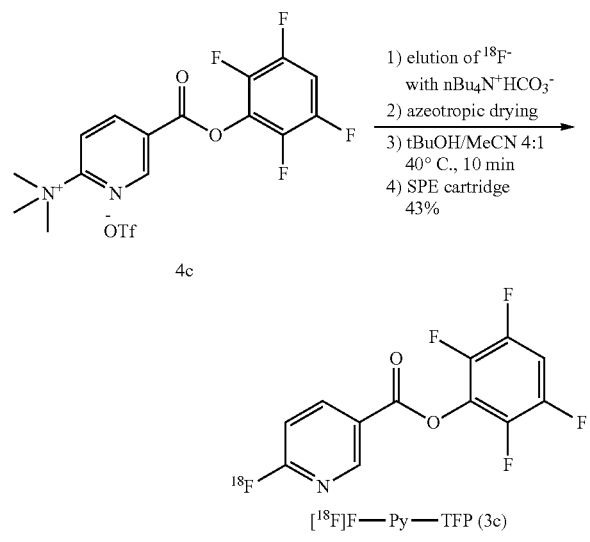

According to Olberg et al. $^{18}$F$^-$ was fixed on an anion exchange resin. Thereafter, it was eluted with a solution of tetrabutylammonium bicarbonate in 50% MeCN. The solvent was removed under reduced pressure in a flow of nitrogen and the residue was two times azeotropically dried by using MeCN. After that, a solution of the respective precursor, N,N,N-trimethyl-5-[(2,3,5,6-tetrafluorophenoxy)-carbonyl]pyridine-2-aminium trifluoromethanesulfonate 4c, in MeCN/tBuOH 2:8 was added to the [$^{18}$F]TBAF and the reaction mixture was heated at 40 C for 10 min to give [$^{18}$F]F-Py-TFP 3c in 50% RCY. [$^{18}$F]F-Py-TFP was purified by SPE on a mixed mode reversed phase cation exchange resin. This synthetic method includes azeotropic drying steps. These preparation steps cause longer synthesis time and this results in lower RCYs of [$^{18}$F]F-Py-TFP 3c. Furthermore, formation of [$^{18}$F]F-Py-TFP is accompanied by the concurrent formation of significant amounts of 2,3,5,6-tetrafluorophenyl 6-(2,3,5,6-tetrafluorophenoxy)nicotinate which should be completely separated from the radiolabelled active ester best by HPLC.

In recent years imaging of prostate carcinoma (PCa) with PET isotope labelled PSMA ligands has become of considerable importance in clinical diagnosis. This can be mainly attributed to the high expression of the extracellular localized prostate specific membrane antigen (PSMA) in PCa. Ligands bearing the syL-C(O)-Glu-binding motif exhibit high binding affinity to PSMA. Pomper et al. (WO2010/01493; *Clin. Cancer Res.* 2011, 17, 7645-7653) exploited this lead structure to prepare 2-(3-{1-carboxy-5-[(6-[$^{18}$F]fluoro-pyridine-3-carbonyl)-amino]-pentyl}-ureido)-pentanedioic acid ([$^{18}$F]DCFPyL) (Scheme 4). This PET tracer provided a clear delineation of PSMA positive prostate tumor xenografts in mice with an excellent tumor to background ratio.

Scheme 4: Preparation of [$^{18}$F]DCFPyL according to Pomper et al.

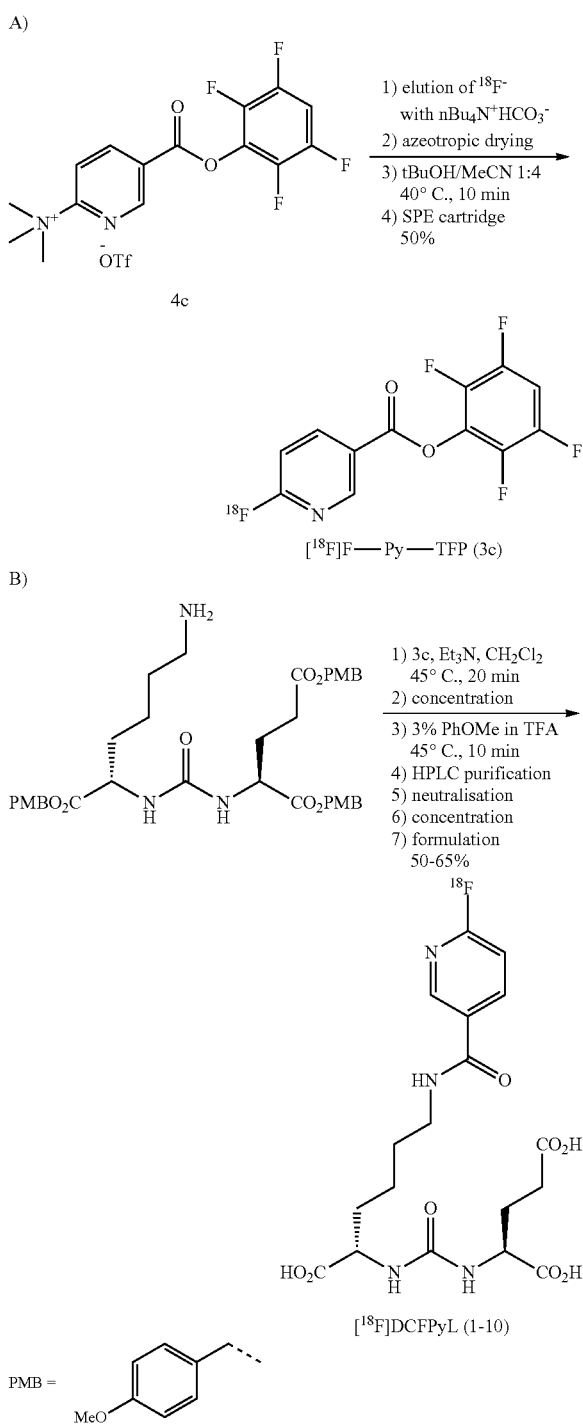

Pomper et al. prepared [$^{18}$F]DCFPyL in three steps. First, [$^{18}$F]F-Py-TFP was synthesized as reported by Olberg et al.

(*J. Med. Chem.* 2010, 53, 1732-1740). [$^{18}$F]F-Py-TFP was eluted from the resin with dichloromethane into a vial containing 1,5-bis(4-methoxyphenyl)methyl 2-[({6-amino-1-[(4-methoxyphenyl)methoxy]-1-oxohexan-2-yl}carbamoyl)amino]pentanedioate [H-DUPA(OPMB)$_3$] and triethylamine 11 (Scheme 4). The reaction mixture was heated at 45° C. for 20 min. Thereafter the solvent was removed with a stream of nitrogen. Anisole in TFA was added, the reaction mixture was heated at 45° C. for further 10 min and the desired product was isolated via HPLC using 10% MeCN (0.1% TFA). The fraction containing [$^{18}$F] DCFPyL was neutralized with sodium bicarbonate, concentrated to dryness under reduced pressure and reconstituted in PBS to give [$^{18}$F]DCFPyL in RCYs of 50-65%. The disadvantages of the above-mentioned method are:
- Application of dichloromethane as a solvent
- Two evaporation steps
- PMB deprotection step using toxic TFA (Scheme 4B step 3)
- Neutralisation step
- Formulation step It is the objective of the present invention to provide an inventive method for preparation of PSMA selective PET tracer for prostate tumor imaging comprising a simplified procedure for the fast and high yielding preparation of $^{18}$F-labelled active esters and a pharmaceutical composition containing at least one compound (I) prepared by the inventive method for use in positron emission tomography (PET) imaging, especially imaging prostate tumor.

The objective of the present invention is solved by the teaching of the independent claims. Further advantageous features, aspects and details of the invention are evident from the dependent claims, the description, the figures, and the examples of the present application.

DESCRIPTION OF THE INVENTION

Accordingly the present invention relates to a method for preparing a compound of the general formula (I):

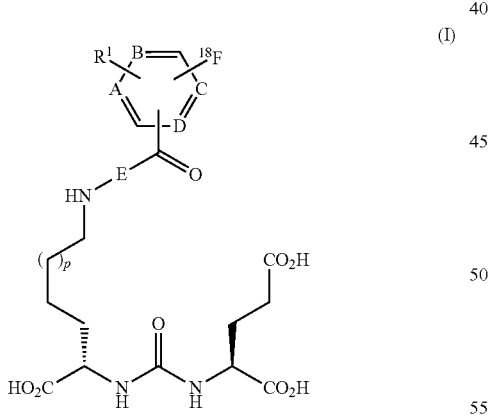

(I)

wherein A, B, C, and D represent independently of each other C—H, C—F or N; and not more than two of A, B, C, and D represent N;
E represents a covalent bond or

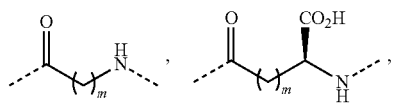

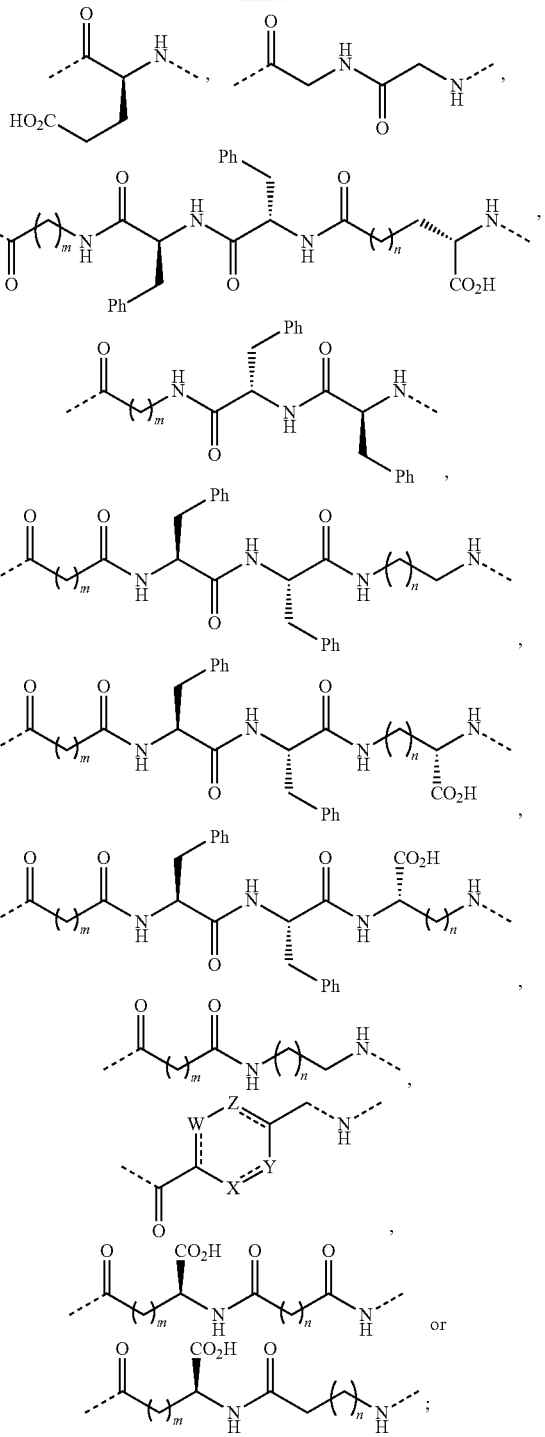

wherein
R$^1$ represents C$_1$-C$_3$ alkyl, C$_1$-C$_3$ alkoxy, C$_1$-C$_3$ haloalkyl, C$_1$-C$_3$ haloalkoxy, C$_2$-C$_4$ alkylcarbonyl, C$_2$-C$_4$ alkyloxycarbonyl, C$_2$-C$_4$ alkylcarboxy, aryloxy, arylcarboxy, cyano, or nitro;
n is an integer selected from 0 to 10;
m is an integer selected from 1 to 18;
p is an integer selected from 0 to 10, preferably 0 to 5;
X, Y, W, and Z represent independently of each other —CH$_2$—, —CH—, —NH— or —N—;

represents a single or double bond;
and diastereomers, enantiomers, hydrates, and salts thereof.

Further, the present invention relates to a method for preparing a compound of the general formula (I):

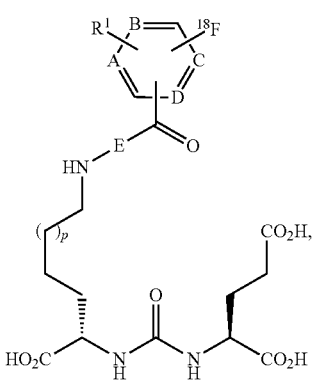
(I)

wherein
A, B, C, and D represent independently of each other C—H, C—F or N;
and not more than two of A, B, C, and D represent N;
E represents a covalent bond or

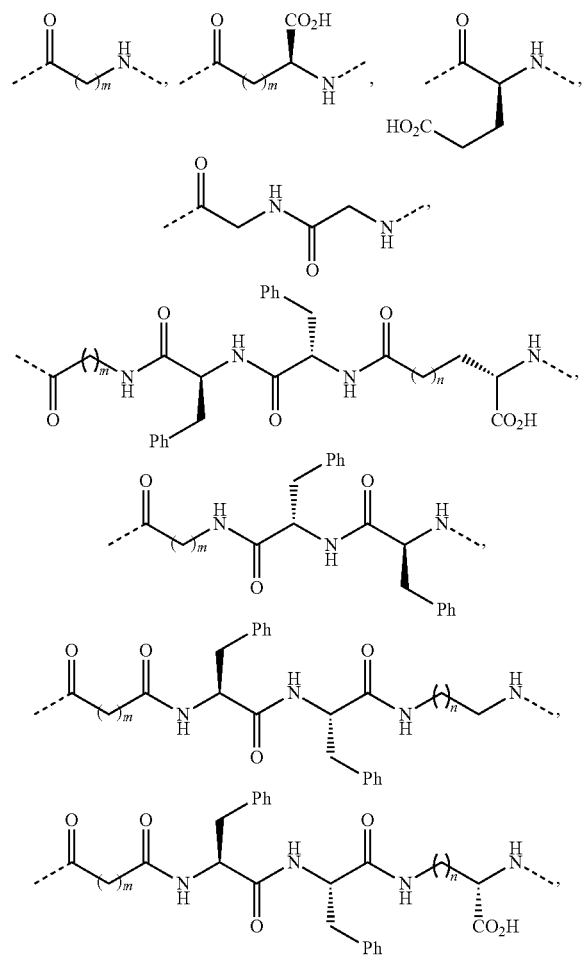

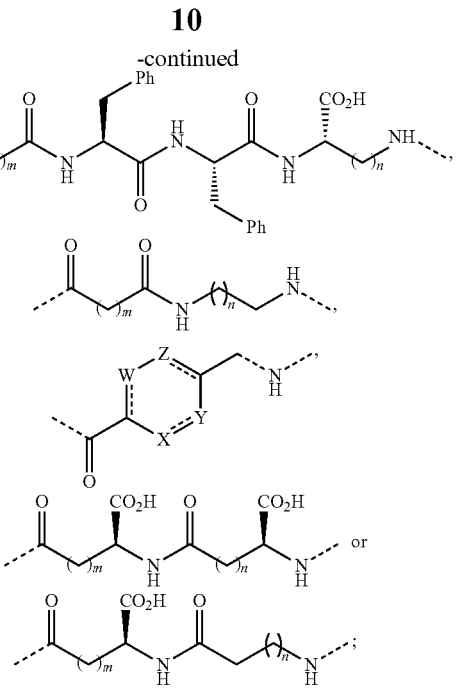

$R^1$ represents $C_1$-$C_3$ alkyl, $C_1$-$C_3$ alkoxy, $C_2$-$C_4$ alkylcarbonyl, $C_2$-$C_4$ alkyloxycarbonyl, $C_2$-$C_4$ alkylcarboxy, aryloxy, arylcarboxy, cyano, or nitro;
n is an integer selected from 0 to 10;
m is an integer selected from 1 to 18;
p is an integer selected from 0 to 10, preferably 0 to 5;
X, Y, W, and Z represent independently of each other —$CH_2$—, —CH—, —NH— or —N—;
represents a single or double bond;
and diastereomers, enantiomers, hydrates, and salts thereof.

Still further, the present invention relates to a method for preparing a compound of the general formula (I):

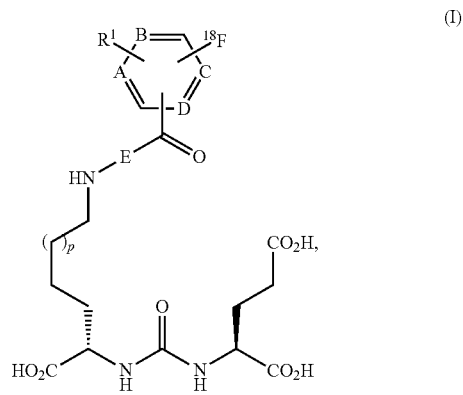
(I)

wherein A, B, C, and D represent independently of each other C—H, C—F, C—Cl, or N; and not more than two of A, B, C, and D represent N;
E represents a covalent bond or

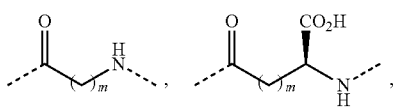

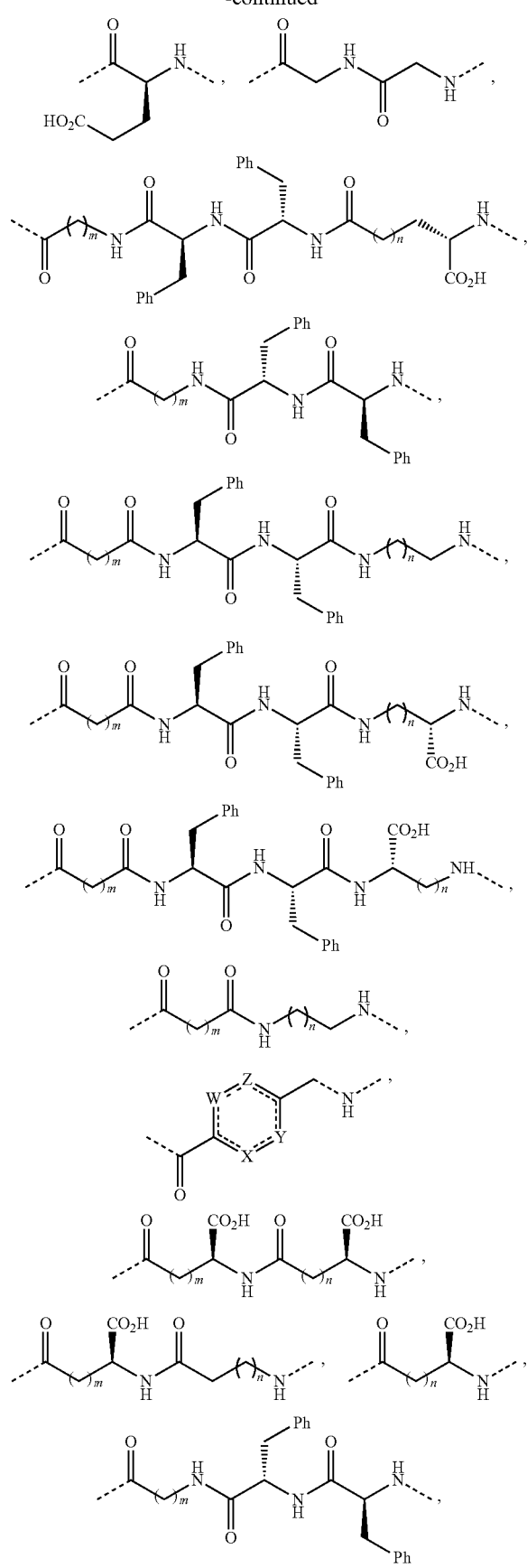

wherein
R¹ represents $C_1$-$C_3$ alkyl, $C_1$-$C_3$ alkoxy, $C_1$-$C_3$ haloalkyl, $C_1$-$C_3$ thioalkyl, $C_1$-$C_4$ haloalkoxy, $C_1$-$C_4$ alkylcarbonyl, $C_1$-$C_4$ alkyloxycarbonyl, $C_1$-$C_4$ alkylcarboxy, aryloxy, alkylaryl, aryl, arylcarboxy, halogen, preferably Cl or Br; trifluoromethyl, perfluoroalkyl, cyano or nitro;

n is an integer selected from 0 to 10;
$n_1$ is an integer selected from 0 to 10;
$n_2$ is an integer selected from 0 to 10;
m is an integer selected from 1 to 18;
p is an integer selected from 0 to 10;
q is an integer selected from 1 to 18;
X, Y, W, and Z represent independently of each other —$CH_2$—, —CH—, NH—, or —N—;
=== represents a single or double bond;
and diastereomers, enantiomers, hydrates, and salts thereof.

The present invention further provides a method of preparing formula (I) as defined I the claims.

The present invention further provides a compound of formula (II):

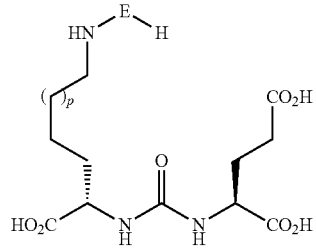

(II)

wherein, E represents a covalent bond or

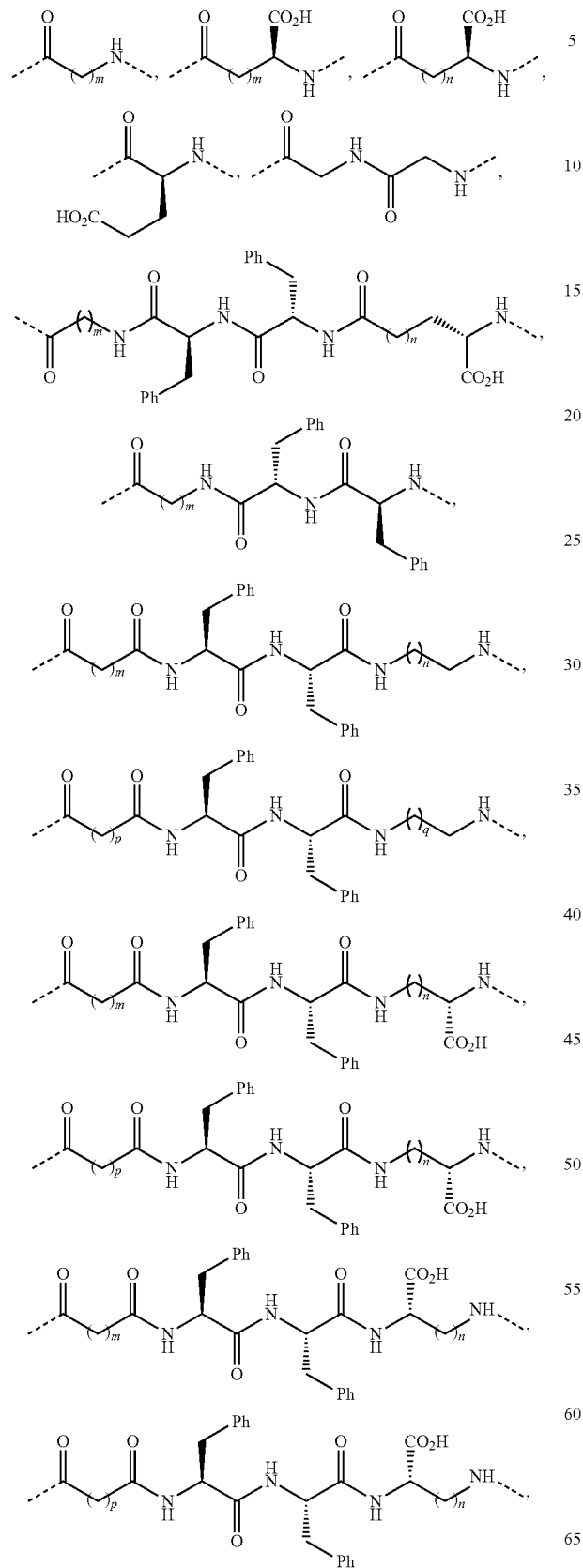

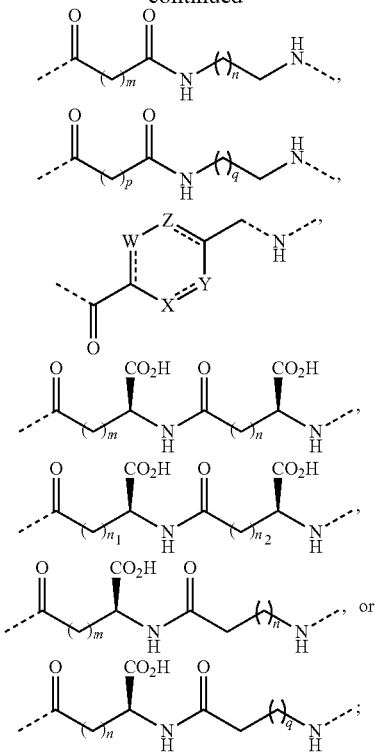

wherein
  n is an integer selected from 0 to 10;
  $n_1$ is an integer selected from 0 to 10;
  $n_2$ is an integer selected from 0 to 10;
  m is an integer selected from 1 to 18;
  p is an integer selected from 0 to 10;
  q is an integer selected from 1 to 18;
  X, Y, W, and Z represent independently of each other —$CH_2$—, —CH—, —NH— or —N—;
  ⸺ represents a single or double bond;
  and diastereomers, enantiomers, hydrates, and salts thereof.

The invention also provides a compound of formula (II)

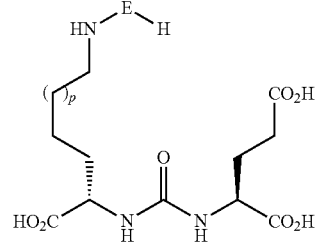

wherein, E represents a covalent bond or

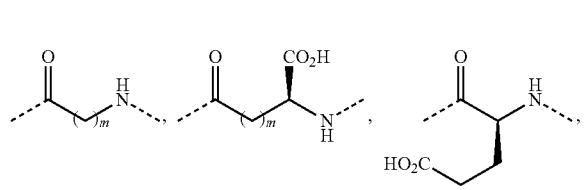

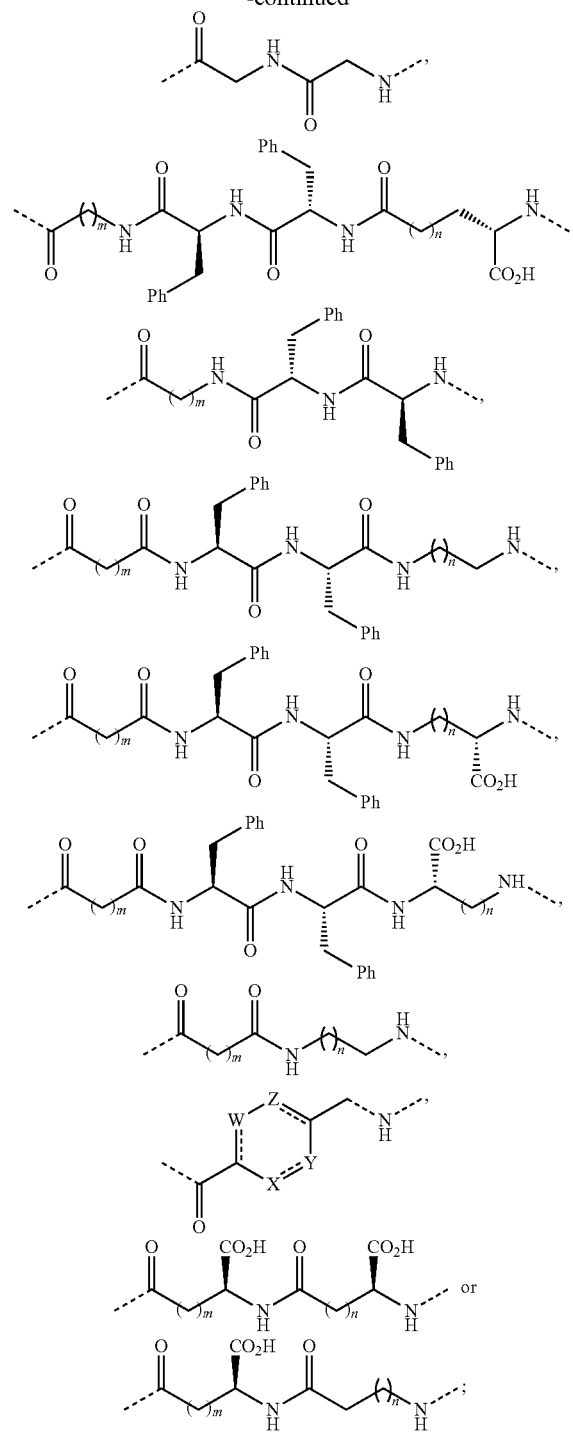

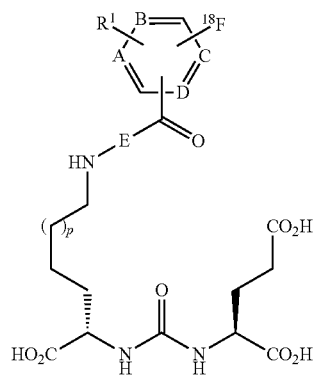

wherein A, B, C, and D represent independently of each other C—H, C—F, C—Cl, or N; and not more than two of A, B, C, and D represent N;

E represents a covalent bond or wherein
n is an integer selected from 0 to 10;
m is an integer selected from 1 to 18;
X, Y, W, and Z represent independently of each other —CH$_2$—, —CH—, —NH— or —N—;
---- represents a single or double bond;
and diastereomers, enantiomers, hydrates, and salts thereof.

In a further embodiment the above compounds (II) are direct precursors of the compound of formula (I) as defined in any of the above embodiments, or they are used as direct precursors:

-continued

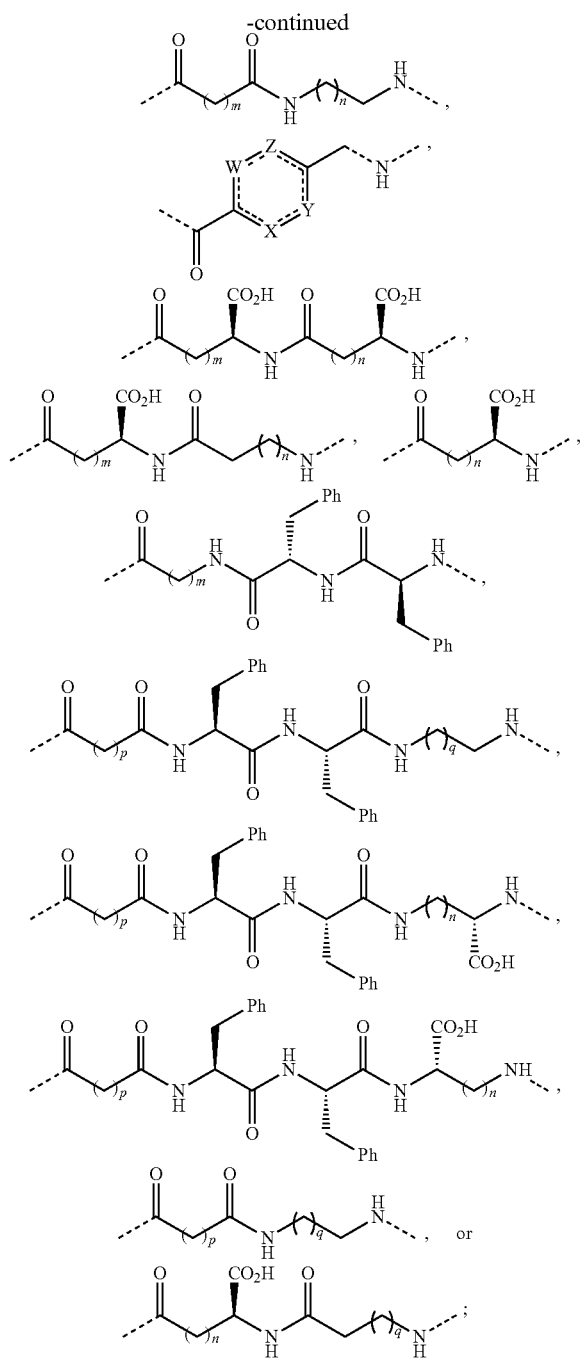

wherein
R[1] represents $C_1$-$C_3$ alkyl, $C_1$-$C_3$ alkoxy, $C_1$-$C_3$ haloalkyl, $C_1$-$C_3$ thioalkyl, $C_1$-$C_4$ haloalkoxy, $C_1$-$C_4$ alkylcarbonyl, $C_1$-$C_4$ alkyloxycarbonyl, $C_1$-$C_4$ alkylcarboxy, aryloxy, alkylaryl, aryl, arylcarboxy, Cl, Br, trifluoromethyl, cyano or nitro;
n is an integer selected from 0 to 10;
$n_1$ is an integer selected from 0 to 10;
$n_2$ is an integer selected from 0 to 10;
m is an integer selected from 1 to 18;
p is an integer selected from 0 to 10;
q is an integer selected from 1 to 18;

X, Y, W, and Z represent independently of each other —$CH_2$—, —CH—, —NH—, or —N—;
═ represents a single or double bond;
and diastereomers, enantiomers, hydrates, and salts thereof.

In further embodiments of the invention, the compound is a direct precursor of the compound of formula (I) or is used as direct precursor, wherein formula (I) is:

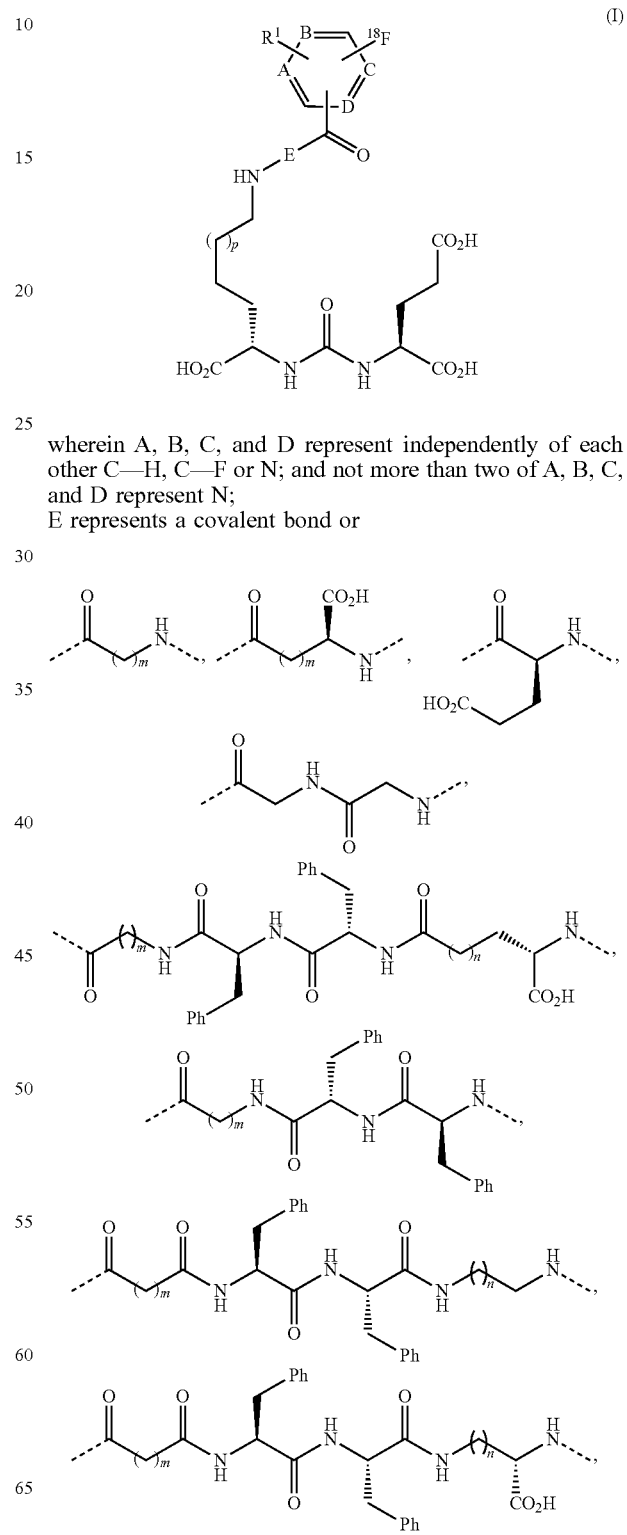

wherein A, B, C, and D represent independently of each other C—H, C—F or N; and not more than two of A, B, C, and D represent N;
E represents a covalent bond or -continued

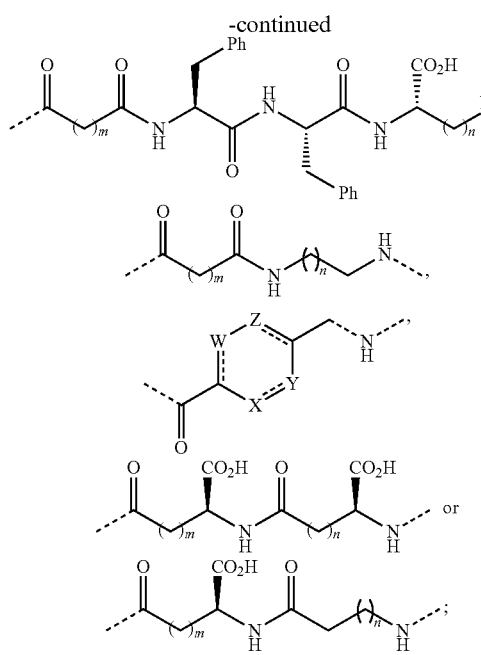

wherein
$R^1$ represents $C_1$-$C_3$ alkyl, $C_1$-$C_3$ alkoxy, $C_1$-$C_3$ haloalkyl, $C_1$-$C_3$ haloalkoxy, $C_2$-$C_4$ alkylcarbonyl, $C_2$-$C_4$ alkyloxycarbonyl, $C_2$-$C_4$ alkylcarboxy, aryloxy, arylcarboxy, cyano, or nitro;
n is an integer selected from 0 to 10;
m is an integer selected from 1 to 18;
X, Y, W, and Z represent independently of each other —$CH_2$—, —CH—, —NH— or —N—;
---- represents a single or double bond;
and diastereomers, enantiomers, hydrates, and salts thereof.

In further embodiments of the invention either of n or $n_1$ or $n_2$ in the above compounds (I) and/or (II) is an integer selected from 1-4, and preferably n or $n_1$ or $n_2$ is an integer selected from 1 or 2 in any possible combination.

In further embodiments of the invention m in the above compounds (I) and (II) is an integer selected from 1 to 10, and preferably m is an integer selected from 1 to 4 in any possible combination with any of the preceding compounds.

In further embodiments of the invention in the above compounds (I) and (II) p is an integer selected from 0 to 6, and preferably p is an integer selected from 0, 2 to 4 in any possible combination with any of the preceding compounds.

In further embodiments of the invention in the above compounds (I) and (II) q is an integer selected from 1 to 10, preferably q is an integer selected from 1 to 3 in any possible combination with any of the preceding compounds.

In further embodiments of the invention a compound of formula (II) is selected from the group comprising compounds 2a-2p:

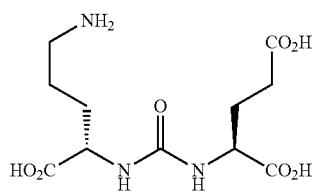

2a

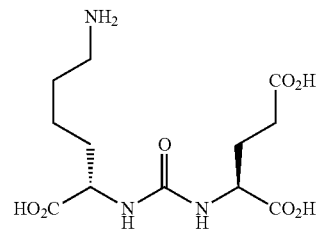

2b

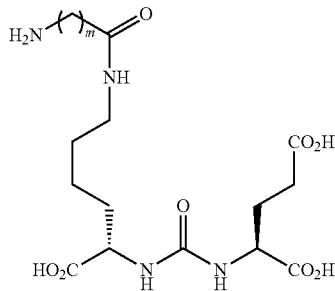

2c-j m = 1-8

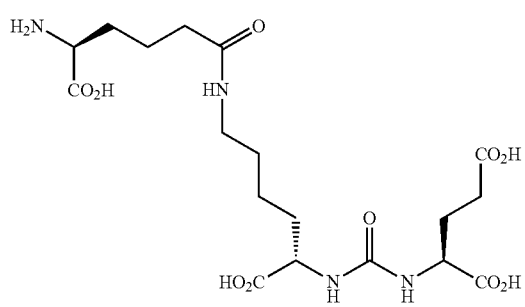

2k

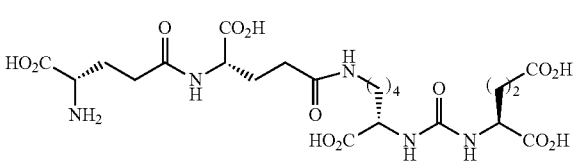

2n

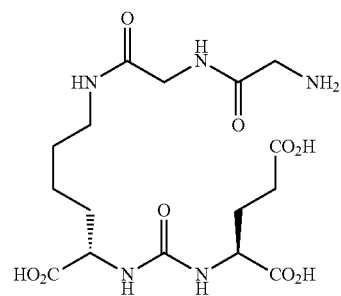

2p

In further embodiments of the invention the compound of formula (I) or (II), the salt is selected from the group comprising acetate, trifluoroacetate, tosylate, mesylate, triflate, chloride, bromide, iodide, sulfate, hydrosulfate, nitrate, perchlorate, lithium, sodium, potassium, cesium, trialkylaryl-, tetraaryl-, tri- and tetralkylammonium salts.

Compounds of formula (II) can be prepared using procedures known in the art. In general, the materials used will be determined by the desired structure, and the type linkage used. Typically, the synthesis of the compounds is started by the preparation of urea pharmacophore units, such as the lysine-urea-glutamate compounds, for example, as described by Maresca et al. (J. Med. Chem., 2009, 52 (2), pp 347-357). Other urea-glutamate based compounds may also be used as building blocks. Compounds II may be readily prepared by reactions between amines and activated carboxylic acids or active esters, such as an acyl anhydride and acyl halide or N-hydroxysuccinimide and 2,3,5,6-tetrafluorophenyl ester. Carboxylic acids may also be activated in situ, for example, with coupling reagent, such as carbodiimides, benzotriazole-, 7-azabenzotriazole-, succinimide-derived phosphonium and uronium salts, or carbonyldiimidazole (CDI). Active esters may be formed by reaction between alcohols and activated carboxylic acids.

Protecting groups may be used, if necessary, to protect reactive groups while the compounds are being assembled. Suitable protecting groups and conditions for their removal will be readily available to one of ordinary skill in the art. In this way, the compounds may be easily prepared from individual building blocks, such as amines, carboxylic acids, and amino acids (see examples 15-18).

In further embodiments of the present invention, the direct precursor of the compound of formula (I) is suitable of being coupled to a compound of formula (III), optionally in an anhydrous protic solvent, preferably in a $C_2$-$C_5$ alcohol, preferably ethanol wherein formula (III) is

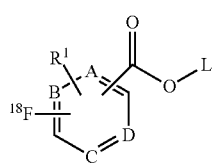
(III)

wherein A, B, C, D and $R^1$ have the meanings as defined above, and

OL represents a leaving group, optionally wherein the residue L of the leaving group OL in formula (III) represents preferably:

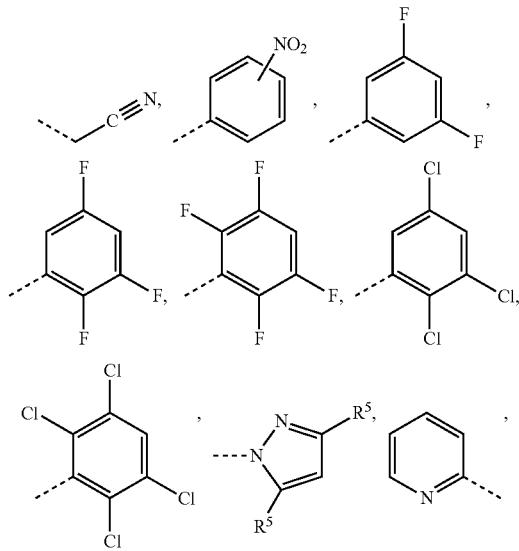

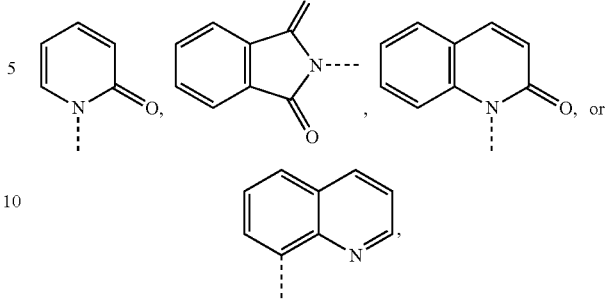

and wherein $R^5$ is selected from methyl, ethyl, or n-propyl, further optionally wherein the compound (III) is selected from the group comprising:

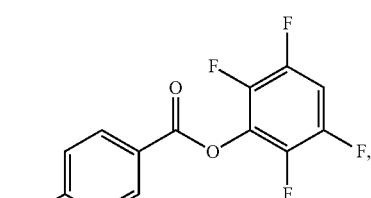
3a

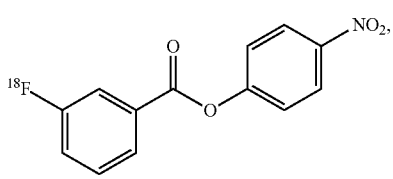
3b

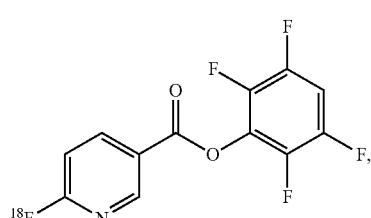
3c

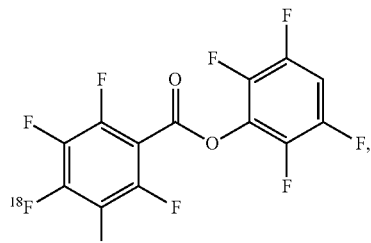
3d

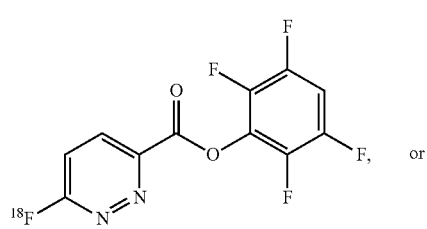
3e

-continued

3f

[Structure: pyrazine-2-carboxylic acid 2,3,5,6-tetrafluorophenyl ester with $^{18}F$ substituent]

The present invention relates also to a method of preparing a compound (III) comprising the following steps (A1)-(A8):

(A1) providing a solution of a compound of the formula (IV) in at least one polar protic solvent or in a solvent mixture containing a polar protic solvent, (IV)

[Structure of formula (IV) with $Y^-X^+$, $R^1$, A, B, C, D, and OL groups]

wherein
A, B, C, D, OL and $R^1$ have the same meanings as defined above;
X represents $NR^2{}_3$, $IR^3$, $SR^3{}_2$;
Y represents Br, I, $BF_4$, $O_2CCF_3$, $OSO_2CF_3$, $ClO_4$, $NO_2$, $OSO_2C_6H_4CH_3$, $OSO_2CH_3$;
$R^2$ represents $C_1$-$C_4$ alkyl; and
$R^3$ represents aryl;

(A2) providing an aqueous solution of [$^{18F}$]fluoride;
(A3) loading the aqueous solution of [$^{18F}$]fluoride onto an anion exchange resin;
(A4) washing the anion exchange resin with a polar protic solvent or with a polar aprotic solvent;
(A5) flushing of the solvent with air or inert gas flow;
(A6) eluting of [$^{18}F$]fluoride with the solution of the compound of formula (IV) provided in step (A1), preferably in EtOH and diluting of the resulting solution with an aprotic solvent or with at least one $C_3$-$C_6$ alcohol or with a solvent mixture of at least one $C_3$-$C_6$ alcohol and an aprotic solvent, preferably with tBuOH/MeCN 1:4;
or
eluting of [$^{18}F$]fluoride with the solution of the compound of formula (IV) provided in step (A1), preferably in MeOH concentrating of the resulting solution and redissolving of the residue in an aprotic solvent, preferably in DMSO;
(A7) allowing the compound of formula (IV) to react with [$^{18}F$]fluoride in order to obtain the compound of the formula (III);

(III)

[Structure of formula (III) with $^{18}F$, $R^1$, A, B, C, D, and OL groups]

wherein A, B, C, D, OL and $R^1$ have the same meanings as defined above; and
(A8) purifying of the compound of formula (III).

The present invention also relates to the use of a compound of formula (II) as defined in any of the foregoing paragraphs in the preparation of compound (I) as defined above.

The present invention also relates to a method for preparing a compound of formula (I) as defined above, (I)

[Structure of formula (I) showing the full compound with $^{18}F$, aromatic ring, urea linker, and dicarboxylic acid groups]

comprising the steps:
(A) providing a solution of a compound of formula (II) as defined above in a polar protic solvent, preferably in EtOH, or in a solvent mixture containing a polar protic solvent containing at least one base, preferably in $Et_4NHCO_3$;

(II)

[Structure of formula (II)]

(B) providing a solution of a compound of formula (III) as defined above (III)

[Structure of formula (III)]

in a polar protic solvent, preferably in EtOH, or in a solvent mixture containing a polar protic solvent;
(C) mixing the solution of the compound of formula (II) and the solution of the compound of formula (III) and allowing the compound of formula (II) to react with the compound of formula (III) in order to obtain the compound of formula (I),
(D) purifying the compound of formula (I), preferably by using isotonic sodium chloride solution.

The present invention also relates to a method as defined above, wherein step (C) is performed at a reaction temperature T2 which is in the range of 30° C. to 60° C., preferably 20° to 60° C., wherein the reaction time t2 of step (C) is optionally 1-30 min, and wherein the pH value of the reaction solution in step (C) is optionally in the range of 7.0-11.0.

The present invention also relates to a method as defined above, wherein the compound of formula (III) does not require purification via HPLC,
and/or wherein the method does not comprise the application of a base and any other additives such as commonly known activating compounds such as Kryptofix or 18-crown-6 or other substances known in the art; and/or wherein the method comprises the application of only onium salt precursor (IV) and [$^{18F}$]fluoride; and/or wherein the method does not comprise any azeotropic drying steps; and/or wherein the method does not require any evaporation steps.

The present invention also relates to a method as defined above, wherein the compound of formula (I) does not require purification via HPLC, and wherein the method comprises the application of environmentally benign solvents such as ethanol (rather than dichlormethane or acetonitrile that are used, e.g. according to the method of Pomper/Mease); and/or wherein the method does not comprise any evaporation steps; and/or wherein the method does not require any deprotection steps, wherein said deprotection steps may be steps of p-methoxybenzyl (PMB) or tBu deprotection using anisol/TFA mixture; and/or wherein the method does not require a neutralization step (such as described according to the method of Pomper/Mease); and/or wherein the method does not require a formulation step.

The use of toxic solvents is a particular disadvantage of methods of the prior art and is avoided in the inventive methods. The present invention does not require the use of toxic solvents, e.g. dichloromethane or acetonitrile.

The present invention also relates to a method as defined above further comprising the following step (E) after the step (D), wherein step (E) is the sterilization of the solution of the compound of formula (I) via sterile filtration.

The present invention also relates to a method as defined above further comprising steps (A1)-(A8) as defined above after step (A) and before step (B).

The present invention also relates to a method as defined above further comprising the following step (F) after the step (D) or (E): (F) preparing a pharmaceutical composition containing the solution of the compound of formula (I).

The present invention also relates to a method as defined above, wherein the base in step (A) is an organic nitrogen-containing base or a bicarbonate, wherein the bicarbonate is preferably a quaternary ammonium bicarbonate or hydrogenphosphate.

The present invention also relates to a method as defined above, wherein the organic nitrogen-containing base or the bicarbonate is selected from the group comprising: $LiHCO_3$, $NaHCO_3$, $KHCO_3$, $CsHCO_3$, $Me_4NHCO_3$, $Me_4NHPO_4$, $Et_4NHCO_3$, $Et_4NHPO_4$, $n-Pr_4NHCO_3$, $n-Pr_4NHPO_4$, $i-Pr_4NHCO_3$, $n-Bu_4NHCO_3$, $n-Bu_4NHPO_4$, $BzlMe_3NHCO_3$, $BzlMe_3NHPO_4$, $BzlEt_3NHCO_3$, $BzlEt_3NHPO_4$, $BzlBu_3NHCO_3$, $BzlBu_3NHPO_4$, $Et_3N$, pyridine, lutidine, collidine, diisopropylethylamine, $n-Pr_3N$, $i-Pr_3N$, $n-Bu_3N$, $i-Bu_3N$, $Oct_3N$, N-methyl-morpholine, N-ethylmorpholine, N-methylpiperidine, N-ethylpiperidine, N,N-dicyclohexylmethylamine N,N-dimethylcyclohex- ylamine, N-methyl-dibutylamine, N-ethyldicyclohexylamine, N,N-dimethylbutylamine, and N,N-dimethylhexylamine.

The present invention also relates to a method as defined above, wherein the [$^{18}$F]fluoride is trapped on an anion exchange resin and then eluted directly.

The present invention also relates to a method as defined above, wherein the $C_3$-$C_6$ alcohol is tBuOH.

The present invention also relates to a method as defined above, wherein the compound of the formula (I) is selected from the group consisting of compounds 1-3, 1-10, 1-14, 1-17, 1-29, 1-31, 1-32, 1-33, and 1-34:

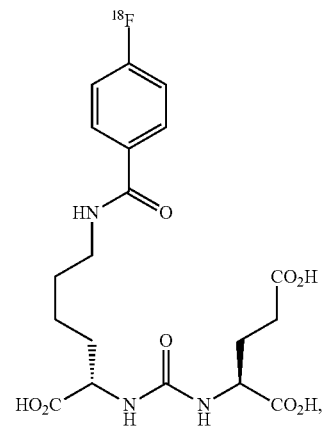

1-3

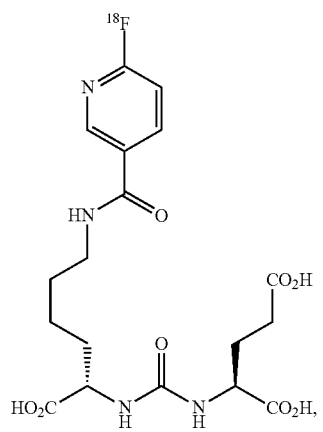

1-10

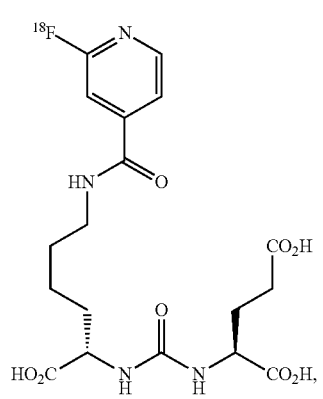

1-14

1-17
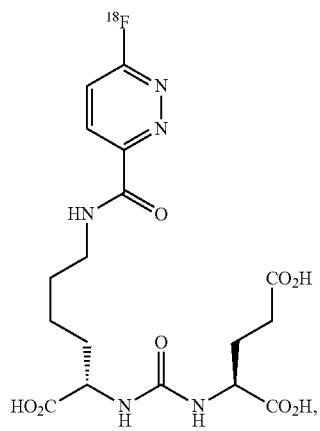
1-34
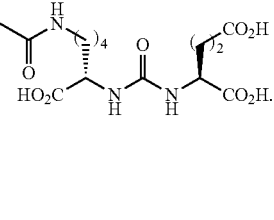
The inventive method for preparing the compounds of the general formula (I) may also comprise the following steps:
(A) providing a solution of a compound of formula (II) in a polar protic solvent or in a solvent mixture containing a polar protic solvent containing at least one base
1-29
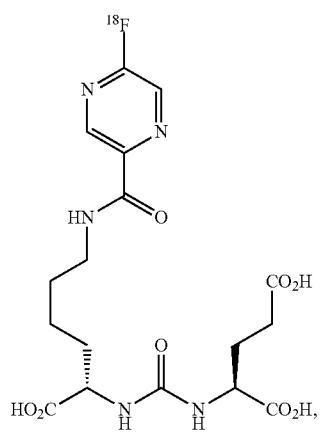
(II)
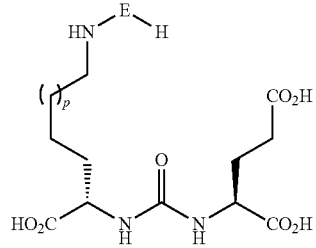
wherein
E represents a covalent bond or
1-31
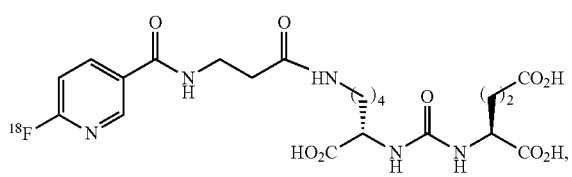
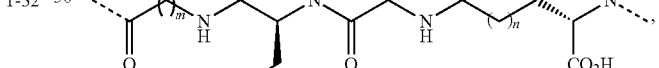
1-32
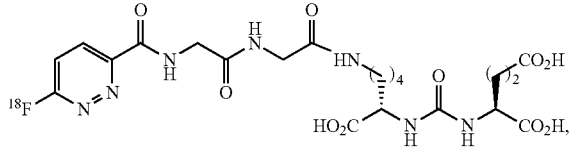
1-33
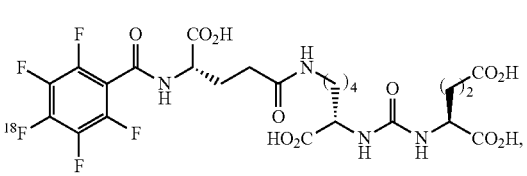 and
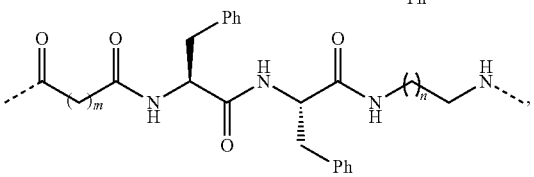

-continued

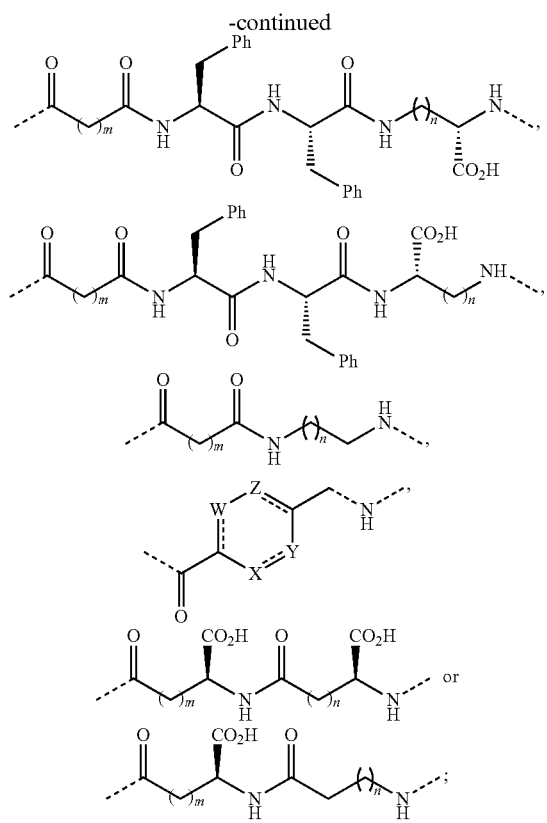

R¹ represents $C_1$-$C_3$ alkyl, $C_1$-$C_3$ alkoxy, $C_1$-$C_3$ haloalkyl, $C_1$-$C_3$ haloalkoxy, $C_2$-$C_4$ alkylcarbonyl, $C_2$-$C_4$ alkyloxycarbonyl, $C_2$-$C_4$ alkylcarboxy, aryloxy, arylcarboxy, cyano, or nitro;

n is an integer selected from 0 to 10;
m is an integer selected from 1 to 18;
p is an integer selected from 0 to 10, preferably 0 to 5;
X, Y, W, and Z represent independently of each other —$CH_2$—, —CH—, —NH— or —N—;
==== represents a single or double bond;

(B) providing a solution of a compound of formula (III)

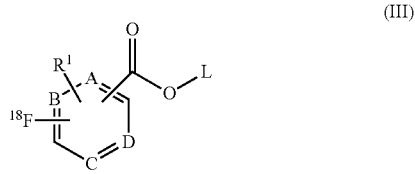

wherein
A, B, C, D and R¹ have the meanings as defined above, and
OL represents a leaving group
in a polar protic solvent or in a solvent mixture containing a polar protic solvent;
(C) mixing the solution of the compound of formula (II) and the solution of the compound of formula (III) and allowing the compound of formula (II) to react with the compound of formula (III) in order to obtain the compound of formula (I);
(D) purifying the compound of formula (I) preferably by using saline (which is isotonic sodium chloride solution).

The residue L of the leaving group OL represents preferably:

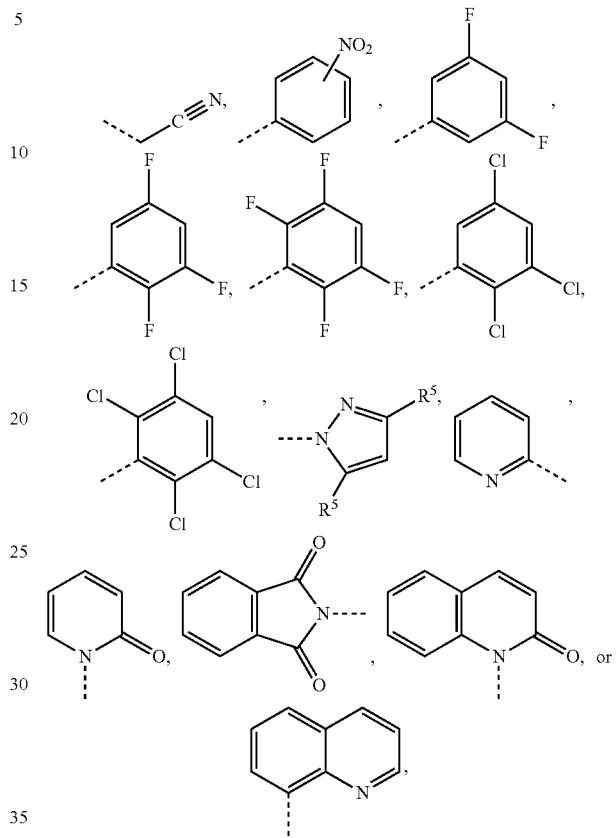

and wherein R⁵ is selected from methyl, ethyl, or n-propyl.

It is also preferred if A or B or C or D is nitrogen and the other substituents are CH or CF. More preferred are compounds wherein A and B are nitrogen and C and D are CH or CF or wherein B and C are nitrogen and A and D are CH or CF or wherein C and D are nitrogen and A and B are CH or CF or wherein A and D are nitrogen and B and C are CH or CF or wherein A and C are nitrogen and B and D are CH or CF or wherein B and D are nitrogen and A and C are CH or CF or wherein A, B, C, D are CH or wherein A, B, C, D are CF.

Further preferred are compounds wherein the moiety

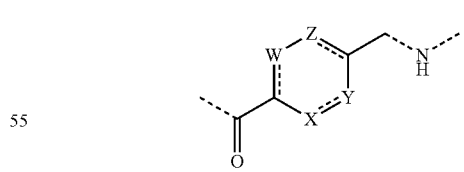

contains an aromatic nitrogen heterocyclic ring wherein one of X, Y, W, and Z is nitrogen and the other substituents are CH, or wherein X and Y or W and Z or X and W or Z and Y or X and Z or W and Y are nitrogen and the other two substituents are CH.

p is preferably selected from 0, 1, 2, 3, 4 and 5, more preferably from 0, 1, 2, 3 and 4, still more preferably from 0, 1, 2 and 3, still more preferably from 0, 1 and 2, and most preferably from 0 and 1.

An embodiment of the present invention refers to any one of the above-described methods, wherein the base of step (A) is an organic nitrogen-containing base or a bicarbonate. The organic nitrogen-containing base is preferably a mono-alkylamine, dialkylamine, trialkylamine or an ammonium base, especially a tetraalkylammonium base and more preferably a trialkylamine or tetraalkylammonium base, wherein the term "trialkylamine" and the term "tetraalkylammonium" covers also cyclic amines and cyclic ammonium ions such as N-ethylmorpholine and N-methylpiperidine. Said organic nitrogen-containing base or said bicarbonate is preferably selected from the group comprising or consisting of: $Me_4NHCO_3$, $Et_4NHCO_3$, $n\text{-}Pr_4NHCO_3$, $i\text{-}Pr_4NHCO_3$, $n\text{-}Bu_4NHCO_3$, $i\text{-}Bu_4NHCO_3$, $Et_3N$, pyridine, lutidine, collidine, diisopropylethylamine, $n\text{-}Pr_3N$, $i\text{-}Pr_3N$, $n\text{-}Bu_3N$, $i\text{-}Bu_3N$, $Oct_3N$, N-methyl-morpholine, N-ethylmorpholine, N-methylpiperidine, N-ethylpiperidine, N,N-dicyclohexylmethylamine, N,N-dimethylcyclohexylamine, N-methyldibutylamine, N-ethyldicyclohexylamine, N,N-dimethylbutylamine, and N,N-dimethylhexylamine. Said bicarbonate may be selected from the group comprising or consisting of: $LiHCO_3$, $NaHCO_3$, $KHCO_3$, $CsHCO_3$, $Me_4NHCO_3$, $Et_4NHCO_3$, $n\text{-}Pr_4NHCO_3$, and $n\text{-}Bu_4NHCO_3$; and preferably from $Me_4NHCO_3$, $Et_4NHCO_3$, $n\text{-}Pr_4NHCO_3$, and $n\text{-}Bu_4NHCO_3$ or may be as defined above.

In one embodiment of the present invention, said method comprising the step (C), wherein step (C) is performed at a reaction temperature T2 which is in the range of 20° C. to 130° C., preferred 20° C. to 100° C., more preferred more preferred 30° C. to 80° C., most preferred 20° C. to 600 or 30° C.-60° C. and during a reaction time t2 which is in the range of 0.1-40 min, preferred 0.1-30 min, more preferred 0.5-15 min, most preferred 1-10 min and at a pH value of the reaction solution which is in the range of 7.0 to 11.0. More preferably step (C) is performed during a reaction time t2 of 1 to 5 minutes at a pH value of 7.0 to 11.0. Still more preferably step (C) is performed during a reaction time t2 of 1 to 5 minutes at a pH value of 7.0 to 11.0 and at a reaction temperature T2 in the range of 20° C. to 80° C. and more preferably in the range of 30° C. to 60° C.

In the step (D), the compound of the formula (I) is preferred purifed by preparative HPLC. As eluent saline may be suitable for purifying the compound of the formula (I). Said saline is preferred isotonic sodium chloride solution containing 0.90% (weight/volume, 9 g/1000 mL) of sodium chloride. Optionally, said saline may further contains 5-15% (volume/volume) of EtOH.

Alternatively, phosphate buffered solution can be used for purifying the compound of the formula (I). The phosphate buffered solution usually comprises sodiumphosphate, potassium phosphate and/or phosphoric acid. Optionally said phosphate buffered solution further comprises sodium chloride and/or potassium chloride. Preferred, the osmolarity and ion concentration of said phosphate buffered solution match those of the human body (isotonic). The pH value of said phosphate buffered solution is in the range of 2.0 to 9.0, preferred 4.0 to 8.0, more preferred 6.0 to 8.0 and most preferred 7.0 to 7.8. For example, PBS (phosphate buffered saline) can be used for purifying the compound of the formula (I).

This purification step is a technical advantage compared with the prior art. In the prior art as shown in scheme 4, the HPLC purification was performed by using an aqueous eluent containing toxic acetonitrile and trifluoroacetic acid (TFA). Thus, the solution of the purified compound is not suitable for direct use for PET imaging. The toxic solvents should be firstly removed and the compound residue should be redissolved in the appropriate buffer solution. In contrast, in according to the present invention the resulting isotonic solution of the purified compound of the formula (I) after the step (D) is ready for application.

Reverse phase column having a good hydrophobic retention and selectivity may be suitable for the purification (e.g. Synergi 4 μm Hydro-RP 80 Å 100×21.2 mm). The phase should be good suitable for the separation of high polar hydrophilic compounds. Retention time should preferentially be less than 10 min by flow rate which is less than 10 mL/min.

In one embodiment of the present invention, any one of the above-mentioned methods further comprises the following step (E) after the step (D):

(E) sterilizing the solution of the compound of formula (I) via sterile filtration.

In one embodiment of the present invention, any one of the above-mentioned methods further comprises the following steps (A1)-(A8) after step (A) and before step (B):

(A1) providing a solution of a compound of formula (IV) in at least one polar protic solvent or in a solvent mixture containing a polar protic solvent, wherein optionally the solution further contains a salt;

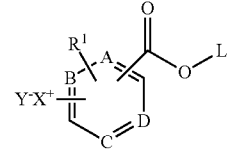

(IV)

wherein

A, B, C, D, L (or OL) and $R^1$ have the same meanings as defined above;

X represents $NR^2{}_3$, $IR^3$, $SR^3{}_2$;

Y represents Br, I, $BF_4$, $O_2CCF_3$, $OSO_2CF_3$, $ClO_4$, $NO_2$, $OSO_2C_6H_4CH_3$, $OSO_2CH_3$;

$R^2$ represents $C_1\text{-}C_4$ alkyl; and $R^3$ represents aryl;

(A2) providing an aqueous solution of [$^{18}$F]fluoride (irradiated [$^{18}$O]water);

(A3) loading an aqueous solution of [$^{18}$F]fluoride onto an anion exchange resin;

(A4) washing the anion exchange resin with a polar protic solvent or with a polar aprotic solvent;

(A5) flushing of the solvent with air or inert gas flow;

(A6) Eluting of [$^{18}$F]fluoride with the solution of the compound of the formula (IV) provided in the step (A1) and diluting of the resulting solution with an aprotic solvent or with at least one $C_3\text{-}C_6$ alcohol or with a solvent mixture of at least one $C_3\text{-}C_6$ alcohol and an aprotic solvent; or eluting of [$^{18}$F]fluoride with the solution of the compound of the formula (IV) provided in the step (A1), concentrating of the resulting solution and redissolving of the residue in an aprotic solvent;

(A7) allowing the compound of formula (IV) to react with [$^{18}$F]fluoride in order to obtain the compound of the formula (III);

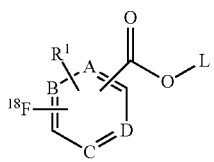

(III)

wherein A, B, C, D, L (or OL) and R¹ have the same meanings as defined above; and (A8) purifying of the compound of the formula (III).

An embodiment of the present invention refers to the above-described inventive method, wherein said polar protic solvent is an anhydrous polar protic solvent, preferably an anhydrous $C_1$-$C_4$ alcohol, diols such as 1,4-butanediol or glycols such as diglycol, triglycol or tetraglycol, and especially anhydrous MeOH or anhydrous EtOH or a mixture thereof.

The use of an anhydrous protic solvent is advantageous in the steps (A)-(C) of the inventive method, because the presence of water prevents or impedes coupling reaction between the compound of the formula (II) and the compound of the formula (III). In the presence of water, the active esters of formula (III) having a leaving group —O-L may react with water and form an undesired product i.e. the corresponding carboxylic acid. This results in lower yield of the compound of the formula (I).

For the same reason, in the steps (A1)-(A7), said polar protic solvent is preferably an anhydrous polar protic solvent, more preferred an anhydrous $C_1$-$C_4$ alcohol, diols such as 1,4-butanediol or glycols such as diglycol (HO—$C_2H_4$—O—$C_2H_4$—OH), triglycol (HO—$C_2H_4$—O—$C_2H_4$—O—$C_2H_4$—OH) or tetraglycol (HO—$C_2H_4$—O—$C_2H_4$—O—$C_2H_4$—O—$C_2H_4$—OH), and especially anhydrous MeOH or anhydrous EtOH or a mixture thereof. In the steps (A1)-(A7), the presence of water prevents or impedes a nucleophilic aromatic substitution reaction of $^{18}F^-$ and results in a poor yield of the compound of formula (III).

Said salt in step (A1) is preferably a bicarbonate salt and more preferred selected from the group consisting of $Me_4NHCO_3$, $Et_4NHCO_3$, n-$Pr_4NHCO_3$, i-$Pr_4NHCO_3$, n-$Bu_4NHCO_3$ and i-$Bu_4NHCO_3$.

In the steps (A3) and (A4), said anion exchange resin is preferred a silica-based hydrophilic resin or polystyrene-based copolymer containing carbonate or bicarbonate as counter anion and contained in a cartridge For example, commercially available Sep-Pak Accell Plus QMA carbonate plus light cartridges from Waters GmbH (Eschborn, Germany) and ChromafixR 30-PS—$HCO_3$. cartridges from Macherey-Nagel (Duren, Germany) can be used.

In the steps (A4) and (A6), said polar aprotic solvent or said aprotic solvent is preferred MeCN or DMSO and said $C_3$-$C_6$ alcohol is preferred t-BuOH.

In the step (A7), the compound of the formula (IV) reacts with [$^{18}F$]fluoride in a reaction time in the range of 1-20 min, preferred 1-15 min, more preferred 5-10 min at the reaction temperature in the range of 20° C. to 140° C., preferred 30° C.-130° C., more preferred 40° C.-130° C. After the reaction is finished, the reaction mixture is preferred cooled to a temperature in the range of 15 C-30° C. by air cooling.

In the step (A8), purifying of the compound of formula (III) is performed via HPLC or solid phase extraction (SPE). HPLC purification can be carried out using, for example, polymer-based RP columns such as Chromolith SpeedRod or RP C18 or C8 columns like Luna-2 or Nucleosil. SPE purification can be carried out using, for example, Strata X or Sep-Pak C18 cartridges.

In one embodiment of the present invention, any one of the above-described methods further comprises the following step (F) after the step (D) or (E):

(F) preparing a pharmaceutical composition containing the solution of the compound of formula (I).

The compound of the formula (II) may have a good affinity to prostate-specific membrane antigen (PSMA).

Preferred, a compound of the formula (II) is selected from the compounds 2a-2p:

2a
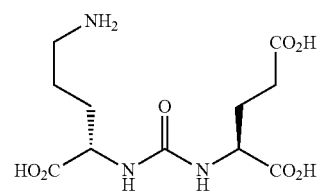

2b
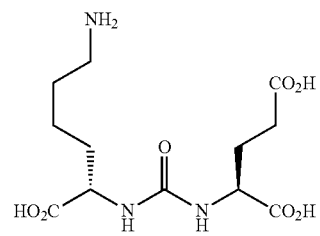

2c-j
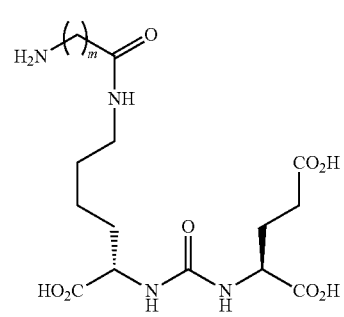

m = 1-8

2k
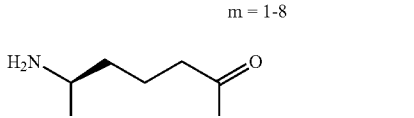

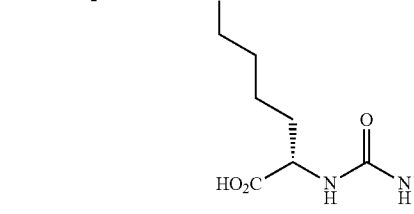

2n
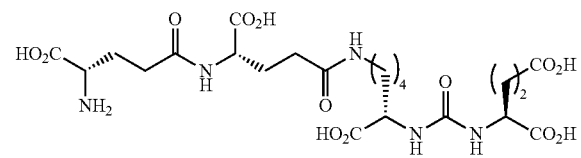

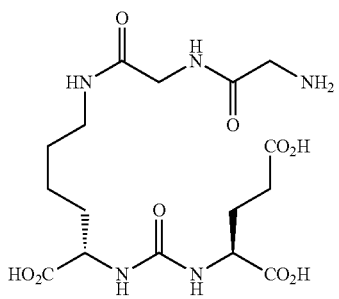

2c: m = 1, 2d: m = 2, 2e: m = 3, 2f: m = 4, 2g: m = 5, 2h: m = 6, 2i: m = 7, 2j: m = 8

Preferred, a compound of the formula (IV) having any of the subformulae (IV-1)-(IV-5) is used in the above-mentioned step (A1) of the inventive method:

(IV-1) (IV-2) (IV-3) (IV-4) (IV-5)

wherein L, $R^1$, X and Y have the same meanings as defined above.

Also preferred, a compound of the formula (IV) having any one of the subformulae (IV-6)-(IV-17) is used in the above-mentioned step (A1) of the inventive method:

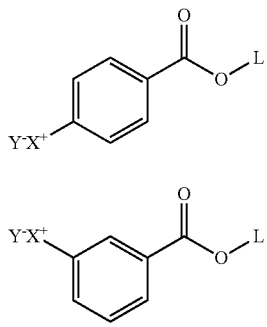

(IV-6)

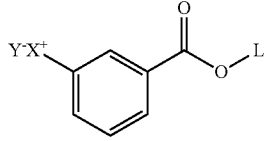

(IV-7)

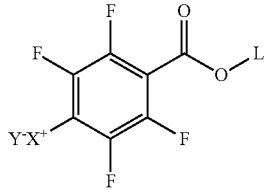

(IV-8)

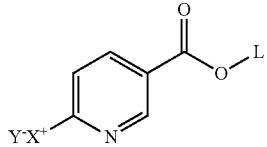

(IV-9)

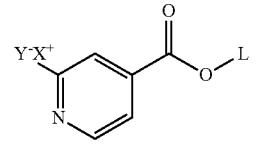

(IV-10)

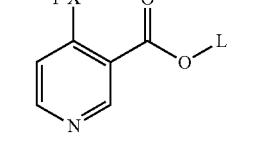

(IV-11)

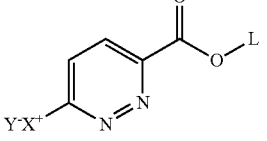

(IV-12)

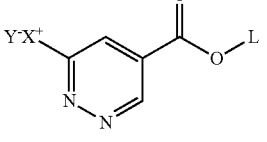

(IV-13)

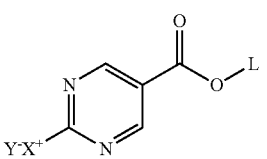

(IV-14)

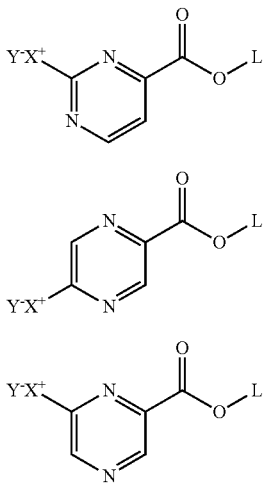

wherein L, X and Y have the same meanings as defined above.

Most preferred, a compound of the formula (IV) selected from the following compounds 4a-4f is used in the above-mentioned step (A1) of the inventive method:

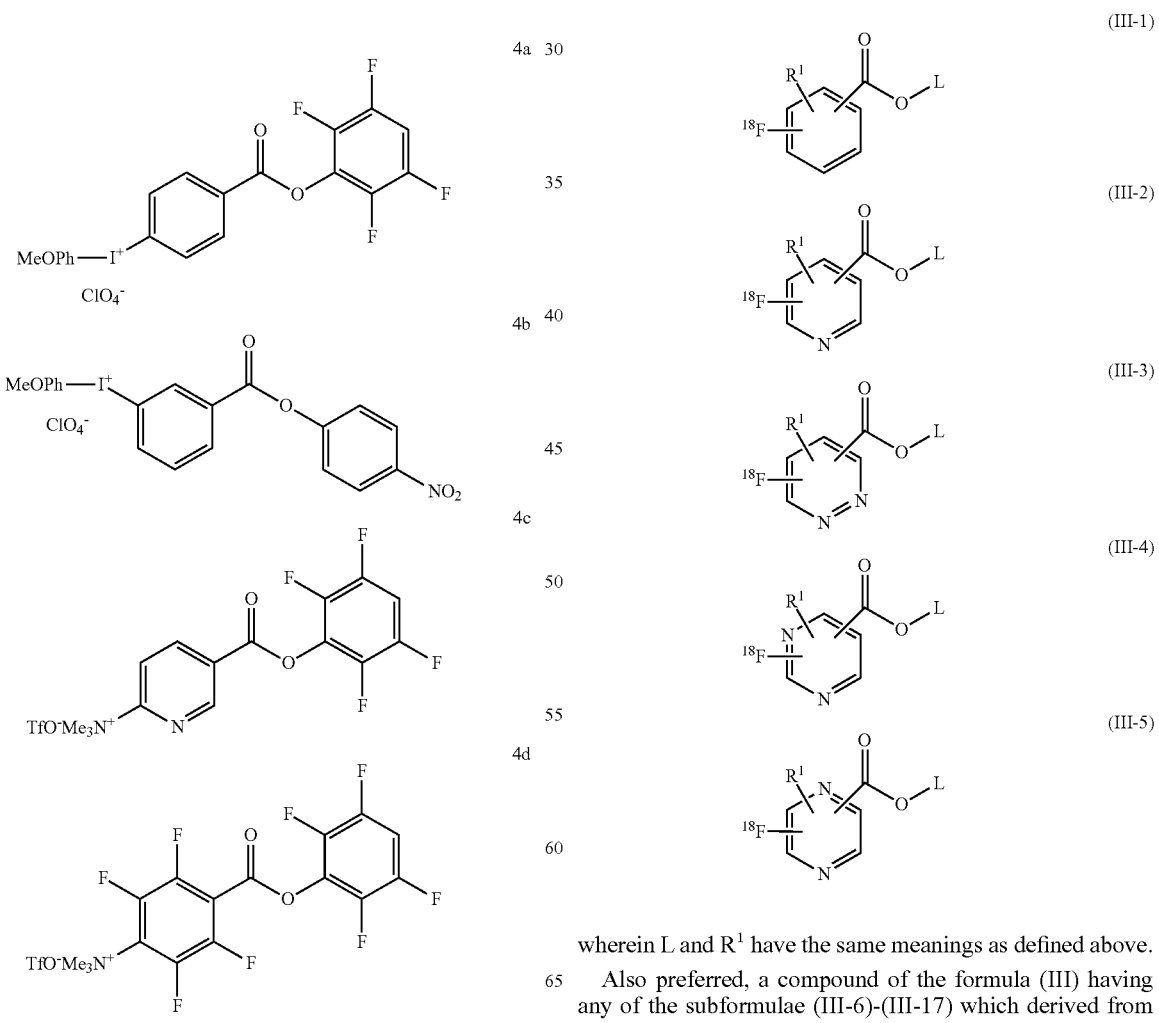

Preferred, a compound of the formula (III) having any of the subformulae (III-1)-(III-5) which derived from a compound of any of the subformulae (IV-1)-(IV-5), is obtained from the above-mentioned steps (A7) and (A8) or used in the above-mentioned step (B) of the inventive method:

wherein L and $R^1$ have the same meanings as defined above.

Also preferred, a compound of the formula (III) having any of the subformulae (III-6)-(III-17) which derived from a compound of any of the subformulae (IV-6)-(IV-17), is obtained from the above-mentioned steps (A7) and (A8) or used in the above-mentioned step (B) of the inventive method:

(III-6)
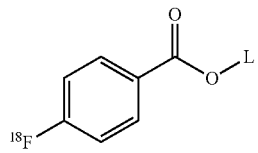

(III-7)
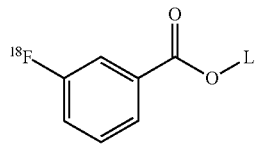

(III-8)
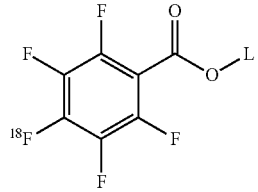

(III-9)
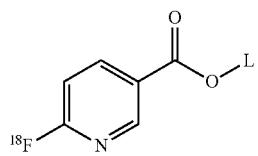

(III-10)
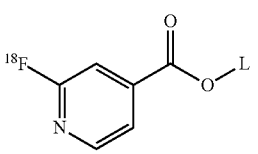

(III-11)
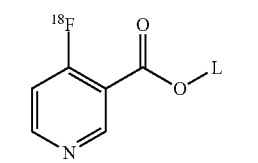

(III-12)
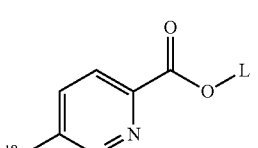

(III-13)
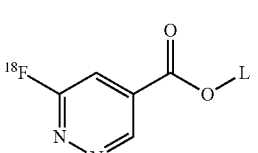

(III-14)
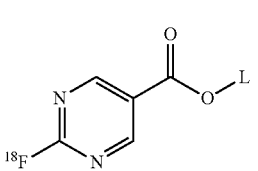

(III-15)
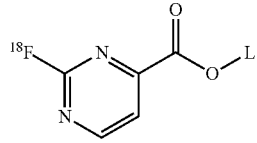

(III-16)
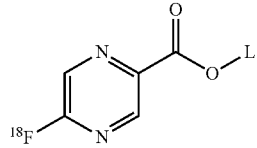

(III-17)
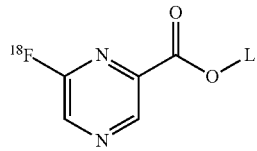

wherein L has the same meanings as defined above.

Most preferred, a compound of the formula (III) selected from the group consisting of the following compound 3a-3f derived from compounds 4a-4f, is obtained from the above-mentioned steps (A7) and (A8) or used in the above-mentioned step (B) of the inventive method:

3a
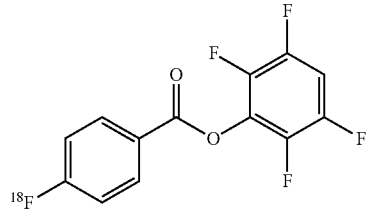

3b
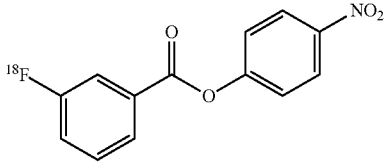

3c
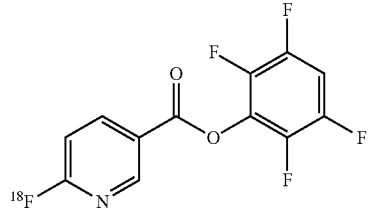

3d
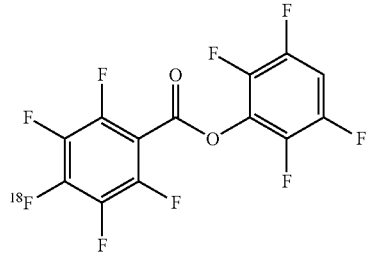

-continued

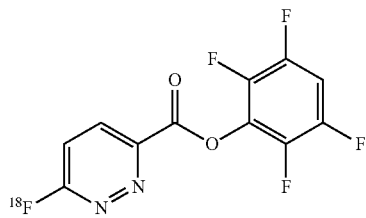

3e

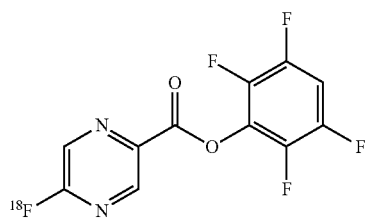

3f

The term "$C_1$-$C_3$ alkyl" as used herein refers to a saturated linear or branched carbon chain consisting of 1-4 carbon atoms. Examples are —$CH_3$, —$C_2H_5$, —$C_3H_7$, and —$CH(CH_3)_2$.

The term "$C_1$-$C_3$ alkoxy" as used herein refers to a $C_1$-$C_3$ alkyl group singular bonded to oxygen and said $C_1$-$C_3$ alkyl has the same meaning as defined above. Examples are —$OCH_3$, —$OC_2H_5$, —$OC_3H_7$, —$OCH(CH_3)_2$.

The term "$C_1$-$C_3$ haloalkyl" as used herein refers to a saturated linear or branched carbon chain consisting of 1 to 4 carbon atoms substituted by at least one halogen atom such as F, Br, Cl and I. It is clear to a skilled person that the term "substituted" refers to the replacement of a hydrogen atom by one of the substituents. Examples of a $C_1$-$C_3$ haloalkyl are —$CH_2F$, —$CHF_2$, —$CF_3$, —$CCl_3$, —$CH_2CF_3$, —$C_2F_5$, —$C_3F_7$, —$CH(CF_3)_2$.

The term "$C_1$-$C_3$ haloalkoxy" as used herein refers to a $C_1$-$C_3$ haloalkyl group singular bonded to oxygen and said $C_1$-$C_3$ haloalkyl group has the same meaning as defined above. Examples are —$OCH_2F$, —$OCHF_2$, —$OCF_3$, —$OCCl_3$, —$OCH_2CF_3$, —$OC_2F_5$, —$OC_3F_7$, —$OCH(CF_3)_2$.

The terms "$C_1$-$C_4$ alkylcarbonyl" and "$C_2$-$C_4$ alkylcarbonyl" as used herein refer preferably to a $C_1$-$C_3$ alkyl group singular bonded to carboxy group and said $C_1$-$C_3$ alkyl has the same meaning as defined above. Examples are —$COCH_3$, —$COC_2H_5$, —$COC_3H_7$, —$COCH(CH_3)_2$.

The terms "$C_1$-$C_4$ alkylcarboxy" and "$C_2$-$C_4$ alkylcarboxy" as used herein refer preferably to a $C_1$-$C_3$ alkyl group singular bonded to carboxy group (—$CO_2$—) and said $C_1$-$C_3$ alkyl has the same meaning as defined above. Examples are —$O_2CCH_3$, —$O_2CC_2H_5$, —$O_2CC_3H_7$, —$O_2CCH(CH_3)_2$.

The terms "$C_1$-$C_4$ alkyloxycarbonyl" and "$C_2$-$C_4$ alkyloxycarbonyl" herein refers to a a $C_1$-$C_3$ alkyl group singular bonded to oxy carbonyl group (—O—CO—) and said $C_1$-$C_3$ alkyl has the same meaning as defined above. Examples are —$CO_2CH_3$, —$CO_2C_2H_5$, —$CO_2C_3H_7$, —$CO_2CH(CH_3)_2$.

The terms "aryl" as used herein refer to carbocyclic aromatic or heterocyclic aromatic residues or more specific to "$C_6$-$C_{10}$ carbocyclic aromatic residues with one or two aromatic rings and refers preferably to phenyl and naphthyl, wherein these aromatic or heteroaryl residues, preferred phenyl, thienyl and naphthyl residues can be substituted with 1 to 5 substituents selected from halogen like —F, —Br, —Cl, —I, $C_1$-$C_3$ alkyl, $C_1$-$C_3$ alkoxy, $C_1$-$C_3$ haloalkyl, $C_1$-$C_3$ haloalkoxy, —CN, —OH, —$NO_2$, —$CO_2$($C_1$-$C_3$ alkyl), —NHCO($C_1$-$C_3$ alkyl), —NH($C_1$-$C_3$ alkyl), —N($C_1$-$C_3$ alkyl)$_2$. It is clear to a skilled person that the term "can be substituted" refers to the replacement of a hydrogen atom by one of the said substituents. The carbon atom number of $C_6$-$C_{10}$ refers only to the carbon atoms of the aromatic ring system (aryl) and does not include the carbon atoms of the said substituents. Examples are

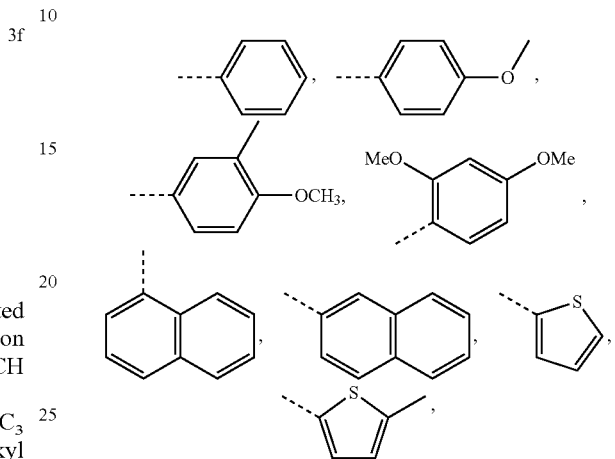

The term "aryloxy" as used herein refers to a aryl group singular bonded to oxygen and said aryl has the same meaning as defined above.

The term "arylcarboxy" as used herein refers to a aryl group singular bonded to carbonyl group (—$CO_2$—) and said aryl has the same meaning as defined above.

$^{18}$F-Production

[$^{18}$F]Fluoride was produced via the $^{18}$O(p,n)$^{18}$F reaction by bombardment of enriched [$^{18}$O]water with protons using a 16 MeV cyclotron.

Preferred, the [$^{18}$F]fluoride is trapped on an anion exchange resin. The resin was washed with alcohol (e.g., with nPrOH, iPrOH, nBuOH, better with EtOH or MeOH) and drained with flow of gas (e.g., air, Ar, $N_2$, He). In the said method $^{18}$F$^-$ is directly eluted with an alcoholic solution (e.g., in nPrOH, iPrOH, nBuOH, better in EtOH or MeOH) of the corresponding onium precursor (e.g., ONP or OTFP). Alternatively, $^{18}$F$^-$ was eluted with an alcoholic solution (e.g., in nPrOH, iPrOH, nBuOH, better in EtOH or MeOH) of suitable salt, most preferably tetraethylammonium bicarbonate.

The term "$C_1$-$C_4$ alcohol" as used herein refers to a saturated linear, branched or cyclic $C_1$-$C_4$ alkyl group substituted by at least one hydroxyl group. It is clear to a skilled person that the term "substituted" refers to the replacement of a hydrogen atom by one of the substituents. Examples of a $C_1$-$C_4$ alcohol are $CH_3OH$, $CH_3CH_2OH$, $HOCH_2CH_2OH$, $CH_3CH_2CH_2OH$, $HOCH_2CH_2CH_2OH$, $HOCH_2CH(OH)CH_3$, $HOCH_2CH(OH)CH_2OH$, $(CH_3)_2CHOH$, $CH_3CH_2CH_2CH_2OH$, $CH_3CH_2CH(OH)CH_2OH$, $CH_3CH(OH)CH_2CH_2OH$, $CH_2(OH)CH_2CH_2CH_2OH$, $CH_2(OH)CH(OH)CH_2CH_2OH$, $CH_3CH(OH)CH(OH)CH_2OH$, $CH_2(OH)CH(OH)CH(OH)CH_2OH$, $(CH_3)_2CHCH_2OH$, $H_3CCH(CH_2OH)_2$, $HC(CH_2OH)_3$, and $(CH_3)_3C$—OH. Preferred, $CH_3OH$ or $CH_3CH_2OH$ is used as the $C_1$-$C_4$ alcohol in the above-described method.

The term "$C_3$-$C_6$ alcohol" as used herein refers to a saturated linear, branched or cyclic $C_3$-$C_6$ alkyl group substituted by at least one hydroxyl group. It is clear to a skilled person that the term "substituted" refers to the replacement of a hydrogen atom by one of the substituents. Preferred examples of a $C_3$-$C_6$ alcohol are $CH_3CH_2CH_2OH$, $(CH_3)_2CHOH$, $CH_3CH_2CH_2CH_2OH$, $(CH_3)_2CHCH_2OH$, $(CH_3)_3C$—$OH$, $CH_3CH_2CH_2CH_2CH_2OH$, $(CH_3)_2CHCH_2CH_2OH$, $CH_3CH_2CH_2CH_2CH_2CH_2OH$, $(CH_3)_2CHCH_2CH_2CH_2OH$, $HOCH_2CH_2CH_2OH$.

In an embodiment of the present invention, t-BuOH $((CH_3)_3C$—$OH)$ is used as the $C_3$-$C_6$ alcohol in the above-described method.

The term "aprotic solvent" or "polar aprotic solvent" as used herein refers to acetone, DMF, DMA, 1,2-dimethoxyethane (glyme), MeCN, 2-methoxyethyl ether (diglyme), N-methylpyrrolidinone, DMSO, sulfolane, propylenecarbonate, or THF. Preferred, MeCN, and DMSO are used.

The term "polar protic solvent" as used herein refers to any solvent that contains labile $H^+$ and readily donate protons ($H^+$) to reagents and capable of dissolve the salts. Preferred examples of a polar protic solvent are MeOH, EtOH, n-PrOH, i-PrOH, n-BuOH, $HOCH_2CH_2OH$, $HOCH_2CH_2CH_2OH$, $HOCH_2CH(OH)CH_3$, $HOCH_2CH(OH)CH_2OH$, $HC(CH_2OH)_3$, $HO$—$C_2H_4$—$O$—$C_2H_4$—$OH$, $HO$—$C_2H_4$—$O$—$C_2H_4$—$O$—$C_2H_4$—$OH$, $HO$—$C_2H_4$—$O$—$C_2H_4$—$O$—$C_2H_4$—$O$—$C_2H_4$—$OH$, $HCO_2H$ and $CH_3CO_2H$.

In an embodiment of the present invention, EtOH is used as the polar protic solvent in the above described method.

The term "RCY (radiochemical yield)" as used herein refers to the yield for the step in which the radiolabel is introduced. The RCY refers to the activity (decy-corrected) of the radiolabel led product expressed as a fraction of the activity originally present.

The term "direct precursor" as used herein indicates that the respective compound can be used without protecting groups in the preparation of a compound according to formula (I) as defined herein. The term "direct precursor" means also that it can be used in the preparation in vitro of, e.g., $^{18}F$-labelled active esters that can be used as PET tracer, expecially in the preparation of compound according to formula (I) as defined herein, which can be used as active ingredients in pharmaceutical compositions for use in PET imaging, for example in the imaging of tumors such as tumors of the prostate.

Preferred is said method for preparing a compound of any of the formulae (Ia)-(Ie):

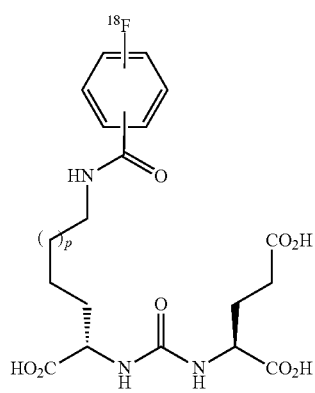

(Ia)

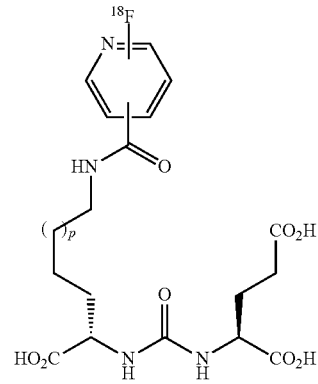

(Ib)

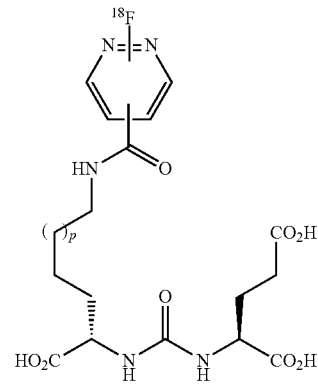

(Ic)

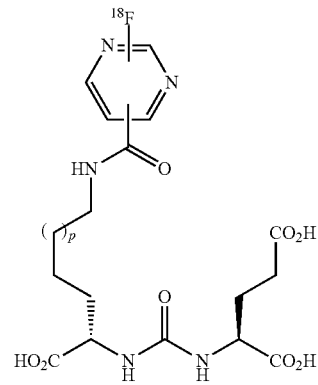

(Id)

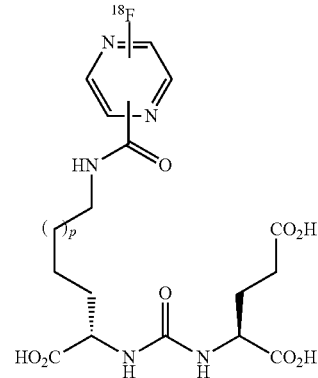

(Ie)

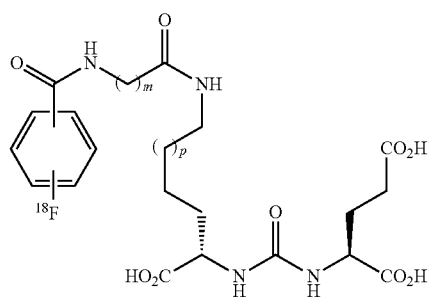
(If)
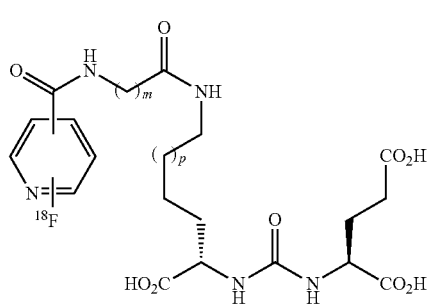
(Ig)
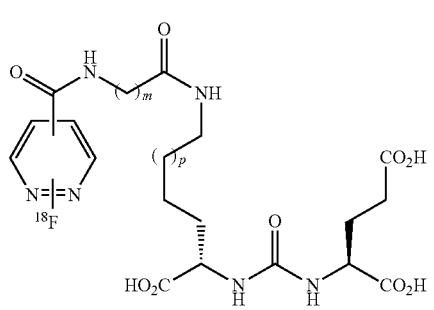
(Ih)
wherein m is an integer from 1 to 8; p is an integer from 0 to 2.
Also preferred is said method for preparing a compound of the formula (I) selected from the compounds of the following subformulae (I-1)-(I-6):
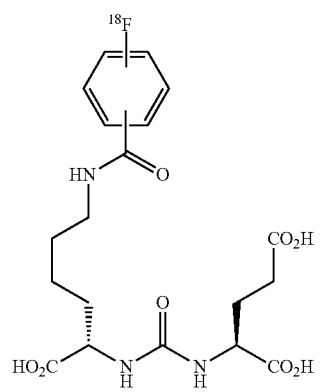
(I-1)
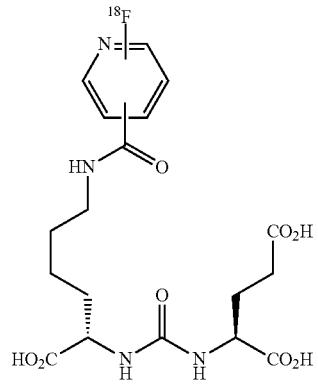
(I-2)
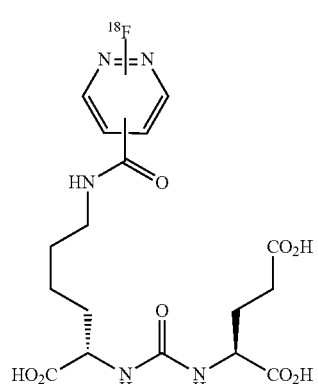
(I-3)
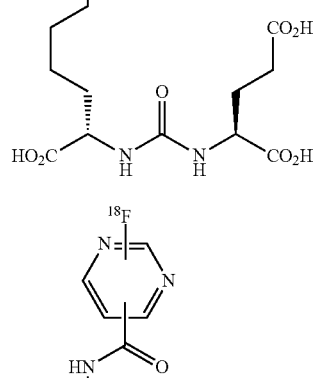
(I-4)
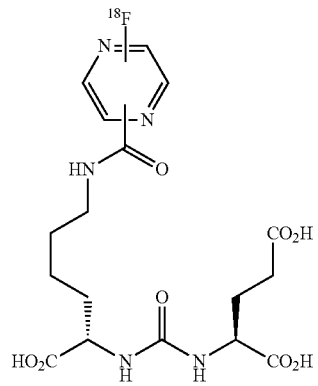
(I-5)
More preferred is said method for preparing a compound of the formula (I) selected from the compounds of the following subformulae (I-6)-(I-15):

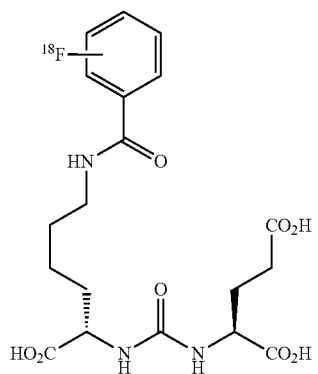
(I-6)
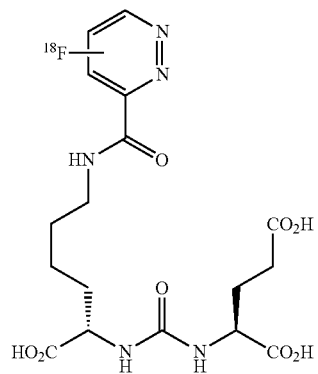
(I-10)
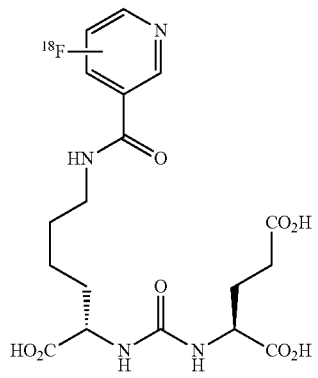
(I-7)
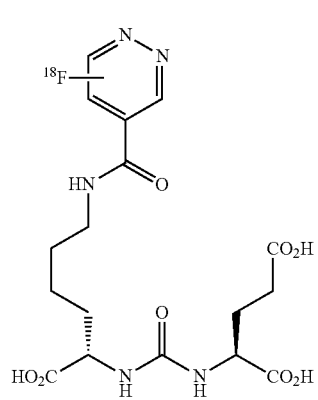
(I-11)
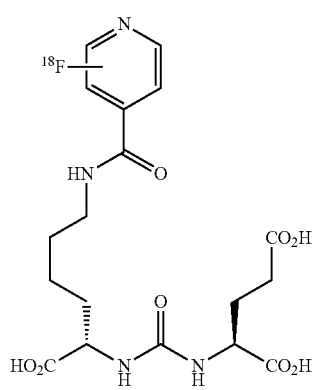
(I-8)
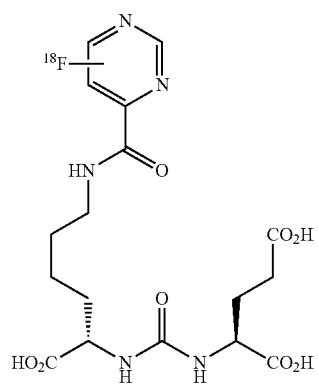
(I-12)
(I-9)
(I-13)

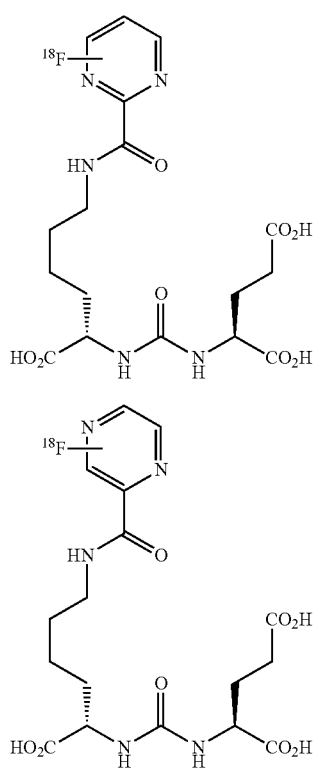
Still more preferred is said method for preparing a compound of the formula (I) selected from the following compounds 1-1-1-34.
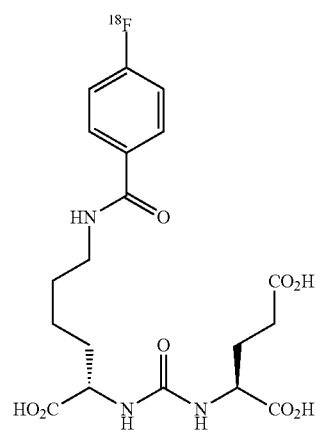
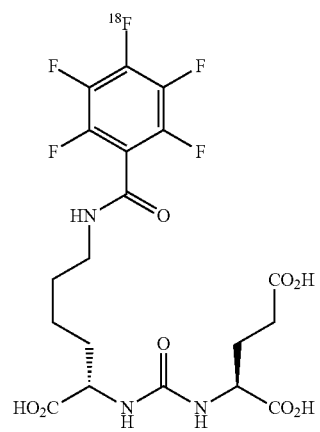
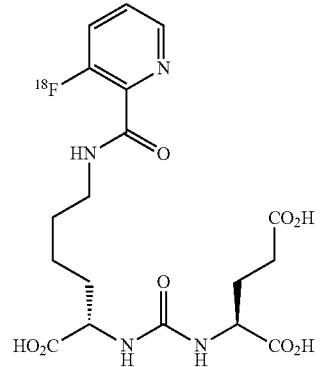
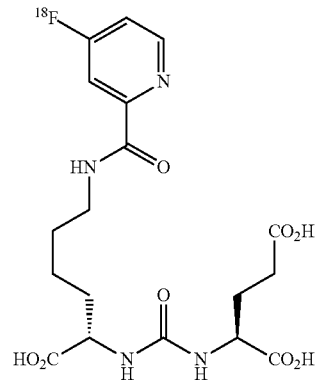

I-7
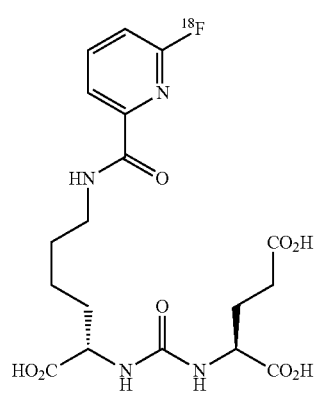
I-8
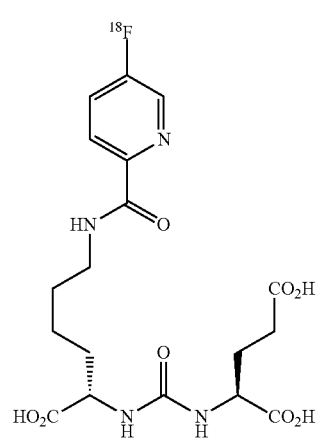
I-9
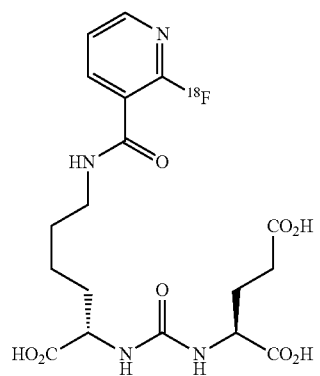
I-10
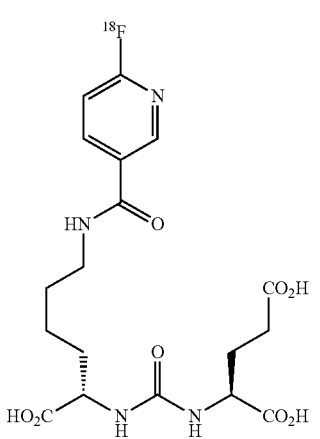
1-11
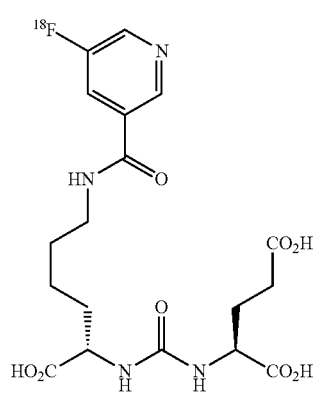
1-12
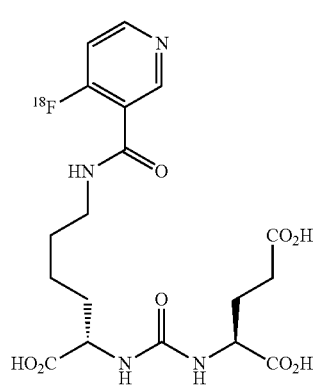
1-13
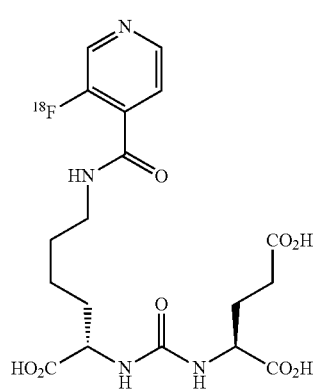
1-14
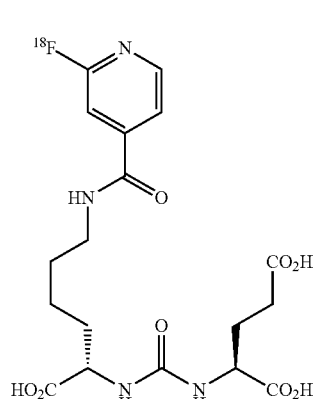

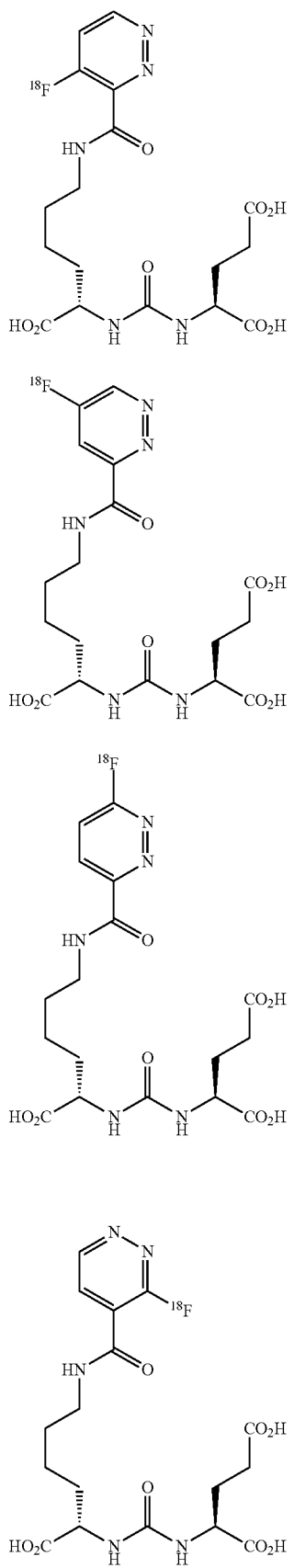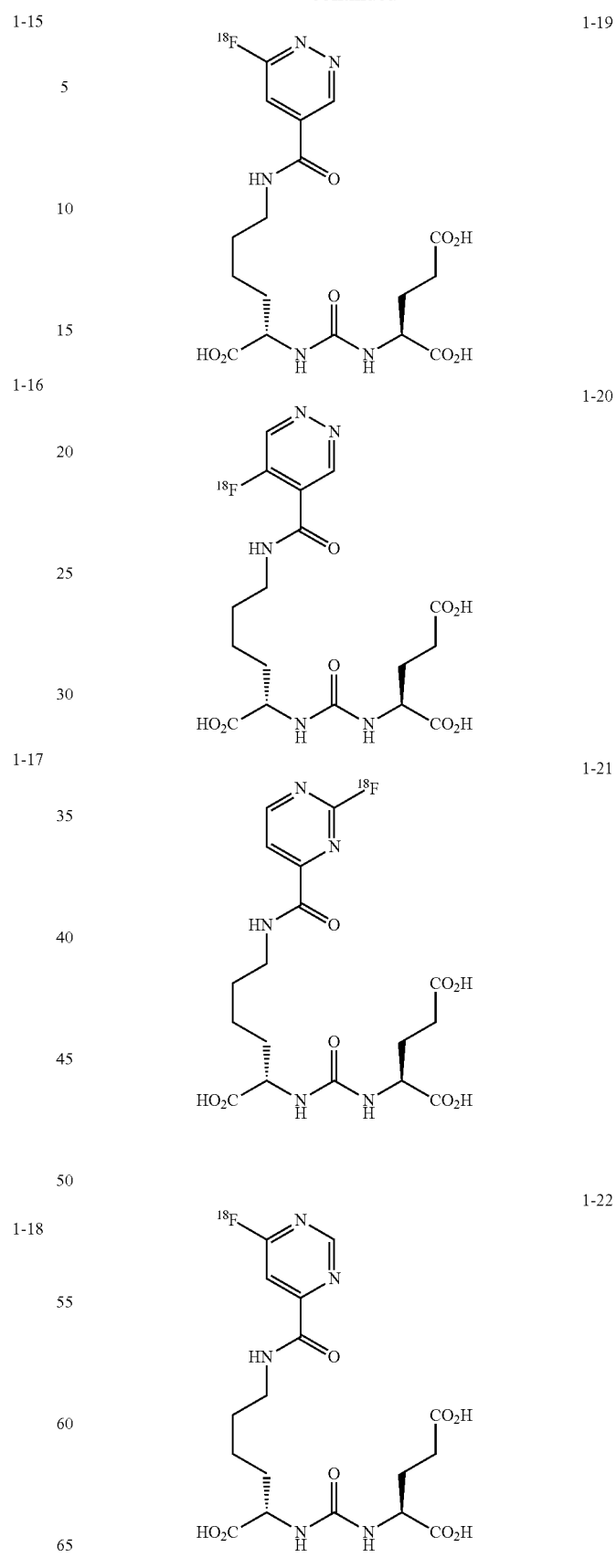

1-23
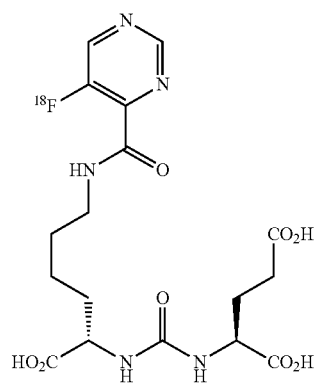
1-24
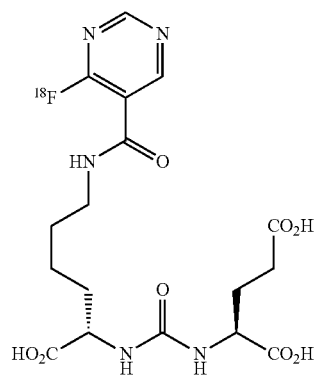
1-25
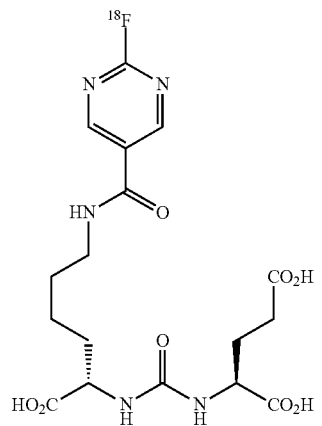
1-26
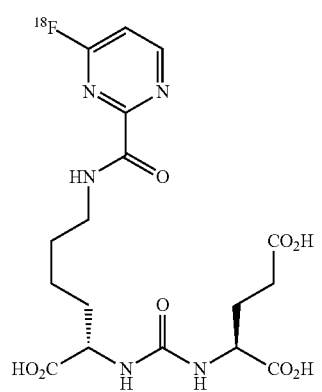
1-27
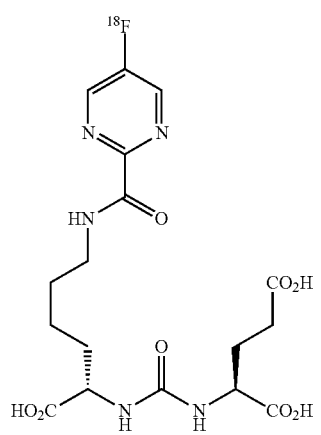
1-28
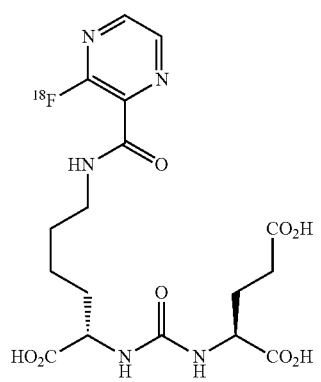
1-29
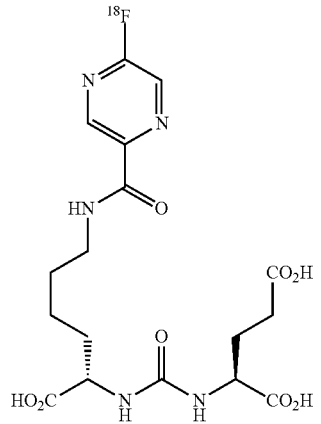
1-30
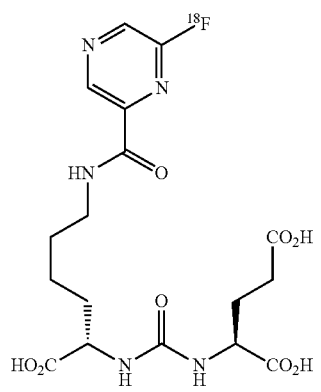

1-31
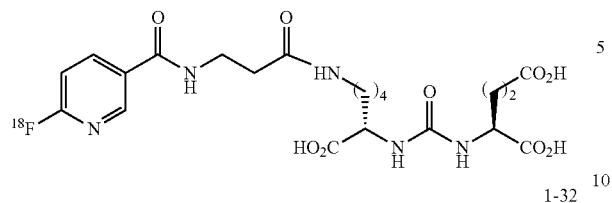
1-32
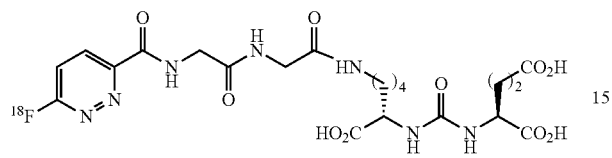
1-33
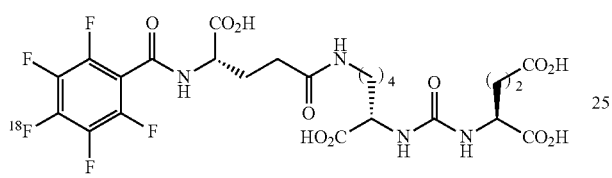
1-34
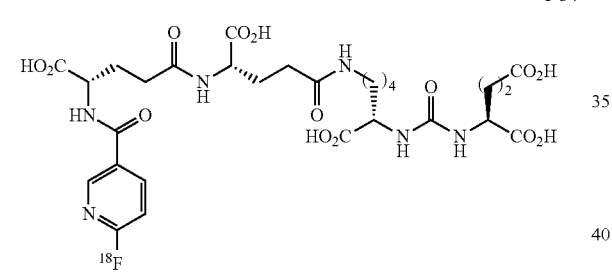
Most preferred is said method for preparing the compound of the formula (I) selected from the group consisting of compounds 1-3, 1-10, 1-14, 1-17, 1-29, 1-31, 1-32, 1-33, and 1-34:
1-3
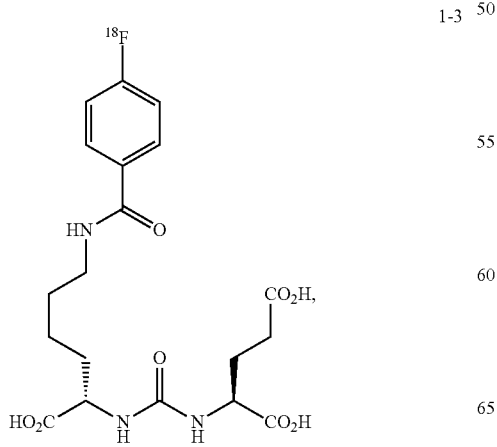
1-10
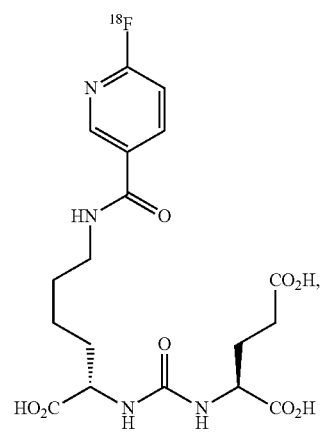
1-14
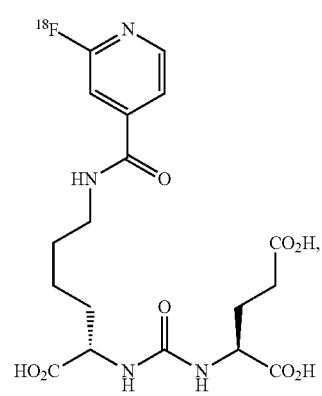
1-17
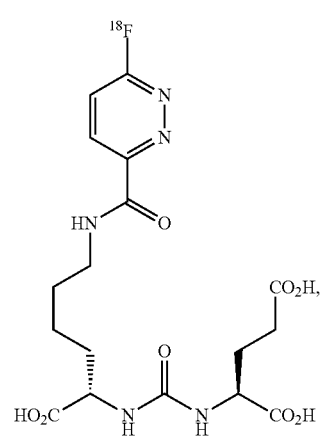

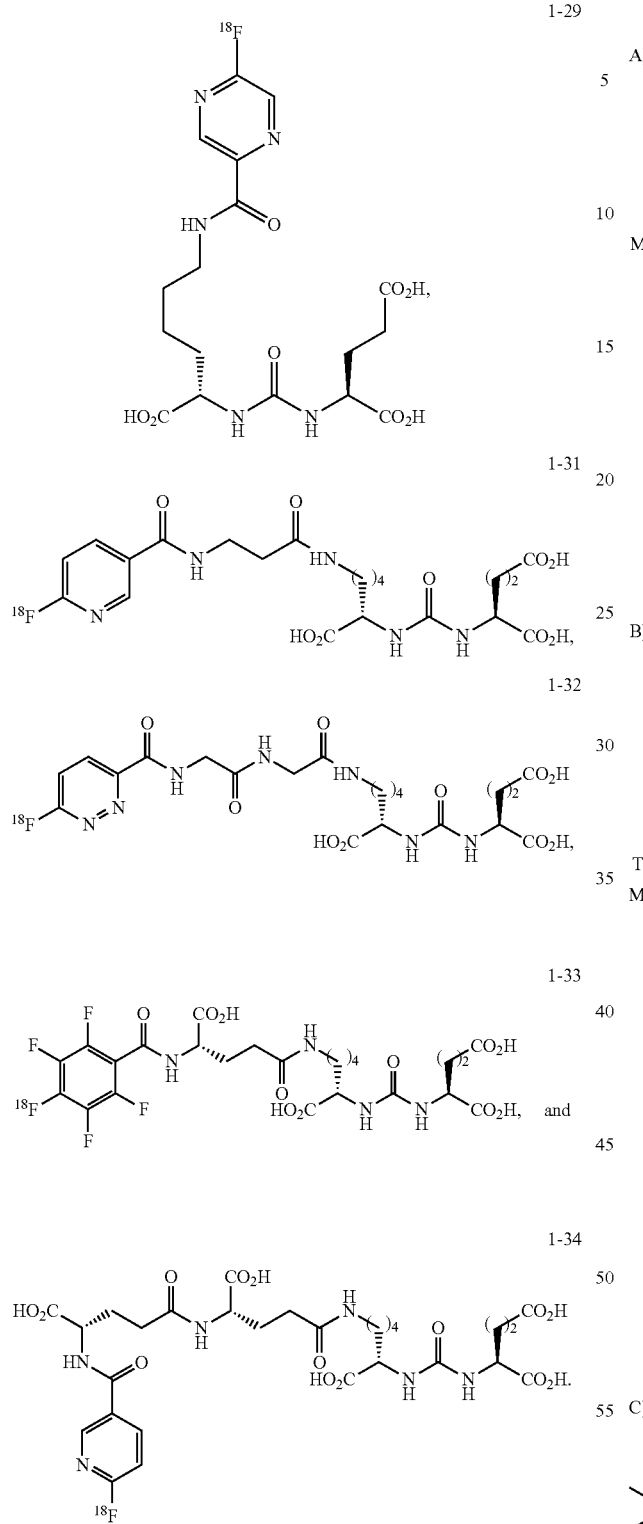
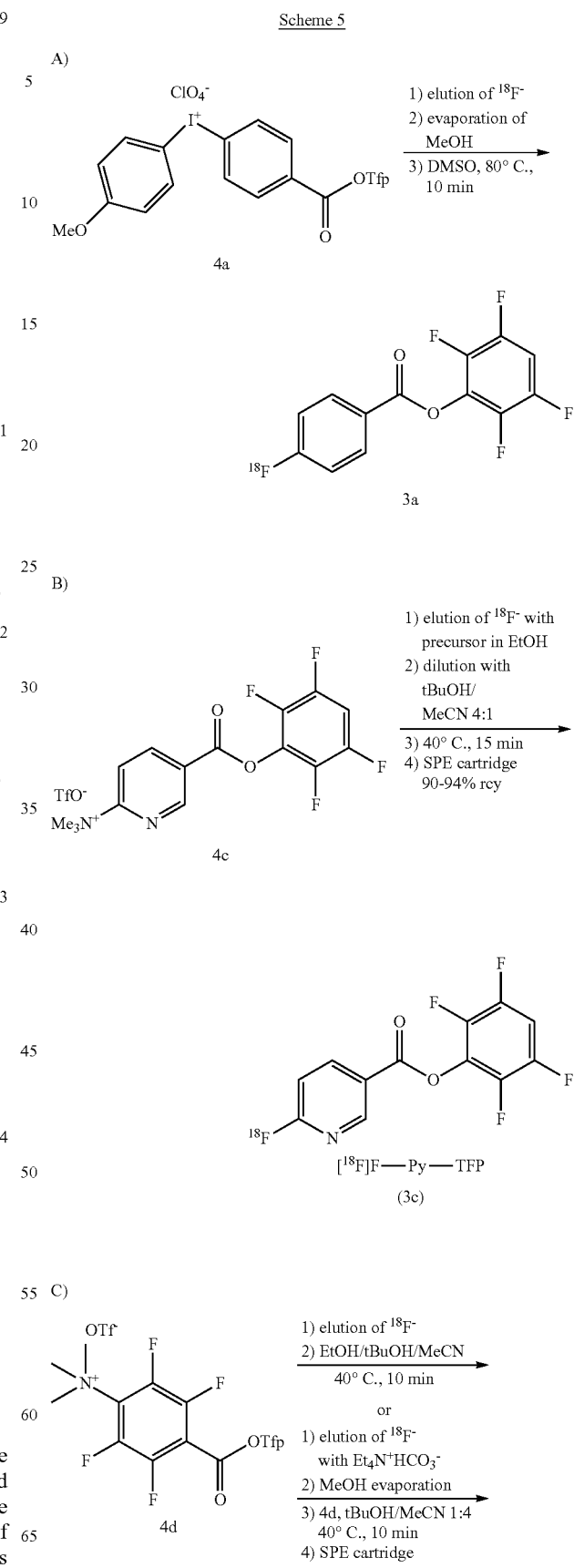
Scheme 5
The present invention refers to the compound of the formula (I) obtainable by any of the above mentioned inventive methods, preferably the compound of any of the subformulae (Ia)-(Ie) and (I-1)-(I-15) obtainable by any of said inventive methods, more preferably the compounds 1-1-1-34 obtainable by any of said inventive methods.

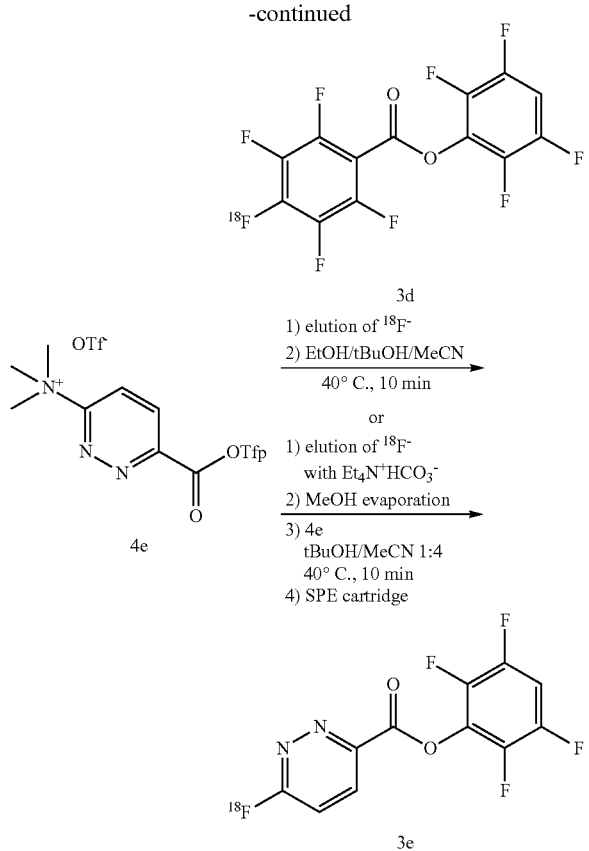

In the present invention, compound of the formula (III) as activated aromatic ester (pyridine, pyrazine, pyrimidine, tri/tetrahalo, cyano-, nitro-, (per)fluoralkyl-, like trifluoromethyl-, alkylcarboxybenzene or similar) can be prepared by $S_{N_{Ar}}$ radiofluorination of precursor compound of the formula (IV) as shown in Scheme 5.

In case of less activated precursors of the formulae IV-6 and IV-7, e.g., (4-methoxyphenyl)[4-(2,3,5,6-tetrafluorophenoxycarbonyl)phenyl]iodanium perchlorate 2,3,5,6-tetrafluorophenyl 4-(4-methoxyphenyl)phenyliodonium benzoate perchlorate (4a), the solvent should be removed under reduced pressure before the nucleophilic reaction can be carried out. The residue is taken up in a suitable solvent and subsequently heated for a short time to give the desired radiolabelled active ester as shown Scheme 5A.

In case of highly activated precursors of the formulae IV-8-IV-17, e.g. N,N,N-trimethyl-5-[(2,3,5,6-tetrafluorophenoxy)-carbonyl]pyridine-2-aminium trifluoromethanesulfonate (4c), removal of alcohol (except MeOH) is unnecessary. Accordingly, the $^{18}$F-eluate can be simply diluted with the corresponding solvent (e.g., tBuOH, tBuOH/MeCN, MeCN, etc.) and directly heated for a short time. Finally, the radiolabelled active esters are isolated using HPLC or SPE. In both cases neither azeotropic drying nor base nor any other additives are necessary (Scheme 5B). The described methods allow to prepare e. g., [$^{18}$F]TFB 3a and [$^{18}$F]F-Py-TFP 3c in 20-25% and 90-94% RCYs, respectively. Alternatively, $^{18}$F-labelled active esters from highly activated precursors can be prepared using alcoholic tetraethylammonium bicarbonate solutions (e.g., in nPrOH, iPrOH, nBuOH, better in EtOH or MeOH) for $^{18}$F$^{-}$ elution. The eluate is concentrated under reduced pressure. Precursor for radiolabelling in a suitable solvent (e.g., tBuOH, tBuOH/ MeCN, MeCN, etc.) is added and the reaction mixture is heated for a short time to give the respective active ester in more than 90% RCY. The building block is isolated via RP-SPE in excellent radiochemical and chemical purity (Scheme 5C).

The present invention relates also to a kit comprising a container containing the compound of formula (II) and/or (III) as defined above for the preparation of PET contrast media. In certain embodiments, the kit provides packaged pharmaceutical compositions comprising a pharmaceutically acceptable carrier and a compound of the invention. In certain embodiments the packaged pharmaceutical composition will comprise the reaction precursors necessary to generate the compound of the invention upon combination with a radiolabeled precursor. Other packaged pharmaceutical compositions provided by the present invention further comprise indicia comprising at least one of: instructions for preparing compounds according to the invention from supplied precursors, instructions for using the composition to image cells or tissues expressing PSMA, or instructions for using the composition to image glutamatergic neurotransmission in a patient suffering from a stress-related disorder, or instructions for using the composition to image prostate cancer.

The present invention relates also to a device for the preparation of the active compounds referred to above, wherein the device comprises suitable containers comprising any of the herein disclosed compounds, e.g. compounds according to formula (II) and/or (III). In one embodiment, the device is suitable for synthesis of, e.g. [$^{18}$F]DCFPyL 1-10 starting from [$^{18}$F]fluoride, preferably without HPLC purification. In one embodiment the device is an automated cassette module that is suitable for synthesis of, e.g. [$^{18}$F] DCFPyL 1-10 starting from [$^{18}$F]fluoride, preferably without HPLC purification, e.g. as shown in FIG. 4.

Application of the Radiolabelled Active Esters (III) for the Preparation of PET Tracers An application of the $^{18}$F-labelled active esters synthesized according to the inventive procedures is exemplified by the simplified preparation of the PSMA-specific tracer [$^{18}$F]DCFPyL 1-10.

According to the inventive method, [$^{18}$F]F-Py-TFP 3c obtained under "nothing added conditions" was eluted from the resin with ethanol in a solution of HO-Lys-C(O)-Glu-OH 2b and tetraethylammonium bicarbonate in ethanol (Scheme 6). The reaction mixture was heated at 40° C. for 3 min. [$^{18}$F]DCFPyL 1-10 was isolated by RP-HPLC using 10% ethanol in isotonic saline as an eluent to give after sterile filtration the ready to use solution of the radiotracer.

Scheme 6: The novel method for the preparation of [$^{18}$F]DCFPyL 1-10.

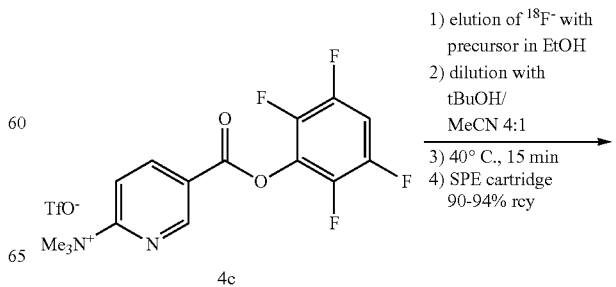

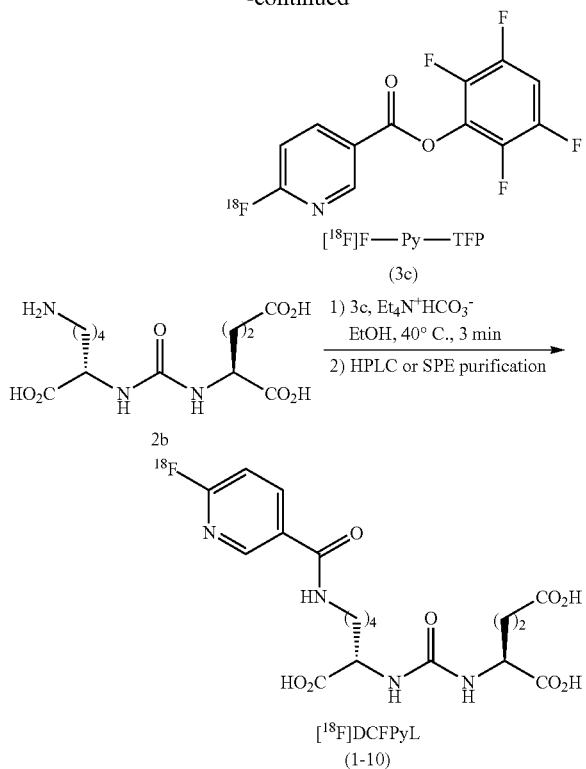

In the inventive method $^{18}F^-$ is trapped on an anion exchange resin and then eluted directly with an alcoholic solution of the radiolabelling precursor containing an onium group (X) like $R^2_3N^+$, $ArI^+$ or $Ar_2S^+$. The solvent is removed under reduced pressure; the residue is taken up in a suitable solvent and heated for a short time. In case of highly activated radiolabelling precursors such as the precursor of [$^{18}F$]F-Py-TFP 3c solvent removal is unnecessary. In this case an alcoholic solution (except MeOH) of the onium [$^{18}F$]fluoride salt is simply diluted with a suitable solvent and heated. The purification/isolation of the radiolabelled active esters is accomplished by SPE or HPLC purification. Neither azeotropic drying nor a base nor any other ingredients are needed. Alternatively, elution of radiofluoride can be accomplished with tetraethylammonium bicarbonate (TEABC) in MeOH. In this case neither azeotropic drying nor any other ingredients are needed.

The inventive modifications of the common radiofluorination procedure allow a considerable shortening of the overall preparation time, due to the reduction of a number of preparation steps. Additionally radiofluorination according to Methods 1 and 2 is carried out under base free conditions that enables one step preparation of the $^{18}F$-labelled active esters even from less activated labelling precursors where harsher reaction conditions (higher temperatures, longer reaction times) are necessary. These advantages allow to carry out the radiosynthesis in one pot making the inventive methods well-suited for automated radiosyntheses, especially in microfluidic devices.

In contrast to the published radiosynthesis of [$^{18}F$]DCFPyL 1-10 by Pomper et al. the inventive method for the preparation of this radiotracer allows to omit any evaporation steps, application of water-immiscible toxic and environmentally dangerous solvents ($CH_2Cl_2$), toxic reagents (TFA, anisole, MeCN), deprotection, HPLC purification and additional formulation steps.

The inventive method enables automatic synthesis of [$^{18}F$]DCFPyL 1-10 as shown in Example 3. Consequently, using the inventive method [$^{18}F$]DCFPyL 1-10 could be prepared faster and in higher isolated RCYs of up to 45% over 2 steps within only 55 min after end of bombardment (EOB) compared to RCYs of 35% over 3 steps within 128 min EOB. The automatic synthesis yields [$^{18}F$]DCFPyL 1-10 in isolated RCYs up to 35% in only 50 min.

Pharmaceutical Composition

Another aspect of the present invention relates to pharmaceutical compositions comprising at least one compound of formula (I) together with at least one pharmaceutically acceptable solvent, ingredient and/or diluents. Said pharmaceutical composition is useful for imaging prostate cancer cells or prostate cancerous tissue. Pharaceutically acceptable ingredient refers to especially antiviral, antibacterial or antifungal agents. Diluent includes any one of sterile saline, sodium chloride injection, Ringer's injection, dextrose injection, dextrose and sodium chloride injection, lactated Ringer's injection and other aqueous buffer solution. The amount of diluent in the composition can range from about 5 to about 95% by weight of the total composition, preferably from about 25 to about 75 weight %, and more preferably from about 30 to about 60 weight %. The inventive pharmaceutical composition may be administered by injection (intravenous, intraperitoneal, intramuscular, subcutaneous).

PET Imaging

So far the only PSMA PET tracer used in clinics is [$^{68}Ga$]HBED-CC (50). $^{68}Ga$ has a half-life of 68 min and is obtained from a generator system in only moderate amounts that precludes the broad application of [$^{68}Ga$]HBED-CC (50) in clinical practice. In contrast, $^{18}F$ has the advantage of a longer half-life (110 min) and is accessible in high amounts of up to 74 GBq or more. This permits the centralized production and regional distribution as practiced in the supply of [$^{18}F$]FDG for clinical use. In a suitable PSMA$^+$ PCa mice model [$^{18}F$]DCFPyL 1-10 displays imaging characteristics nearly identical to those of [$^{68}Ga$]HBED-CC (50). Moreover, kidney uptake of [$^{18}F$]DCFPyL 1-10 is much lower as that of [$^{68}Ga$]HBED-CC (50). This should improve the detection of tumor lesions in the abdomen. Therefore, taking into an easy accessibility of [$^{18}F$]DCFPyL 1-10 according to the present invention it could represents an adequate alternative for [$^{68}Ga$]HBED-CC (50) for research and patient care.

| | |
|---|---|
| A | 3 mL EtOH (absolute) |
| B | 200 µL [$^{18}F$]F—Py-TFP-precursor solution |
| C | 2 mL tBuOH/MeCN (4:1) |

| | |
|---|---|
| D | 10 mL H$_2$Or |
| E | 15 mL H$_2$O |
| F | 500 µL [$^{18}$F]DCFPyL-precursor solution |
| G | 3 mL H$_2$O |
| H | 10 mL H$_2$O |
| I | 60 mL 1.7% H$_3$PO$_4$ |
| J | 9 mL Isotonic NaCl |
| K | 2 mL Isotonic NaCl with 50 Vol % EtOH |
| L | 10 mL H$_2$O |
| M | 20 mL 0.1% TFA |

Figure 4:
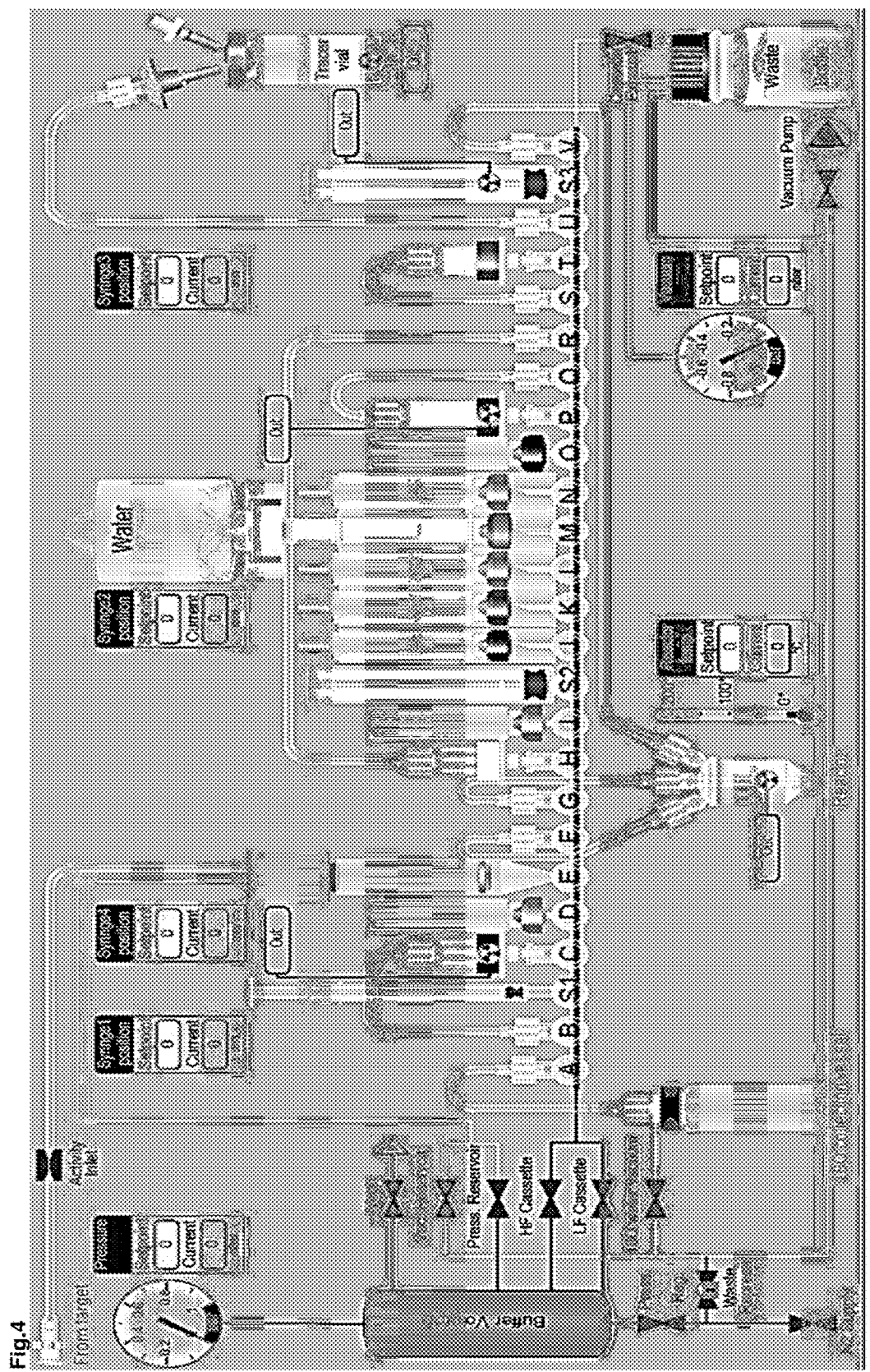

FIG. 4: Automated cassette module synthesis of [$^{18}$F]DCFPyL 1-10 starting from [$^{18}$F]fluoride without HPLC purification

EXAMPLES

Abbreviations:

βAla (beta-alanine), Boc (tert-butyloxycarbonyl), DCC (N,N'-dicyclohexylcarbodiimide), DMF (dimethylformamide), DMM (dimethoxymethane), DMSO (dimethyl sulfoxide), EDC (1-ethyl-3-(3-dimethylaminopropyl)carbodiimide), EDTA (ethylenediaminetetraacetic acid), Glu (glutamic acid), Gly (glycine), Lys or syL (lysine) mCPBA (meta-chloroperoxy benzoic acid), MeCN (acetonitrile), ONSu (N-oxy-succinimide), OTf (trifluoromethanesulfonate), Tos (tosyl), PMB (p-methoxybenzyl), Py (pyridinyl), tBu (tert-butyl), TFA (trifluoroacetic acid), TFE (tetrafluoroethyl alcohol), TFP (2,3,5,6-tetrafluorophenyl), THF (tetrahydrofuran), TIS (triisopropylsilane), TMS (trimethylsilyl).

Example 01: Preparation of 2,3,5,6-Tetrafluorophenyl-6-[$^{18}$F]fluoronicotinate ([$^{18}$F]F-Py-Tfp, 3c)

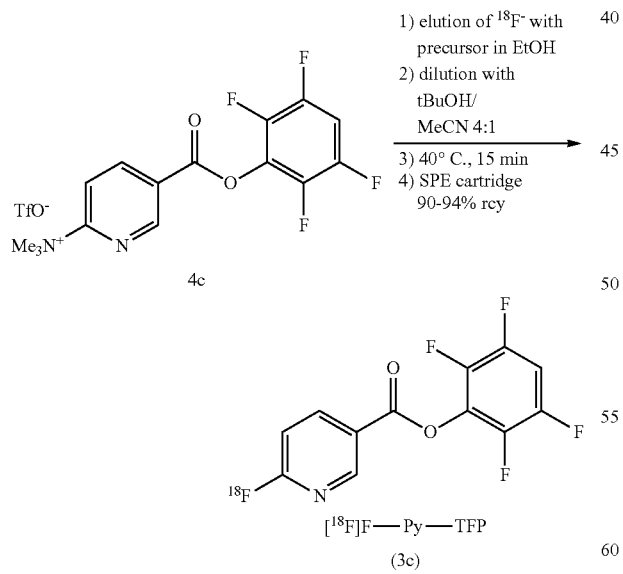

Procedure A:

Aqueous [$^{18}$F]fluoride (0.05-50 GBq) was trapped on a anion-exchange resin (QMA or Chromafix® 30-PS—HCO$_3$ cartridge). It should be noted, that in the case of QMA cartridges, the aqueous [$^{18}$F]fluoride was loaded onto the cartridge from the male side, whereas EtOH flushing and $^{18}$F$^-$ elution were done from the female side of the cartridge. The cartridge was washed with EtOH (1 mL) and [$^{18}$F]fluoride was eluted from the resin into the reaction vial with N,N,N-trimethyl-5-[(2,3,5,6-tetrafluorophenoxy)-carbonyl]pyridine-2-aminium trifluoromethanesulfonate 4c (10 mg, 20 µmoL) in EtOH (200 µL) followed by MeCN/tBuOH 1:4 (2 mL). The mixture was stirred for 15 min at 40° C. After cooling to ambient temperature, the reaction mixture was diluted with water (20 mL) and loaded onto a polymer RP cartridge (the cartridge was preconditioned with 2 mL EtOH followed by 30 mL H$_2$O). The cartridge was washed H$_2$O (5 mL) and [$^{18}$F]F-Py-Tfp 3c (up to 15 GBq, 70-75% EOB; not decay corrected) was eluted with EtOH (300 µL). The radiochemical and chemical purities after SPE purification were >98% determined by analytical HPLC (Eluent: Water with 50% MeCN. Flow rate: 1.5 mL/min. Column: Chromolith® SpeedROD RP-18e column (Merck, Darmstadt Germany), 50×4.6 mm. Retention time: [$^{18}$F]F-Py-Tfp 3c~2 min).

Procedure B:

Aqueous [$^{18}$F]fluoride (0.05-50 GBq) was trapped on a anion-exchange resin (QMA or Chromafix® 30-PS—HCO$_3$ cartridge). It should be noted, that in the case of QMA cartridges, the aqueous [$^{18}$F]fluoride was loaded onto the cartridge from the male side, whereas EtOH flushing and $^{18}$F$^-$ elution were done from the female side of the cartridge. [$^{18}$F]fluoride was eluted from the resin into the reaction vial with methanolic tetraethylammonium bicarbonate solution (5 mg, 500 µL). The solvent was removed under reduced pressure at 70 C within 2 min. Afterwards precursor dissolved in MeCN/tBuOH 1:4 (2 mL) was added and the mixture was stirred for 15 min at 40° C. After cooling to ambient temperature, the reaction mixture was diluted with water (20 mL) and loaded onto a polymer RP cartridge (the cartridge was preconditioned with 2 mL EtOH followed by 30 mL H$_2$O). The cartridge was washed H$_2$O (5 mL) and [$^{18}$F]F-Py-Tfp 3c (up to 15 GBq, 70-75% EOB; not decay corrected) was eluted with EtOH (300 µL). The radiochemical and chemical purities after SPE purification were >98% determined by analytical HPLC (Eluent: Water with 50% MeCN. Flow rate: 1.5 mL/min. Column: Chromolith® SpeedROD RP-18e column (Merck, Darmstadt Germany), 50×4.6 mm. Retention time: [$^{18}$F]F-Py-Tfp 3c~2 min).

Example 02: Preparation of [$^{18}$F]DCFPyL 1-10

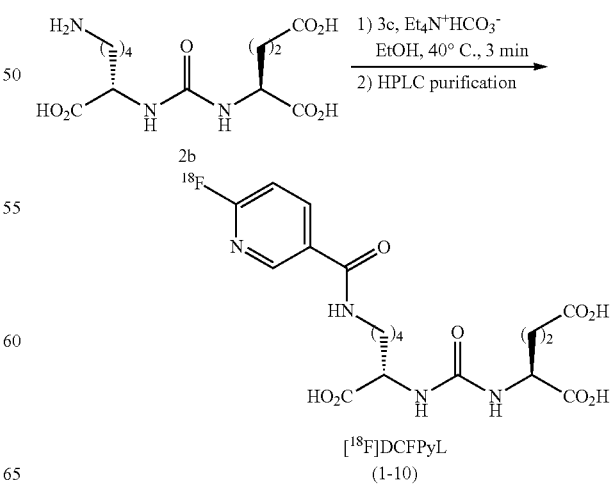

To a freshly prepared ethanolic solution of HO-Lys-C(O)-Glu-OH 2b (2.5 mg, 100 μL) and tetraethylammonium bicarbonate (0.5 M) in EtOH (60 μL) an ethanolic solution of [$^{18}$F]F-Py-Tfp 3c (0.05-10 GBq in 150 μL) was added. The reaction mixture was stirred for 3 min at 40° C. Afterwards the mixture was quenched with water (2 mL) and purified by preparative HPLC. Eluent: saline (0.9% NaCl) with 10% EtOH. Flow rate: 8 mL/min. Column: Synergi 4 μm Hydro-RP 80 Å 100×21.2 mm. Retention time: ~7 min. The purified product was sterile filtered before use. [$^{18}$F]DCFPyL 1-10 was obtained in 75-90% RCY (decay-corrected). The radiochemical and chemical purities after HPLC purification were >98%, determined by analytical HPLC: Eluent: phosphoric acid buffer solution (pH=2) with 10% EtOH for 5 min, then 50% for 2 min. Flow rate: 1.5 mL/min. Column: Chromolith® SpeedROD RP-18e column (Merck, Darmstadt Germany), 50×4.6 mm. Retention times: [$^{18}$F]DCFPyL~3 min; [$^{18}$F]F-Py-Tfp~5.7 min).

Figure 1:
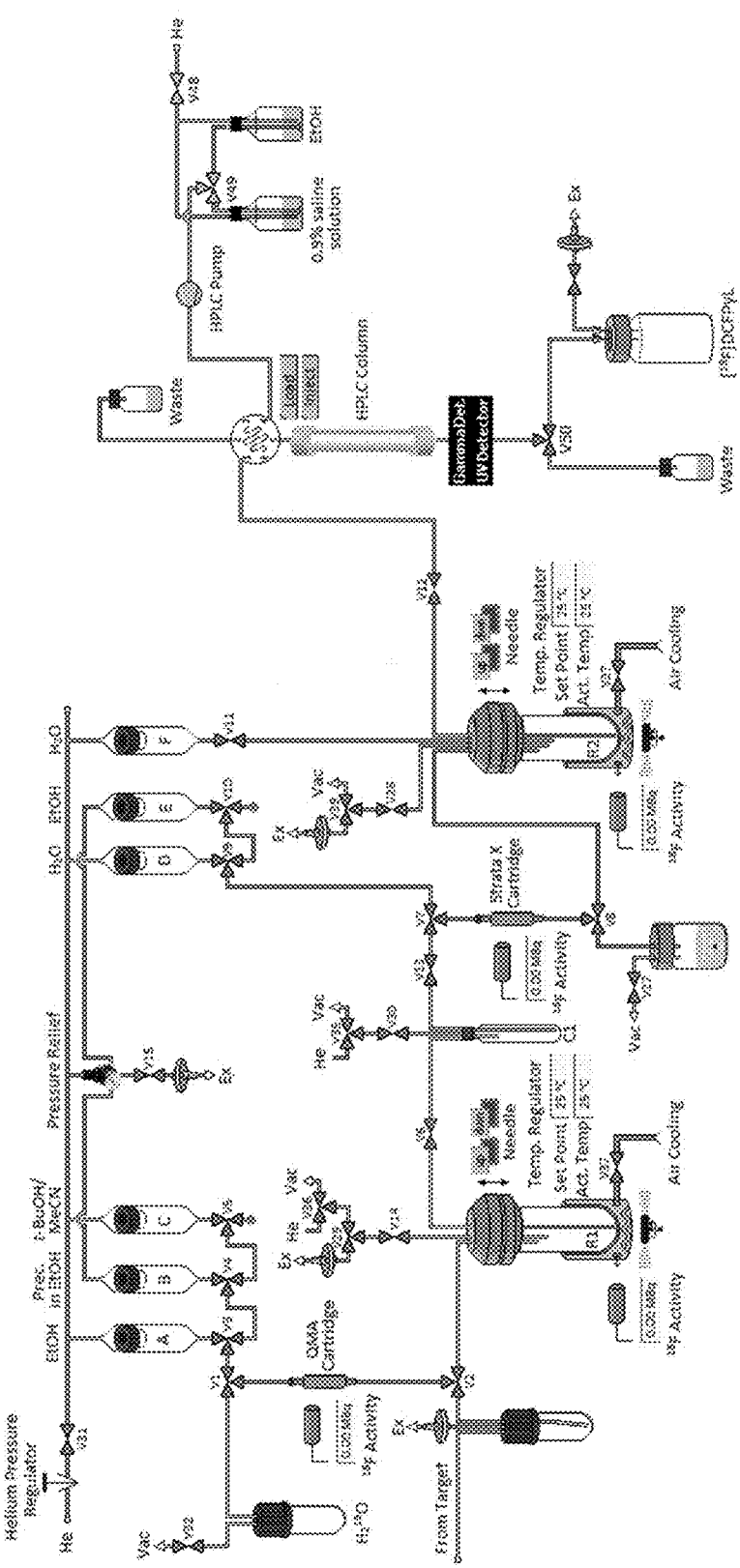
FIG. 1: Automatic synthesis of [$^{18}F$]DCFPyL with HPLC purification in a TRACERLab FX$_{fn}$ automated radiochemistry synthesis module (GE Medical Systems).

Example 03: Automated Synthesis of [$^{18}$F]DCFPyL 1-10 Starting from [$^{18}$F]Fluoride Using Final HPLC Purification (FIG. 1)

Aqueous [$^{18}$F]fluoride (0.05-50 GBq) was vacuum-transferred from the target to a trapping vial. Aqueous [$^{18}$F] fluoride was then transferred from the trapping vial through an anion-exchange resin cartridge (QMA) from the male side of the cartridge, and [$^{18}$O]H$_2$O was collected in a separate vial. The cartridge was subsequently washed with EtOH (1 mL) from vial A from the female side of the cartridge. Washings were discarded. Thereafter, [$^{18}$F]fluoride was eluted from the resin with N,N,N-trimethyl-5-[(2,3,5,6-tetrafluorophenoxy)-carbonyl]pyridine-2-aminium trifluoromethanesulfonate 4c (10 mg, 20 μmoL) in EtOH (200 μL) from vial B into reactor R1. After this, MeCN/tBuOH 1:4 (2 mL) from vessel C was passed through the cartridge into reactor R1. Reactor R1 was filled with helium, sealed and the reaction mixture was heated at 45° C. for 20 min. After cooling to room temperature the crude [$^{18}$F]F-Py-Tfp 3c was transferred into the collecting vial C1, containing 20 mL H$_2$O. The solution was passed through a polymer RP cartridge (Strata X). The cartridge was washed with H$_2$O (5 mL) from reservoir D and dried by applying a helium stream for 5 min. [$^{18}$F]F-Py-Tfp 3c was eluted with EtOH (400 μL) from vial E into reactor R2 containing a mixture of a freshly prepared ethanolic solution of HO-syL-C(O)-Glu-OH 2b (2.5 mg, 100 μL) and 0.5 M tetraethylammonium bicarbonate in EtOH (60 μL). After addition of [$^{18}$F]F-Py-Tfp, the reaction mixture was heated at 40° C. for 3 min. After cooling to room temperature the reaction mixture was diluted with H$_2$O (2 mL) from vial F and [$^{18}$F]DCFPyL was loaded onto the HPLC for purification. The crude tracer was purified by preparative HPLC to give [$^{18}$F]DCFPyL 1-10 in 40-65% RCY (from $^{18}$F$^-$; decay-corrected) in ≥95% radiochemical purity. Eluent: saline (0.9% NaCl) with 10% EtOH. Flow rate: 8 mL/min. Column: Synergi 4 am Hydro-RP 80 Å 100×21.2 mm. Retention time: ~7 min. The purified product was sterile filtered before use as (determined by analytical HPLC (Quality control): Eluent: phosphoric acid buffer solution (pH=2) with 10% EtOH for 5 min, then phosphoric acid buffer solution (pH=2) with 50% EtOH for 2 min. Flow rate: 1.5 mL/min. Column: Chromolith® SpeedROD RP-18e column (Merck, Darmstadt Germany), 50×4.6 mm. Retention times: [$^{18}$F]DCFPyL~3 min; [$^{18}$F]F-Py-Tfp~5.7 min).

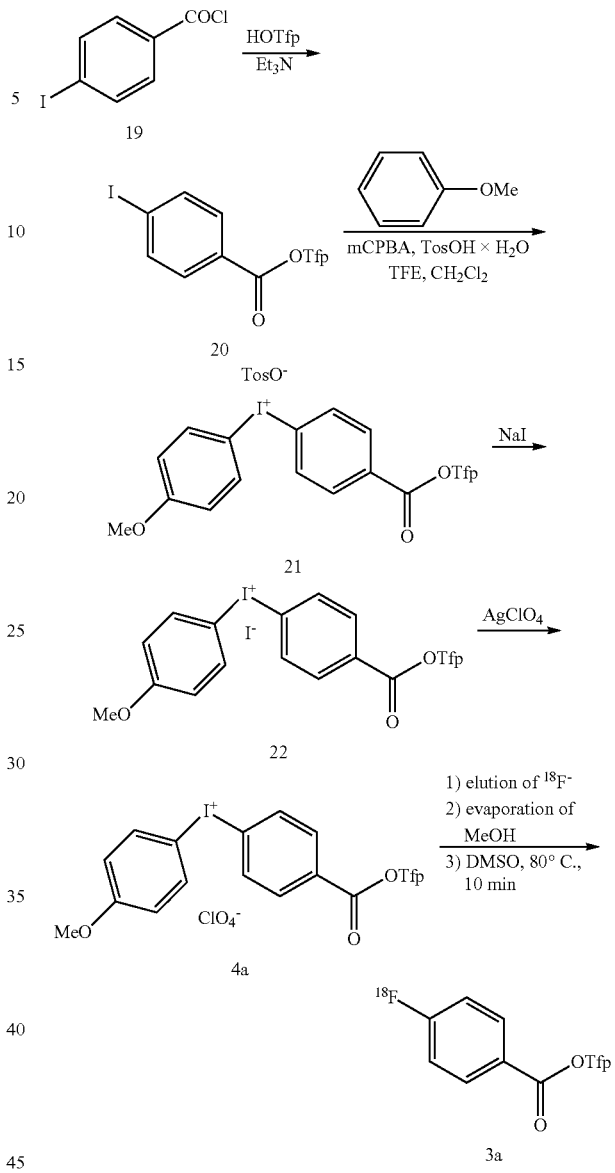

Example 04: Preparation of 2,3,5,6-Tetrafluorophenyl 4-Iodobenzoate 20

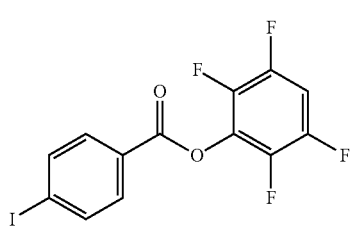

Et$_3$N (1.504 mL, 0.76 g, 7.51 mmol) was added dropwise to a vigorously stirred solution of 4-iodobenzoyl chloride 19 (2 g, 7.51 mmol) and 2,3,5,6-tetrafluorophenol (1.25 g, 7.51 mmol) in Et$_2$O (60 mL) and the stirring was continued for a further 10 min. The reaction mixture was filtered, the filter cake was washed with Et$_2$O (30 mL) and the filtrate was concentrated under reduced pressure. The residue was dissolved Et$_2$O (10 mL) and filtered. The filtrate was concentrated under reduced pressure. The residue was recrystallized from Et$_2$O/hexane to give the title compound (1.38 g, 48%) as a colorless solid.

R$_f$=0.46, EtOAc:hexane=1:10.

$^1$H-NMR (CDCl$_3$, 300 MHz): δ=7.07 (tt, J=9.9, 7.1 Hz, 1H), 7.82-7.98 (m, 4H);

$^{19}$F-NMR (CDCl$_3$, 282.4 MHz): δ=−152.70, −138.80;

$^{13}$C-NMR (CDCl$_3$, 75.5 MHz): δ=103.0, 103.4 (t, J=23.0 Hz), 126.6, 131.9, 138.3, 138.9-142.7 (m), 144.4 (dt, J=3.8, 12.1 Hz), 147.7 (dt, J=4.5, 12.1 Hz), 162.2. MS (ESI): positive mode m/z=397.3 ([M+H]$^+$). MS (EI, 70 eV): m/z (%): 395.9 [M$^+$] (3), 230.9 [C$_7$H$_4$OI$^+$] (100), 202.9 [C$_6$H$_3$I$^+$] (100), 104.0 [C$_7$H$_4$O] (10).

Example 05: Preparation of (4-Methoxyphenyl) [4-(2,3,5,6-tetrafluorophenoxycarbonyl)phenyl]iodonium tosylate 21

Tos.H$_2$O (0.72 g, 3.79 mmol) was added to a solution of 2,3,5,6-tetraphenyl 4-iodobenzoate 20 (1 g, 2.52 mmol), mCPBA [1.44 g, 85% purity, 7.09 mmol; commercially available 77% mCPBA (Aldrich) was dried at 2 mbar and 40° C. for 3 h before use] and anisole (0.51 mL, 0.51 g, 4.72 mmol) in 50% CF$_3$CH$_2$OH (TFE) in CH$_2$Cl$_2$ (20 mL) and the mixture was stirred for 3 days. The reaction mixture was added to vigorously stirred Et$_2$O (450 mL) and stirring was continued for a further 45 min. The precipitate was filtered off and washed with Et$_2$O (100 mL), redissolved in CH$_2$Cl$_2$ (20 mL) and filtered through Celite®. The filtrate was concentrated under reduced pressure. The residue was recrystallized from CH$_2$Cl$_2$/Et$_2$O to give the title compound (1.53 g, 90%) as a colorless solid.

$^1$H-NMR (CDCl$_3$, 300 MHz): δ=2.28 (s, 3H), 3.77 (s, 3H), 6.80 (d, J=9.0 Hz, 2H), 6.97 (d, J=6.0 Hz, 2H), 7.01-7.14 (m, 1H), 7.36 (d, J=9.0 Hz, 2H), 7.98-8.03 (m, 4H), 8.18 (d, J=9.0 Hz, 2H);

$^{19}$F-NMR (CDCl$_3$, 282.4 MHz): δ=−152.70, −138.55;

$^{13}$C-NMR (CDCl$_3$, 75.5 MHz): δ=21.2, 55.5, 103.7 (t, J=23.0 Hz), 104.7, 117.4, 123.0, 125.9, 128.5, 129.3, 132.7, 135.3, 137.9, 138.8-423142.3 (m), 139.6, 142.2, 144.4 (dt, J=3.8, 15.9 Hz), 147.7 (dt, J=4.5, 16.6 Hz), 161.3, 162.4.

MS (ESI): positive mode m/z=503.0 ([M]+); MS (ESI): negative mode m/z=171.0 ([C$_7$H$_7$SO$_3$]$^−$); ESI HRMS: calcd for C$_{20}$H$_{12}$F$_4$O$_3$I$^+$: 502.9762; found: 502.9769.

Example 06: Preparation of (4-Methoxyphenyl) [4-(2,3,5,6-tetrafluorophenoxycarbonyl)phenyl]iodonium iodide 22

(4-Methoxyphenyl)[4-(2,3,5,6-tetrafluorophenoxycarbonyl)phenyl]iodonium tosylate 21 (1.19 g, 1.76 mmol) was dissolved in CH$_2$Cl$_2$ (20 mL). After addition of saturated NaI (10 mL), the mixture was vigorously stirred for 15 min and centrifuged (4000 rpm, 15° C., 10 min). The aqueous solution and precipitate were separated off, saturated NaI (10 mL) was added and the mixture was vigorously stirred for 15 min and centrifuged (×3). The organic fraction was filtered, dried and concentrated under reduced pressure. The residue was recrystallized from CH$_2$Cl$_2$/Et$_2$O, the precipitate was filtered off, washed with acetone (10 mL) and Et$_2$O (80 mL) to give the title compound (0.29 g, 26%) as an off-white solid. The substance could be stored at 4° C. under argon at least for 4 months. However, it was unstable in solution especially at elevated temperatures (dissolved in DMF or DMSO it was unstable already at ambient temperature).

$^1$H-NMR (CDCl$_3$, 300 MHz): δ=3.79 (s, 3H), 6.65-6.73 (m, 2H), 6.95-7.10 (m, 1H), 7.56 (d, J=8.9 Hz, 2H), 7.81-8.05 (m, 3H), 8.21-8.35 (m, 1H);

$^{19}$F-NMR (CDCl$_3$, 282.4 MHz): δ=−152.63, −138.72;

$^{13}$C-NMR (CDCl$_3$, 75.5 MHz): δ=55.5, 82.3, 103.0, 103.5 (t, J=22.6 Hz), 116.4, 126.6, 128.8, 131.9, 138.3, 138.6-142.5 (m), 144.2-144.7 (m), 144.5-144.9 (m), 159.5, 162.2.

MS (ESI): positive mode m/z=502.9 ([M]+); MS (ESI): negative mode m/z=126.9 ([I]$^−$);

ESI HRMS: calcd for C$_{20}$H$_{12}$F$_4$O$_3$+: 502.9762; found: 502.9741.

Example 07: Preparation of (4-Methoxyphenyl) [4-(2,3,5,6-tetrafluorophenoxycarbonyl)phenyl]iodonium perchlorate 4a To a solution of (4-methoxyphenyl)[4-(2,3,5,6-tetrafluorophenoxycarbonyl)phenyl]-iodonium iodide 22 (0.2 g, 0.32 mmol) in acetone (12 mL) and AgClO$_4$ (66 mg, 0.32 mmol) was added. The reaction mixture was shaken for 1 min, precipitated AgI was separated by centrifugation. The supernatant was concentrated under reduced pressure and the residue was recrystallized from CH$_2$Cl$_2$/Et$_2$O to give the title compound (168 mg, 88%) as a colorless solid.

$^1$H-NMR (CDCl$_3$, 300 MHz): δ=3.80 (s, 3H), 6.88-6.98 (m, 2H), 7.06 (tt, J=9.9, 7.1 Hz, 1H), 8.04-8.13 (m, 2H), 8.14-8.18 (m, 2H), 8.21-8.26 (m, 2H);

$^{19}$F-NMR (CDCl$_3$, 282.4 MHz): δ=−152.52, −138.48;

$^{13}$C-NMR (CDCl$_3$, 75.5 MHz): δ=55.5, 101.1, 103.8 (t, J=21.1 Hz), 118.4, 120.1, 130.6, 133.5, 135.1, 138.3, 138.7-139.3 (m), 142.1-144.4 (m), 147.5-147.7 (m), 161.0, 163.4.

MS (ESI): positive mode m/z=503.0 ([M]$^+$); ESI HRMS: calcd for C$_{20}$H$_{12}$F$_4$O$_3$I$^+$: 502.9762; found: 502.9769. MS (ESI): positive mode m/z=503.0 ([M]$^+$); MS (ESI): negative mode m/z=171.0 ([C$_7$H$_7$SO$_3$]$^−$); ESI HRMS: calcd for C$_{20}$H$_{12}$F$_4$O$_3$I$^+$: 502.9762; found: 502.9749.

Example 08: Preparation of 2,3,5,6-tetrafluorophenyl 4-fluorobenzoate 24

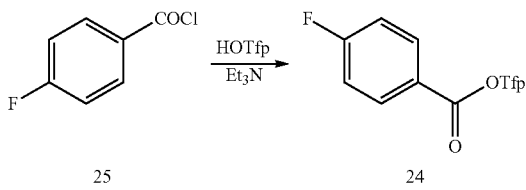

Et$_3$N (0.54 mL, 0.39 g, 3.87 mmol) was added dropwise to a vigorously stirred solution of 4-fluorobenzoyl chloride 25 (0.46 mL, 0.61 g, 3.87 mmol) and 2,3,5,6-tetrafluorophenol (0.64 g, 3.87 mmol) in Et$_2$O (30 mL) and the stirring was continued for a further 10 min. The reaction mixture was filtered, washed with H$_2$O (15 mL) and brine (2×10 mL), dried and concentrated under reduced pressure. The residue was recrystallized from hexane to give 24 (0.41 g) as a colorless solid. The mother liquor was concentrated under reduced pressure and the residue was recrystallized from hexane to give a second crop of 24 (0.45 g, total 77%).

R$_f$=0.62, EtOAc:hexane=1:10.

$^1$H-NMR (CDCl$_3$, 300 MHz): δ=7.07 (tt, J=9.9, 7.1 Hz, 1H), 7.21-7.30 (m, 2H), 8.21-8.37 (m, 2H);

$^{19}$F-NMR(CDCl$_3$, 282.4 MHz): δ=−152.75, −138.93, −102.24;

$^{13}$C-NMR (CDCl$_3$, 75.5 MHz): δ=103.4 (t, J=21.9 Hz), 116.2 (d, J=21.9 Hz), 123.5 (d, J=1.5 Hz), 133.5 (d, J=2.3 Hz), 139.0-142.7 (m), 144.5-145.1 (m), 147.3-148.2 (m), 163.3 (d, J=259.7 Hz), 168.5. MS (ESI): positive mode m/z=288.3 ([M]+). MS (EI, 70 eV): m/z (%): 165.0 [C$_6$HF$_4$O$^+$] (10), 123.0 [C$_6$H$_4$FO$^+$] (100), 95.0 [C$_6$H$_4$F$^+$] (10).

Example 09: Preparation of 2,3,5,6-tetrafluorophenyl 4-[$^{18}$F]fluorobenzoate 3a Aqueous [$^{18}$F]fluoride (0.05-50 GBq) was trapped on a anion-exchange resin (QMA or Chromafix® 30-PS—HCO$_3$ cartridge). It should be noted, that in the case of QMA cartridges, the aqueous [$^{18}$F]fluoride was loaded onto the cartridge from the male side, whereas MeOH flushing and $^{18}$F-elution was done from the female side of the cartridge. If the QMA cartridge has been loaded, flushed and eluted from the female side only, sometimes a significant amount of [$^{18}$F]fluoride remained on the resin (this is probably because QMA-light (46 mg) cartridges have a single frit on the male side but four on the female side). The cartridge was washed with MeOH (1 mL) and [$^{18}$F]fluoride was eluted into a reaction vial with a solution of (4-methoxyphenyl)[4-(2,3,5,6-tetrafluorophenoxycarbonyl)phenyl]iodonium perchlorate (5 mg) 4a in MeOH (0.5 mL). Methanol was evaporated under reduced pressure at 70° C. within 2-3 min. After cooling to room temperature DMSO (500 VL) was added. The reaction mixture was stirred at 130° C. for 10 min. Subsequently the mixture was cooled down to room temperature, water (4 mL) was added and the reaction mixture was shaken vigorously for 30 s. Analysis of the mixture by radio-HPLC showed formation of the desired $^{18}$F-labelled active ester in 24% RCY. HPLC conditions: column: Chromolith® SpeedROD RP-18e (Merck, Darmstadt Germany), 50×4.6 mm; eluent: 50% MeCN; flow rate: 3 mL/min.

Example 10: Preparation of 2,3,5,6-tetrafluorophenyl 6-[$^{18}$F]fluoropyridazine-3-carboxylate (3e)

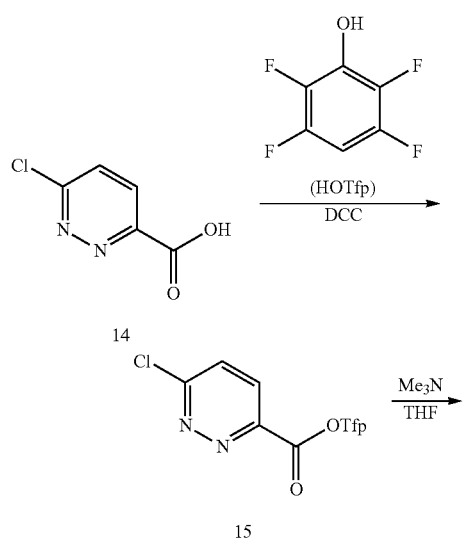

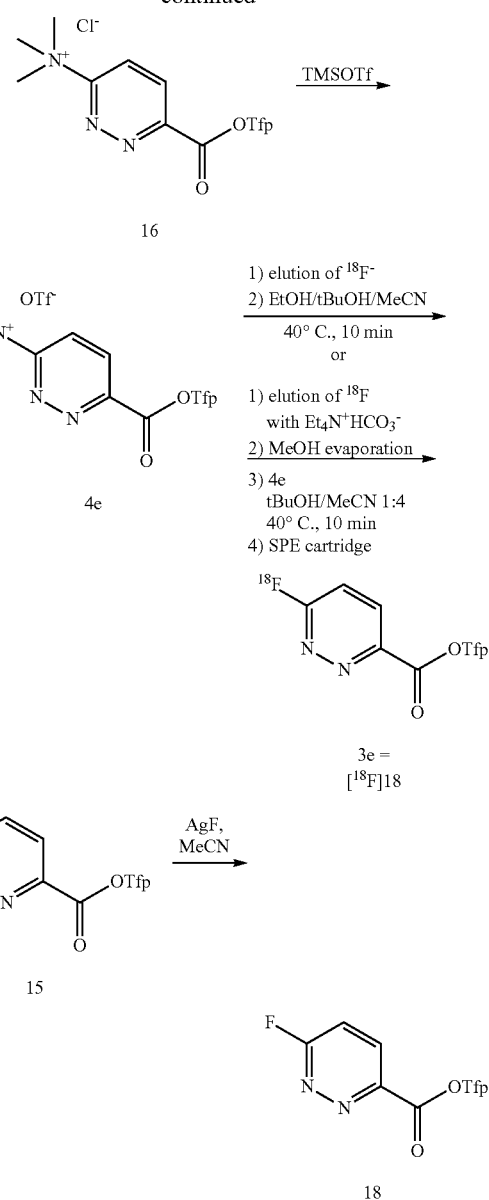

3e can be prepared from radiolabelled precursor 4e using one of two alternative radiolabelling procedures. According to the first one $^{18}$F$^−$ is fixed on an anion exchange resin. The resin is washed with EtOH and drained. $^{18}$F is eluted with an ethanolic solution of 4e. The resin is additionally washed with tBuOH/MeCN 1:4 and the collected eluates are heated for a short time. Finally 3e is isolated via SPE. Alternatively 3e is eluted with methanolic tetraethylammonium bicarbonate, the solvent is evaporated and the residue is taken up in a solution of 4e in tBuOH/MeCN 1:4 and heated for a short time. Finally the desired active ester is isolated via SPE. Radiolabelling precursor 4e can be prepared from commercially available precursor 14 as follows: Esterification with 1,2,5,6-tetrafluorophenol/DCC, treatment of the intermediate active ester 15 with anhydrous trimethylamine in THF followed by anion metathesis using TMSOTf. The reference compound 18 can be prepared from intermediate 15 by treatment with AgF under anhydrous conditions.

Example 11: Preparation 2,3,5,6-tetrafluorophenyl 5-[$^{18}$F]fluoropyrazine-2-carboxylate (3f)
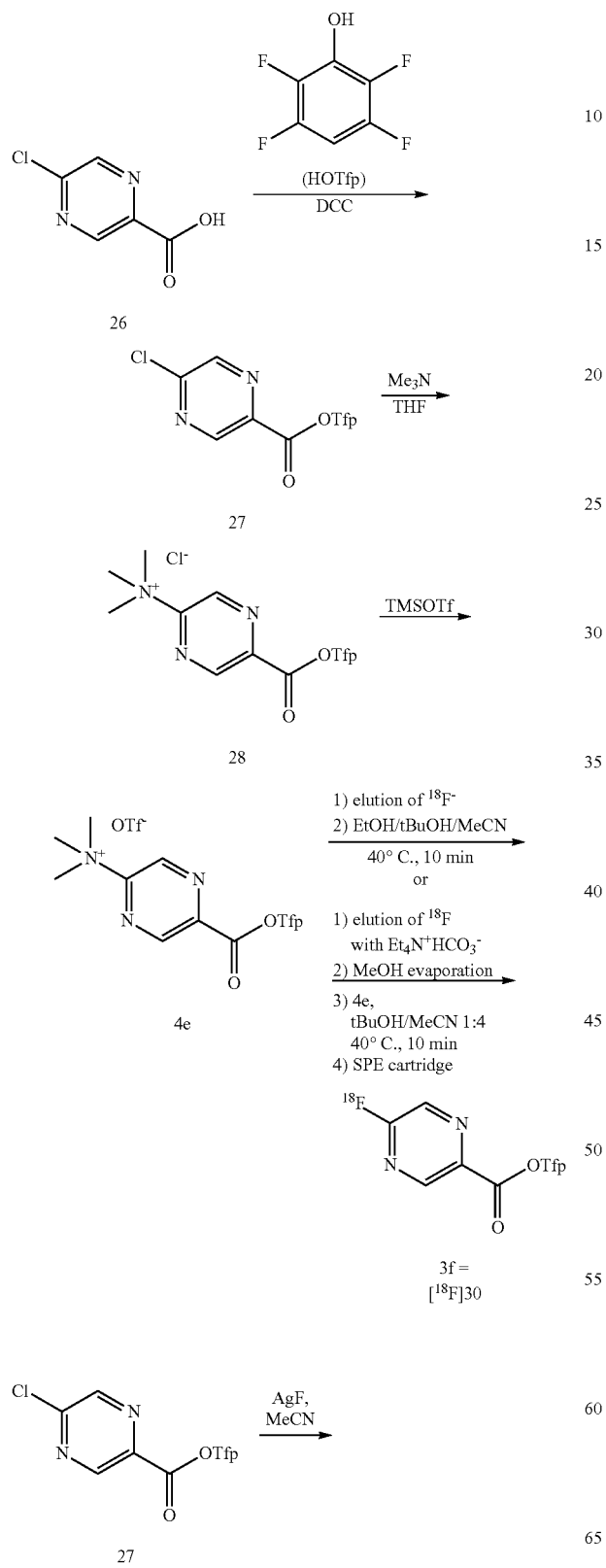
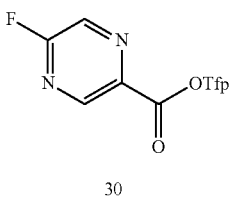
Compound 3f can be prepared exactly as 3e as described in the Example 10.
Example 12: Preparation of 2,3,5,6-tetrafluorophenyl 4-[$^{18}$F]fluoro-2,3,5,6-tetrafluorobenzoate (3d)
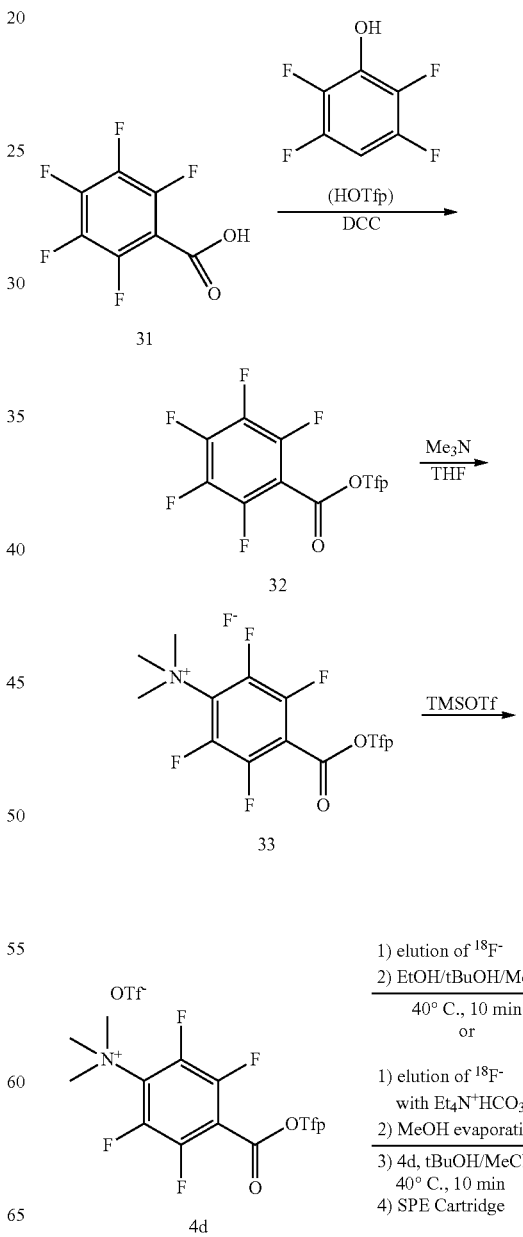

75
-continued

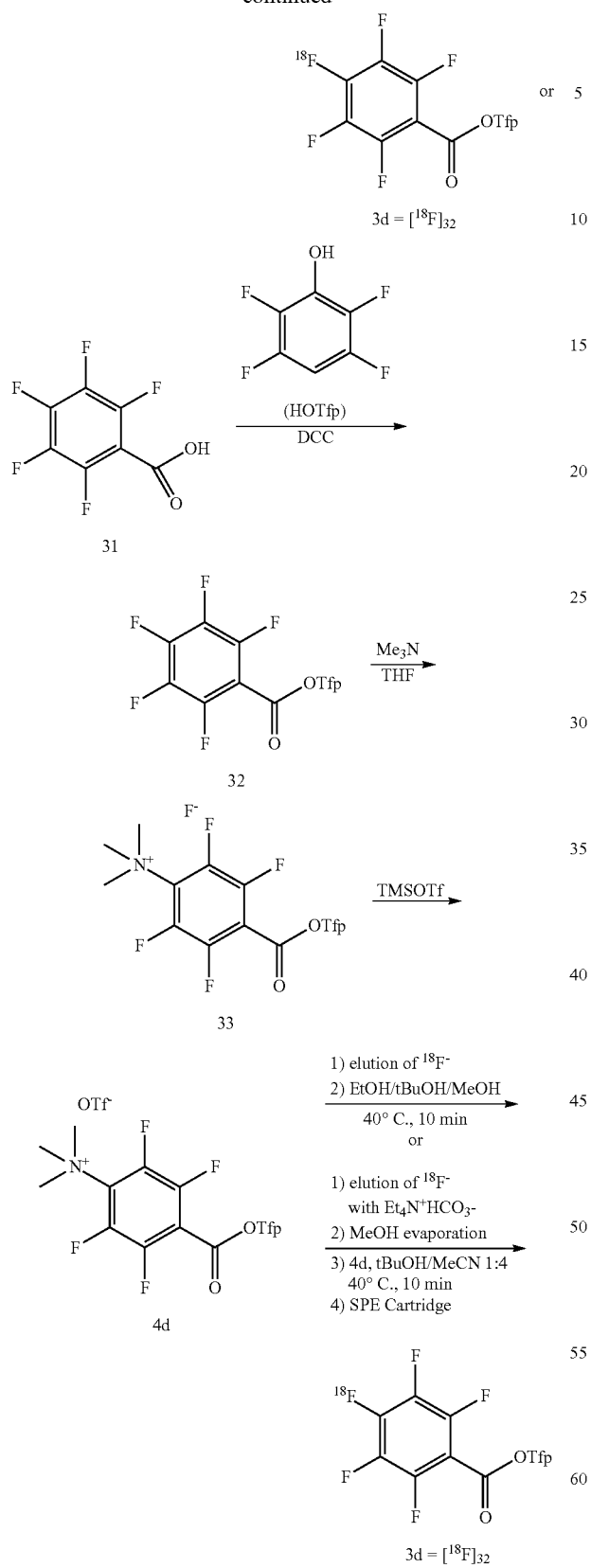

Compound 3d can be prepared exactly as 3e as described in the Example 10.

76

Example 13: Preparation of (2S)-2-({[(1S)-1-carboxy-5-{[6-[$^{18}$F]fluoropyridazin-3-yl]formamido}pentyl]carbamoyl}amino)butanedioic acid (1-17)

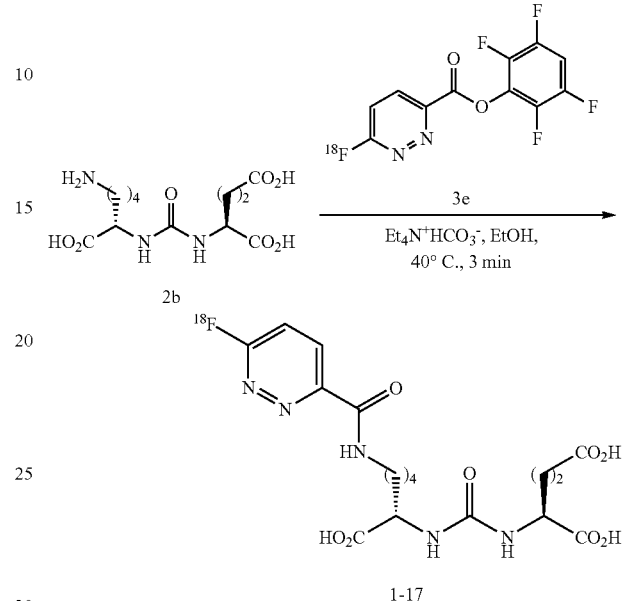

Compound 1-17 can be prepared exactly as [$^{18}$F]DCFPyL (1-10) as described in the Example 2.

Example 14: Preparation of (2S)-2-({[(1S)-1-carboxy-5-{[5-[$^{18}$F]fluoropyrazin-2-yl]formamido}pentyl]carbamoyl}amino)butanedioic acid (1-29)

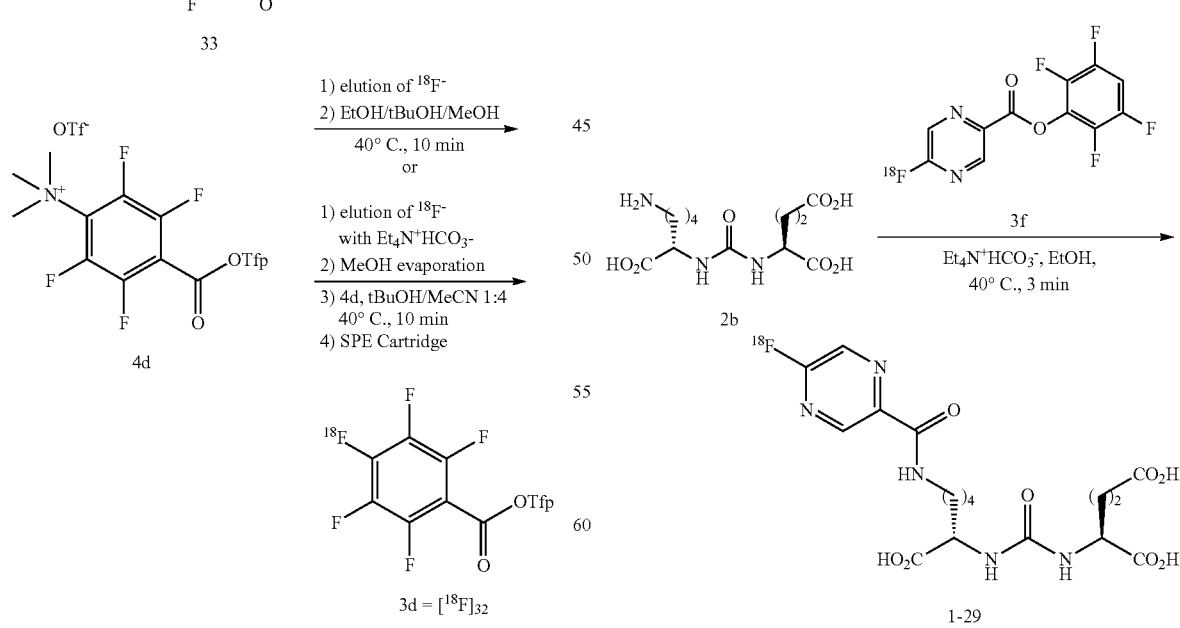

Compound 1-29 can be prepared exactly as [$^{18}$F]DCFPyL ([$^{18}$F] 1-10) as described in the Example 2.

Example 15: Preparation of (2S)-2-({[(1S)-1-car-boxy-5-(3-{[6-[$^{18}$F]fluoropyridin-3-yl]formamido}propanamido)pentyl]carbamoyl}amino)butanedioic acid (1-31)

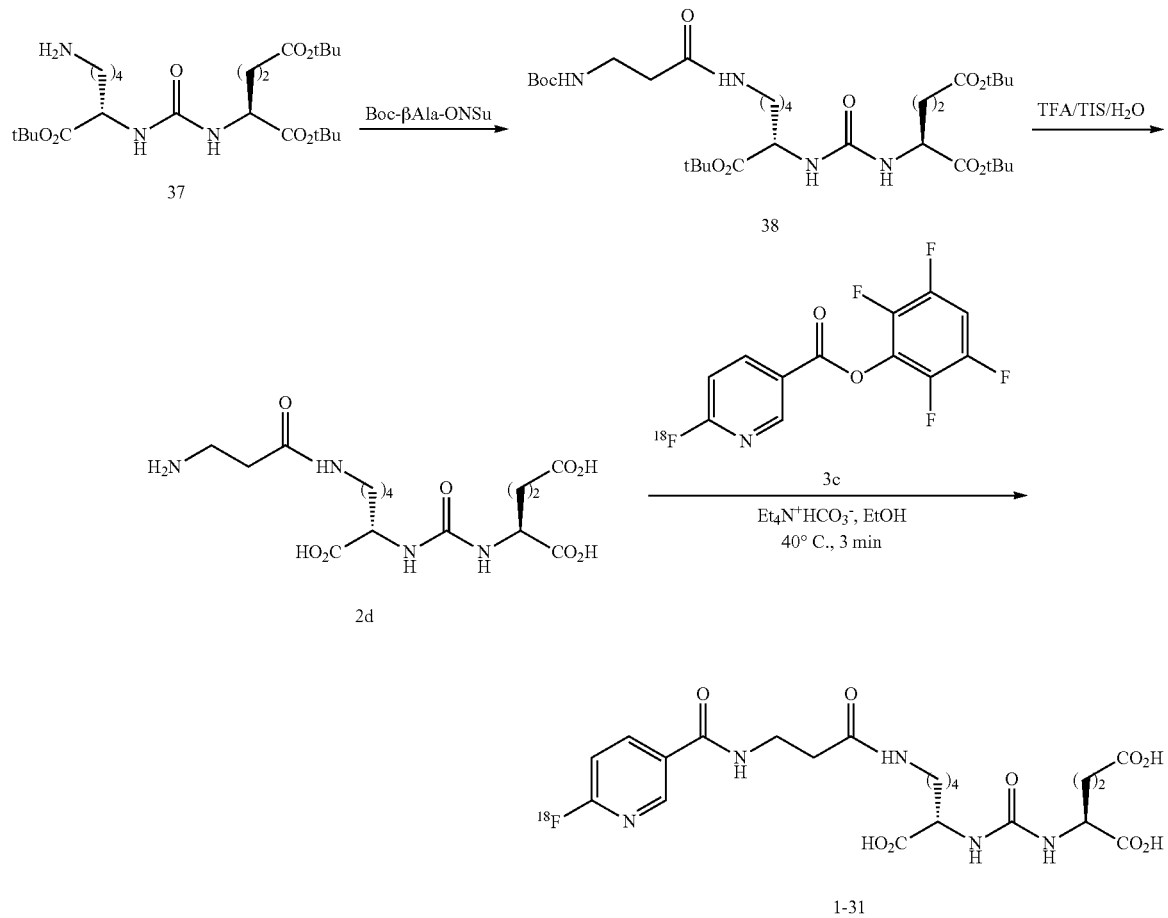

Compound 1-33 can be prepared analogously to [$^{18}$F]DCFPyL ([$^{18}$F]1-10) using 2d instead of 2b. 2d can in turn be prepared using conventional methods of peptide synthesis, for example, via acylation of known 37 with Boc-βAla-ONSu followed by cleavage of protecting groups.

Example 16: Preparation of (2S)-2-({[(1 S)-1-car-boxy-5-(2-{[6-[$^{18}$F]fluoropyridazin-3-yl]formamido}acetamido)pentyl]carbamoyl}amino)butanedioic acid (1-32)

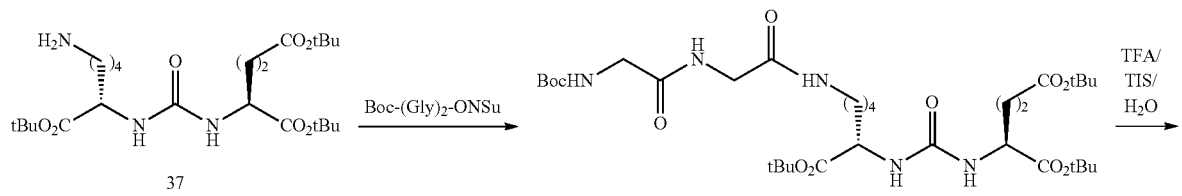

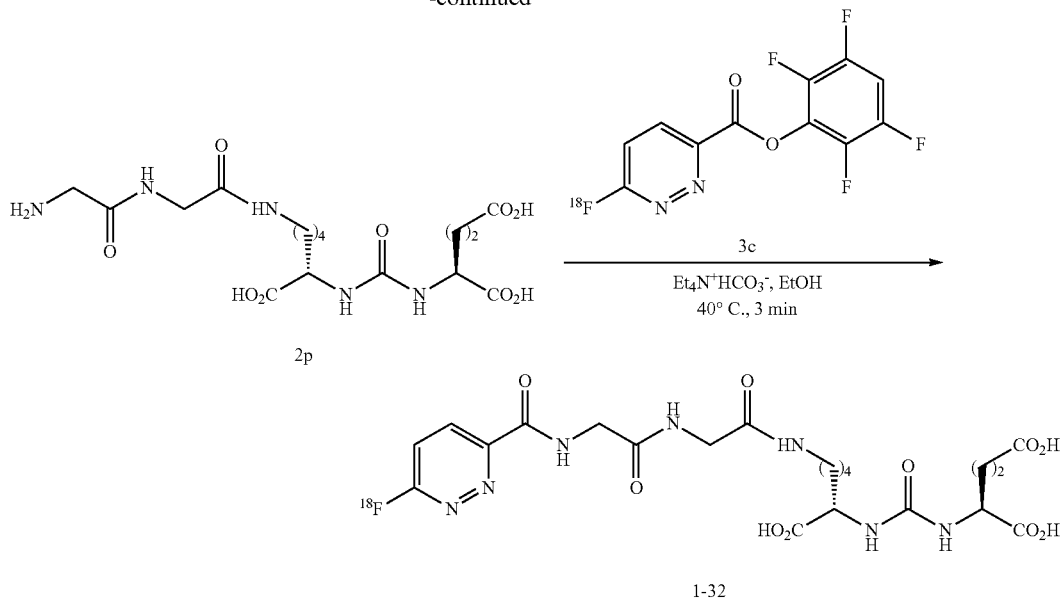

Compound 1-32 can be prepared analogously to [$^{18}$F]DCFPyL (1-10) using 2p instead of 2b. 2p can in turn be prepared using conventional methods of peptide synthesis, for example, via acylation of known 37 with Boc-Gly-Gly-ONSu followed by cleavage of protecting groups.

Example 17: Preparation of (2S)-2-({[(1S)-1-carboxy-5-[(4S)-4-carboxy-4-{[4-[$^{18}$F]fluoro-2,3,5,6-tetrafluorophenyl]formamido}butanamido]pentyl]carbamoyl}amino)butanedioic acid (1-33)

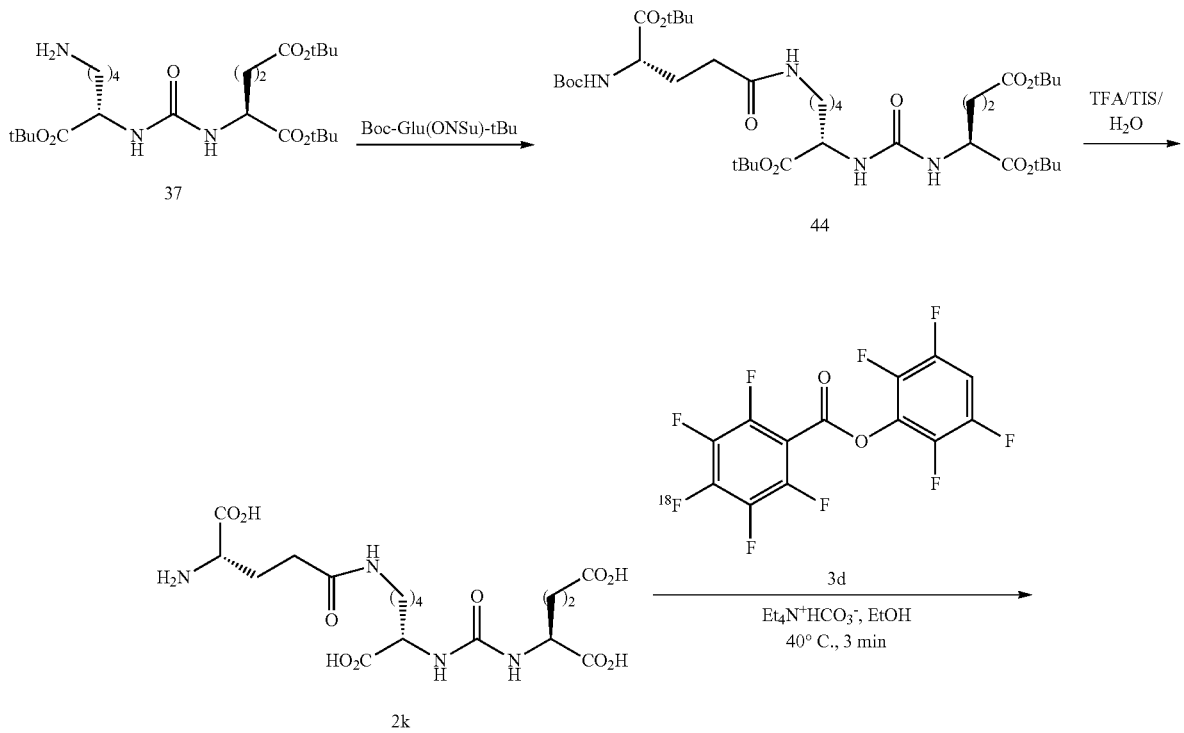

-continued

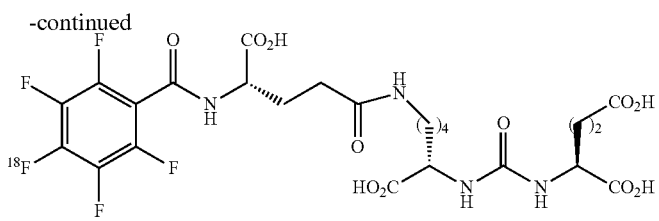

1-33

Compound 1-33 can be prepared analogously to [$^{18}$F] DCFPyL (1-10) using 2k instead of 2b. 1-33 can in turn be prepared using conventional methods of peptide synthesis, for example, via acylation of known 37 with Boc-Glu(ONSu)-OtBu followed by cleavage of protecting groups.

Example 18: Preparation of (2S)-2-({[(1S)-1-carboxy-5-[(4S)-4-carboxy-4-[(4S)-4-carboxy-4-{[6-[$^{18}$F]fluoropyridin-3-yl]formamido}butanamido]butanamido]-pentyl]carbamoyl}amino)butanedioic acid (1-34)

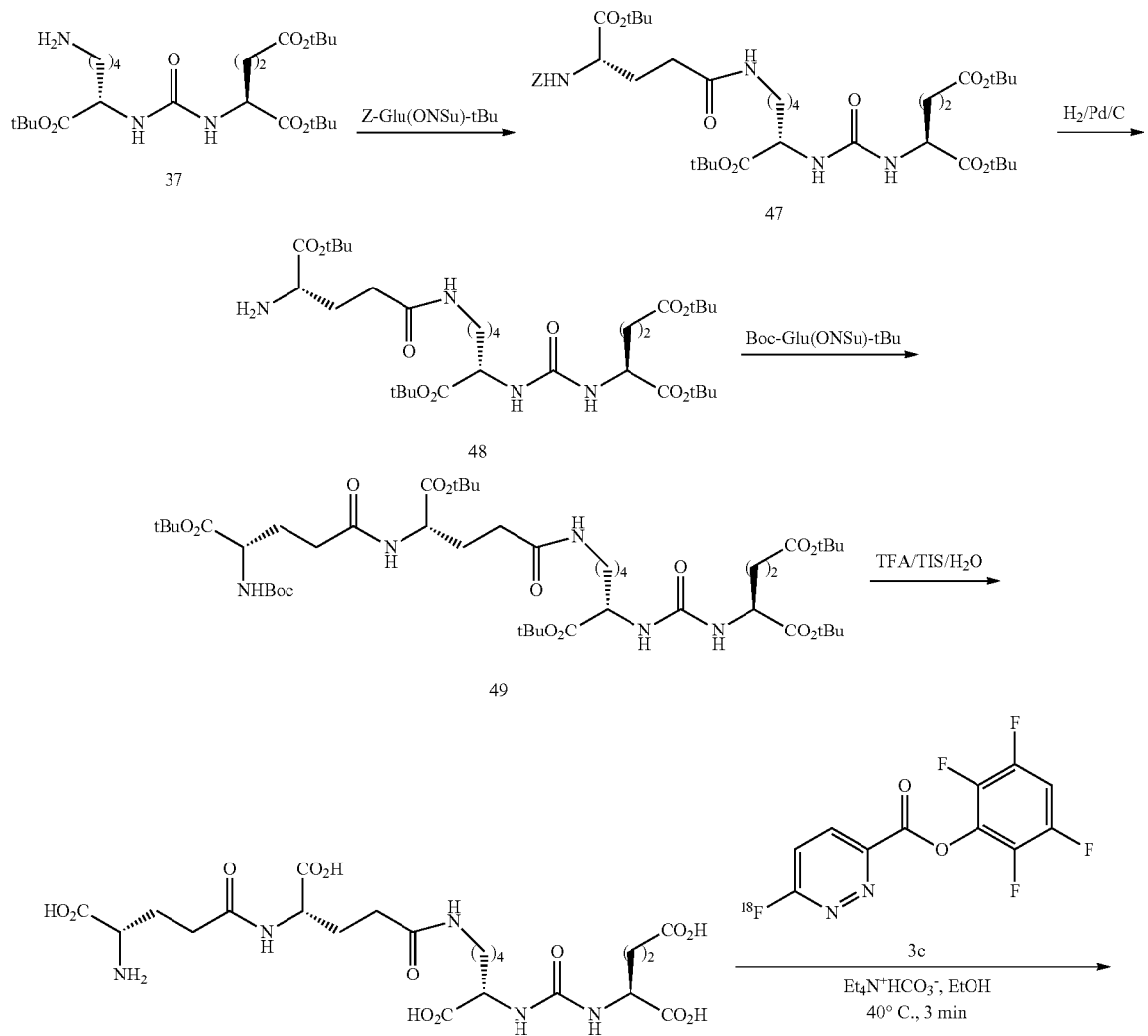

-continued

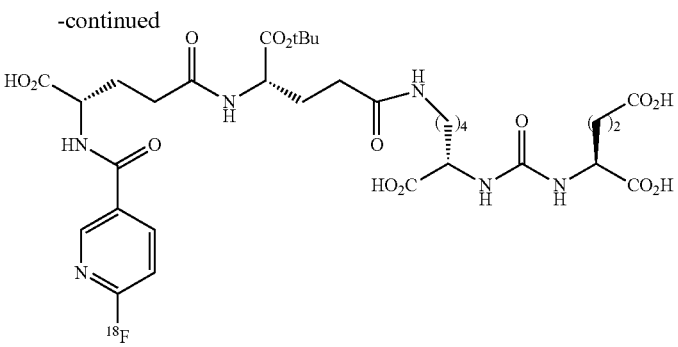

1-34

Compound 1-34 can be prepared analogously to [$^{18}$F] DCFPyL ([$^{18}$F]1-10) using 2n instead of 2b. 2n can in turn be prepared using conventional methods of peptide synthesis, for example, via acylation of known 37 with Z-Glu (ONSu)-OtBu followed by cleavage of Z (Z=benzyloxycarbonyl, Boc=tert-butyloxycarbonyl) group, followed by acylation of intermediate 49 with Boc-Glu (ONSu)-OtBu and final deprotection with TFA.

Example 19: Comparison of [$^{18}$F]DCFPyL ([$^{18}$F]1-10) with [$^{68}$Ga]HBED-CC (50) in PSMA$^+$-PCa Xenograft Mice

50

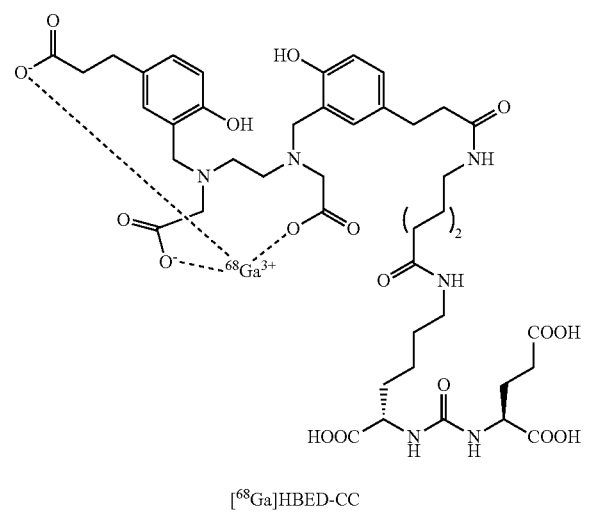

[$^{68}$Ga]HBED-CC

Methods:

Five 8-week-old male C.B-Igh-1b/IcrTac-Prkdcscid mice (Taconic) were injected subcutaneously in the neck region with 4×10$^6$ LNCaP-C4-2 prostate tumor cells. Three weeks after tumor implantation, two PET measurements with [$^{18}$F] DCFPyL ([$^{18}$F]1-10) and [$^{68}$Ga]HBED-CC (50), respectively, were performed using an Inveon μPET/CT scanner (Siemens) with a resolution of 1.4 mm FWHM at center of field of view. The first PET measurement was immediately followed by a CT scan during which the animal was left in the same position. Both tracers were injected i.v. through the lateral tail vein ([$^{18}$F]1-10: 21-32 MBq; [$^{68}$Ga]HBED-CC: 19-33 MBq, on two consecutive days). Emission data collection started 60 min after injection and lasted 45 min. Image reconstruction was performed using Fourier rebinning and an ordered subset expectation maximization (3D-OSEM) procedure, yielding images with voxel sizes of 0.78×0.78×0.80 mm. Image analysis was performed with VINCI 4.0 (MPI for Metabolism Research, Cologne, Germany). Tracer uptake in the tumor as well as liver, kidney, and background was determined using volumes of interest (VOIs) covering the respective structure. Significant differences were assessed using two-way repeated measures ANOVA with factors "structure" and "tracer", followed by Holm-Sidak post hoc comparison. Tumor sizes were measured by drawing accurate tumor VOIs in the CT images, and extracting VOI volume. Tracer uptake was correlated tumor size using the Pearson correlation test.

Results

Figure 2:
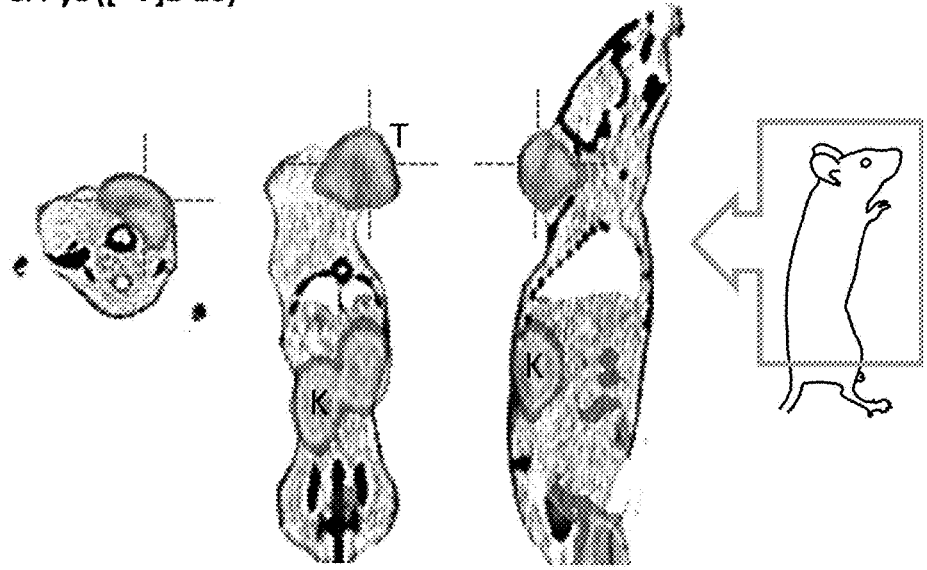
FIG. 2: [$^{68}Ga$]HBED-CC- (50) versus [$^{18}F$]DCFPyL (1-10)-PET in PSMA$^+$ PCa bearing mice. Shown are measurements in the same animal, on two consecutive days. Cursor position is indicated by crosslines. Abbreviations: K: kidney; T: tumor. Scale bar: 10 mm.
Figure 2:
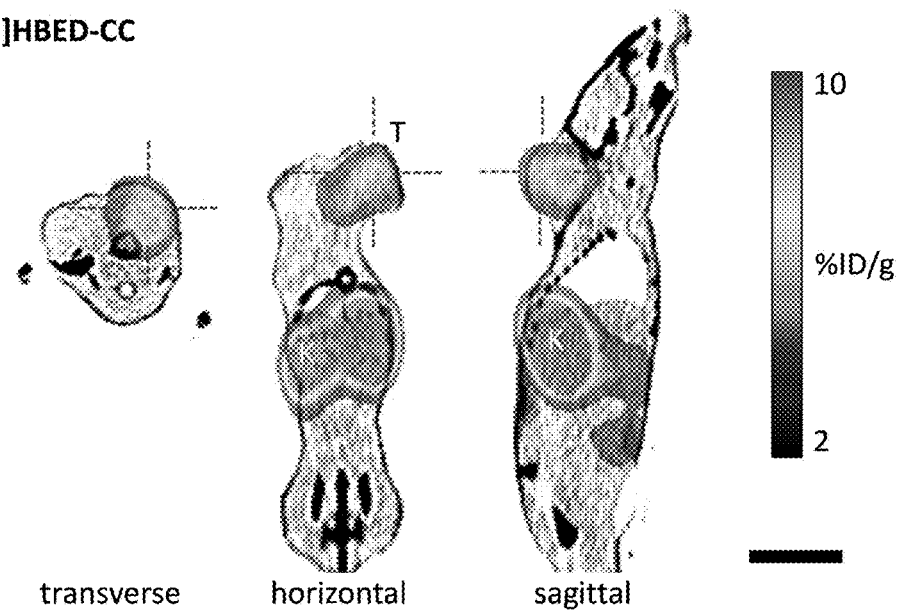

As shown in FIG. 2, tumor tracer uptake was similar for the two tracers (FIG. 2): 1.4±1.7% ID/g for [$^{18}$F]1-10, and 1.8±2.0% ID/g for [$^{68}$Ga]HBED-CC (50) (not significant). There was a significant positive correlation between tumor size and tracer uptake for both tracers: R=0.97, p=0.0059 for [$^{18}$F]1-10, and R=0.98, p=0.0019 for [$^{68}$Ga]HBED-CC (50). Signal-to-noise ratio (tumor versus background) was nearly identical as well with 5.9±4.2 for [$^{18}$F]1-10, and 6.7±6.9 for [$^{68}$Ga]HBED-CC (50). While liver uptake was similar as well (1.1±0.5% ID/g for [$^{18}$F]1-10, and 0.7±0.2% ID/g for [$^{68}$Ga]HBED-CC (50); not significant), [$^{18}$F]1-10 uptake in the kidney (3.0±1.9% ID/g) was significantly lower than [$^{68}$Ga]HBED-CC (50) uptake (13.9±6.4% ID/g; $F(3,12)=25.6$, $p<0.0001$ for factor interaction, post-hoc $p<0.05$).

Figure 3:
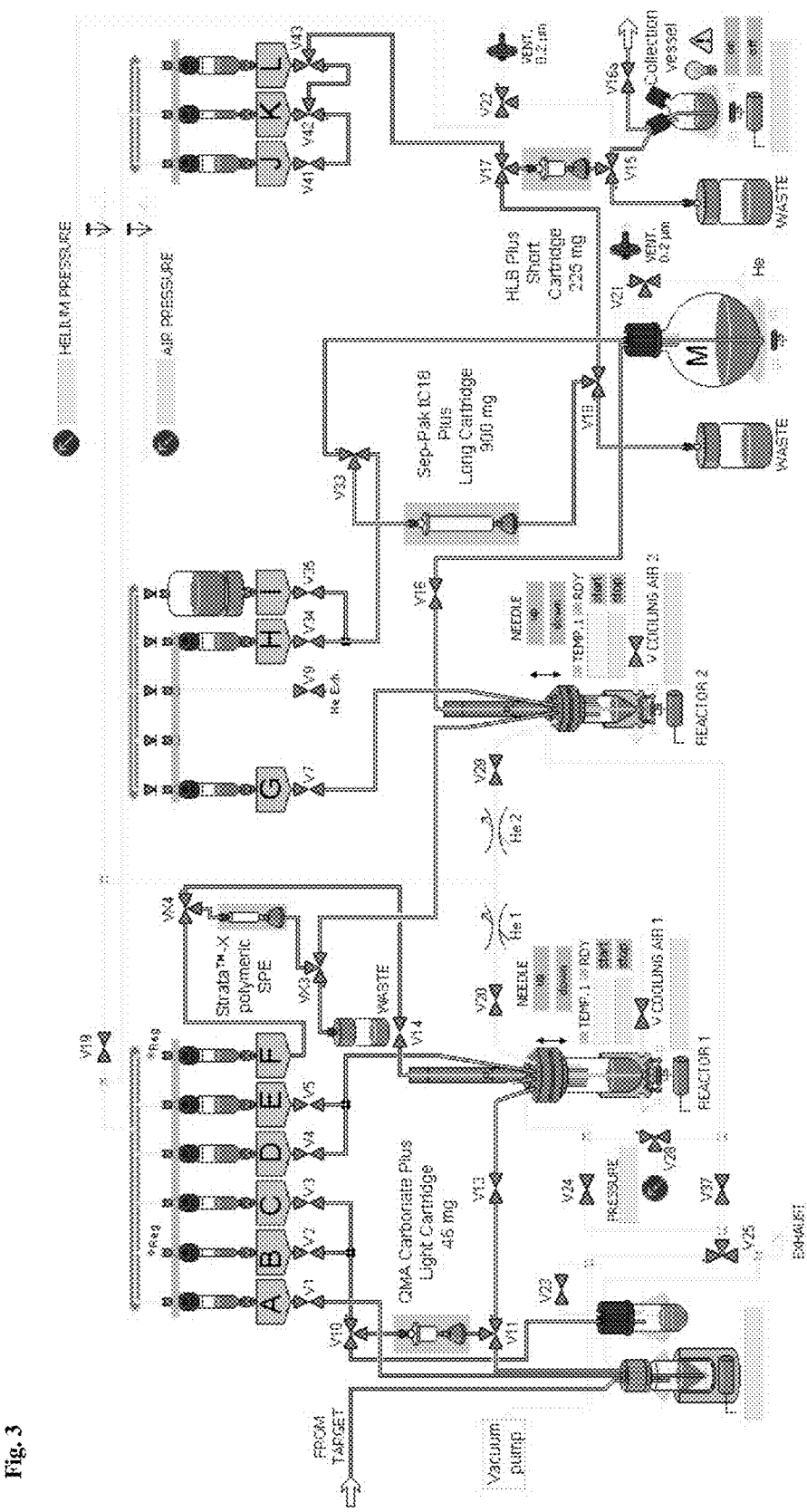
FIG. 3: Automatic synthesis of [$^{18}F$]DCFPyL without HPLC purification in a TRACERLab FX$_{fn}$ automated radiochemistry synthesis module (GE Medical Systems). Reference signs A to I in FIG. 3 have the following meaning.

Example 20: Automated Synthesis of [$^{18}$F]DCFPvL 1-10 Starting from [$^{18}$F]Fluoride without HPLC Purification (FIG. 3)

Aqueous [$^{18}$F]fluoride (0.05-50 GBq) was transferred from the target to a trapping vial. Aqueous [$^{18}$F]fluoride was then vacuum-transferred from the trapping vial through an anion-exchange resin cartridge (Sep-Pak QMA carbonate light 46 mg, preconditioned with 1 mL water) from the male side of the cartridge, and [$^{18}$O]H$_2$O was collected in a separate vial. The cartridge was subsequently washed with EtOH (3 mL) from vial A from the female side of the cartridge. Washings were discarded. Thereafter, [$^{18}$F]fluoride was slowly eluted from the resin with N,N,N-trimethyl-5-[(2,3,5,6-tetrafluorophenoxy)-carbonyl]pyridine-2-aminium trifluoromethanesulfonate 4c (10 mg, 20 μmoL) in EtOH (200 μL) from the vial B into reactor R1 with a low flow of helium. After this, MeCN/tBuOH 1:4 (2 mL) from vessel C was passed through the cartridge into reactor R1.

Reactor R1 was filled with helium, sealed and the reaction mixture was heated at 45° C. for 15 min. After cooling to room temperature the crude [$^{18}$F]F-Py-Tfp 3c was diluted with water (15 mL) from vessel E and passed through a polymer RP cartridge (Strata X, preconditioned with 1 mL EtOH and washed with 5 mL water). The cartridge was washed with H$_2$O (10 mL) from reservoir D and dried by applying a helium stream for 5 min. [$^{18}$F]F-Py-Tfp 3c was eluted with a mixture of ethanol (250 µL), freshly prepared ethanolic solution of HO-syL-C(O)-Glu-OH 2b (2.5 mg, 100 µL) and 0.5 M tetraethylammonium bicarbonate in EtOH (60 µL) from vial F into reactor R2. The reaction mixture was heated at 40° C. for 3 min. After cooling to room temperature the reaction mixture was diluted with water from vial G and transferred to vessel M containing 0.1% TFA (20 mL). The acidic solution was loaded onto a tC18 cartridge (Sep-Pak tC18 Plus Long Cartridge, 900 mg, preconditioned with 10 mL EtOH and washed with 30 mL water). The cartridge was subsequently washed with water (10 mL) from vial H and [$^{18}$F]DCFPyL was eluted with 10% EtOH-solution of 1.7% phosphoric acid (60 mL) onto a HLB catridge (Oasis HLB Plus Short Cartridge 225 mg, preconditioned with 10 mL EtOH and washed with 30 mL water) from Vessel I. The HLB cartridge was washed with 10 mL water by vessel L and [$^{18}$F]DCFPyL was eluted with 50 Vol % ethanol in isotonic saline (2 mL; v/v). The solution was diluted with isotonic saline (9 mL) and sterile filtered. Quality control: eluent: phosphoric acid (1.7%) with 10% EtOH for 5 min, then with 50% EtOH for 2 min. Flow rate: 3 mL/min. Column: Chromolith® SpeedROD RP-18e column (Merck, Darmstadt Germany), 50×4.6 mm. Retention times: [$^{18}$F]DCFPyL~3 min; [$^{18}$F]F-Py-Tfp~5.7 min.

Example 21: Automated Cassette Module Synthesis of [$^{18}$F]DCFPyL 1-10 Starting from [$^{18}$F]Fluoride without HPLC Purification (FIG. 4)

Aqueous [$^{18}$F]fluoride (0.05-50 GBq) was transferred from the target to the receiver vial at position E. Aqueous [$^{18}$F]fluoride was then vacuum transferred from the receiver vial E through an anion-exchange resin cartridge (Sep-Pak QMA carbonate light 46 mg, preconditioned with 1 mL water) via CP➜Ba➜A. [$^{18}$O]H$_2$O was collected in the collection vial. The cartridge was subsequently washed with EtOH (1 mL) from reservoir D by action of syringe 1 (S1) via D➜S1 and then S1➜B➜C➜Waste two times. Thereafter, [$^{18}$F]fluoride was slowly eluted from the resin with N,N,N-trimethyl-5-[(2,3,5,6-tetrafluorophenoxy)-carbonyl] pyridine-2-aminium trifluoromethanesulfonate 4c (10 mg, 20 µmol) in EtOH (200 µL) from the vial at position J into the reactor via J➜S1 and then S1➜B➜C➜G. The reaction solvent MeCN/tBuOH 1:4 (2 mL) from vessel at position K was passed through the cartridge into the reactor via K➜S1 and then S1➜B➜C➜G, too. The reactor was sealed and the reaction mixture was heated at 50° C. for 15 min. The crude [$^{18}$F]F-Py-Tfp 3c was purified by SPE. This was accomplished by a stepwise dilution procedure of the crude reaction mixture. At first the hot reaction mixture was quenched with water (2 ml) from the reservoir at position M by action of syringe 2 (S2) via M➜S2 and then S2➜G. Then syringe 2 was partially filled with water (5.5 mL) via M➜S2, and an aliquot (1 mL) crude [$^{18}$F]F-Py-Tfp was sucked into the syringe 2 via G➜S2. The diluted solution was passed through a small C18 cartridge (Sep-Pak C18 Plus Light Cartridge, 130 mg) at position H via S2➜H➜R➜Waste. The whole procedure was repeated until full recovery of the reaction mixture was achieved. The cartridge was washed with water (5 mL) via M➜S2 and S2➜H➜R➜Waste, and dried with a nitrogen stream for 20 s via A➜H➜R➜Waste. The reactor, manifold, the tubing H➜R and syringe 1 was thoroughly cleaned by a procedure involving flushing with ethanol and dried with a stream of nitrogen. The [$^{18}$F]F-Py-Tfp 3c was eluted from the small C$_{18}$ cartridge with a solution of HO-syL-C(O)-Glu-OH 2b (2.5 mg) and 0.5 M tetraethylammonium bicarbonate in EtOH (500 VL) from vial at position L into reactor via L➜R➜H➜G by applying vacuum at V➜Reactor. The reaction mixture was heated at 40° C. for 3 min and, thereafter, quenched with 0.5% trifluoroacetic acid (4 mL) from vessel at position N via N➜S2 and S2➜G. The acidic solution of [$^{18}$F]DCFPyL was further diluted with H$_2$O and loaded onto a tC18 cartridge (Sep-Pak tC18 Plus Long Cartridge, 900 mg, preconditioned with 5 mL EtOH and washed with 15 mL water). To achieve this, syringe 2 was partially filled with water (4 mL) via M➜S2, then an aliquot of the crude reaction mixture (1 mL) was sucked into the syringe 2 via G➜S2. This solution was passed through the tC18 cartridge (Sep-Pak C18 Plus Light Cartridge, 130 mg) via S2➜H➜R➜Waste. The whole dilution procedure was performed at least four times to archive full recovery of the reaction mixture in the reactor. The cartridge was subsequently washed with water (5 mL) from the reservoir via M➜S2 and S2➜H➜R➜Waste, and dried by applying a high flow nitrogen stream for 5 s via A➜H➜R➜Waste. The [$^{18}$F]DCFPyL was stepwise eluted from the tC$_{18}$ phase with 10 Vol % EtOH-solution of 1.7% phosphoric acid (total volume of 60 mL) onto a HLB cartridge (Oasis HLB Plus Short Cartridge 225 mg, preconditioned with 5 mL EtOH and washed with 15 mL water) from vessel at position O by action of syringe 2 via O➜S2 and then S2➜P➜Q➜S➜T➜Waste to archive further purification. After this, the HLB cartridge was washed with 10 mL water via M➜S2 and then S2➜S➜T➜Waste. The purified [$^{18}$F]DCFPyL was eluted with ethanol (1 mL) from reservoir D via D➜S1 into syringe 3 (S3) via S1➜S➜T➜S3. The ethanolic [$^{18}$F]DCFPyL solution in syringe 3 was further diluted with isotonic saline (total volume of 10 mL) from vessel I via I➜S➜T➜S3 and dispensed upon operators request into the tracer vial at position U (S3➜U) with simultaneous sterile filtration to give the PET-tracer as a ready for injection solution in 9% EtOH in isotonic saline. Quality control: eluent: 1.7% phoshoric acid/EtOH=9/1 for 5 min, then 1.7% phoshoric acid/EtOH=1/1 for 2 min. Flow rate: 3 mL/min. Column: Chromolith® SpeedROD RP-18e column (Merck, Darmstadt Germany), 50×4.6 mm. Retention times: [$^{18}$F]DCFPyL~3 min; [$^{18}$F]F-Py-Tfp~5.7 min.

Additional Embodiments of the Invention

1. A method for preparing a compound of formula (I)

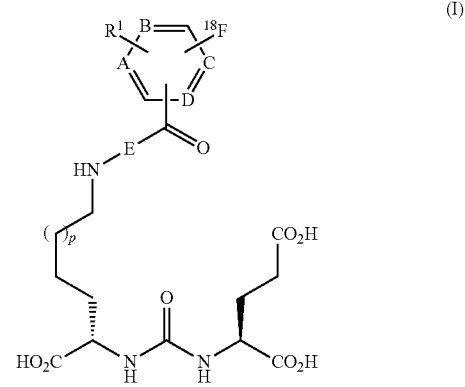

wherein

A, B, C, and D represent independently of each other C—H, C—F or N; and not more than two of A, B, C, and D represent N;

E represents a covalent bond or

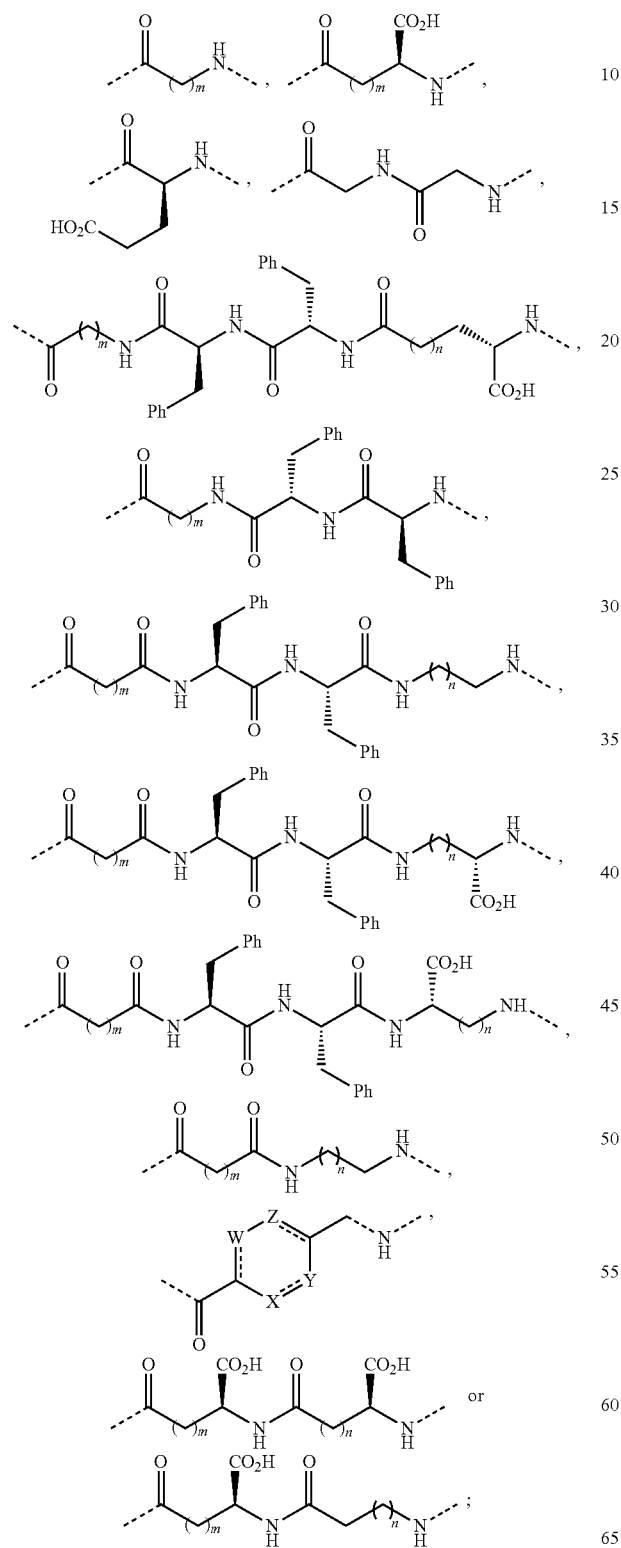

$R^1$ represents $C_1$-$C_3$ alkyl, $C_1$-$C_3$ alkoxy, $C_1$-$C_3$ haloalkyl, $C_1$-$C_3$ haloalkoxy, $C_2$-$C_4$ alkylcarbonyl, $C_2$-$C_4$ alkyloxycarbonyl, $C_2$-$C_4$ alkylcarboxy, aryloxy, arylcarboxy, cyano, or nitro;

n is an integer selected from 0 to 10;

m is an integer selected from 1 to 18;

p is an integer selected from 0 to 10;

X, Y, W, and Z represent independently of each other —$CH_2$—, —CH—, —NH— or —N—;

---- represents a single or double bond;

and diastereomers, enantiomers, hydrates, and salts thereof;

comprising the steps:

(A) providing a solution of a compound of formulae (II) in a polar protic solvent or in a solvent mixture containing a polar protic solvent containing at least one base

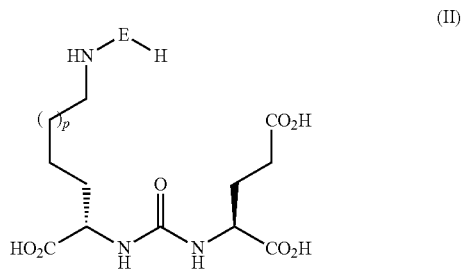

(II)

wherein E and p have the meanings as defined above, (B) providing a solution of a compound of formula (III)

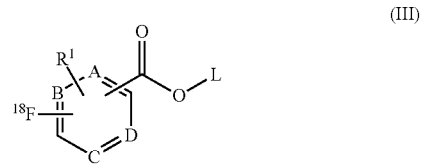

(III)

wherein A, B, C, D and $R^1$ have the meanings as defined above, and OL represents a leaving group in a polar protic solvent or in a solvent mixture containing a polar protic solvent;

(C) mixing the solution of the compound of formula (II) and the solution of the compound of formula (III) and allowing the compound of formula (II) to react with the compound of formula (III) in order to obtain the compound of formula (I), (D) purifying the compound of formula (I) preferably by using isotonic sodium chloride solution.

2. Method according to embodiment 1, wherein step (C) is performed at a reaction temperature T2 which is in the range of 30° C. to 60° C. and during a reaction time t2 which is 1-30 min and a pH value of the reaction solution which is in the range of 7.0-11.0.

3. Method according to embodiment 1 or 2, wherein L in the leaving group OL represents:

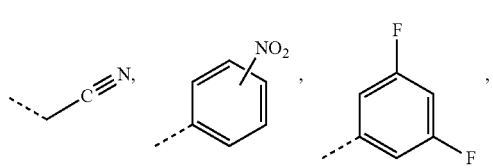

-continued

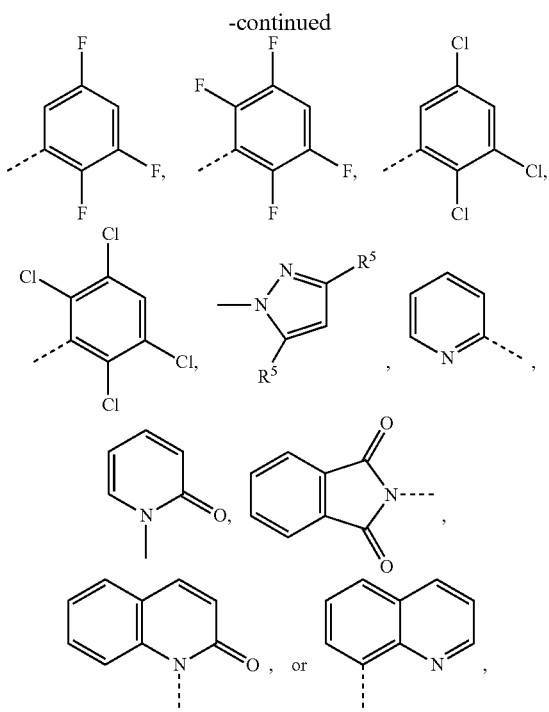

and wherein $R^5$ is selected from methyl, ethyl, or n-propyl;

4. Method according to embodiments 1, 2 or 3 further comprising the following step (E) after the step (D):
   (E) sterilizing the solution of the compound of formula (I) via steril filtration.
5. Method according to embodiments 1, 2, 3 or 4 further comprising the following steps (A1)-(A8) after step (A) and before step (B):
   (A1) providing a solution of a compound of the formula (IV) in at least one polar protic solvent or in a solvent mixture containing a polar protic solvent, wherein optionally the solution further contains a salt;

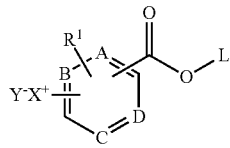

wherein
A, B, C, D, OL and $R^1$ have the same meanings as defined in embodiment 1;
X represents $NR^2_3$, $IR^3$, $SR^3_2$;
Y represents Br, I, $BF_4$, $O_2CCF_3$, $OSO_2CF_3$, $ClO_4$, $NO_2$, $OSO_2C_6H_4CH_3$, $OSO_2CH_3$
$R^2$ represents $C_1$-$C_4$ alkyl; and
$R^3$ represents aryl;
(A2) providing an aqueous solution of [$^{18}$F]fluoride;
(A3) loading the aqueous solution of [$^{18}$F]fluoride onto an anion exchange resin;
(A4) washing the anion exchange resin with a polar protic solvent or with a polar aprotic solvent;
(A5) flushing of the solvent with air or inert gas flow;
(A6) eluting of [$^{18}$F]fluoride with the solution of the compound of formula (IV) provided in step (A1) and diluting the resulting solution with an aprotic solvent or with at least one $C_3$-$C_6$ alcohol or with a solvent mixture of at least one $C_3$-$C_6$ alcohol and an aprotic solvent; or eluting of [$^{18}$F]fluoride with the solution of the compound of formula (IV) provided in step (A1), concentrating of the resulting solution and redissolving of the residue in an aprotic solvent;
(A7) allowing the compound of formula (IV) to react with [$^{18}$F]fluoride in order to obtain the compound of the formula (III);

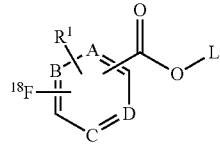

wherein A, B, C, D, OL and $R^1$ have the same meanings as defined in embodiment 1; and
(A8) purifying of the compound of formula (III).
6. Method according to any one of the embodiments 1-5 further comprising the following step (F) after the step (D) or (E):
   (F) preparing a pharmaceutical composition containing the solution of the compound of formula (I).
7. Method according to any one of the embodiments 1-6, wherein the base in step (A) is an organic nitrogen-containing base or a bicarbonate.
8. Method according to embodiment 7, wherein the organic nitrogen-containing base or the bicarbonate is selected from the group consisting of: $LiHCO_3$, $NaHCO_3$, $KHCO_3$, $CsHCO_3$, $Me_4NHCO_3$, $Et_4NHCO_3$, $n\text{-}Pr_4NHCO_3$, $i\text{-}Pr_4NHCO_3$, $n\text{-}Bu_4NHCO_3$, $i\text{-}Bu_4NHCO_3$, $Et_3N$, pyridine, lutidine, collidine, diisopropylethylamine, $n\text{-}Pr_3N$, $i\text{-}Pr_3N$, $n\text{-}Bu_3N$, $i\text{-}Bu_3N$, $Oct_3N$, N-methyl-morpholine, N-ethylmorpholine, N-methylpiperidine, N-ethylpiperidine, N,N-dicyclohexylmethylamine, N,N-dimethylcyclohexylamine, N-methyl-dibutylamine, N-ethyldicyclohexylamine, N,N-dimethylbutylamine, and N,N-dimethylhexylamine
9. Method according to any one of the embodiments 1-8, wherein the polar protic solvent is an anhydrous polar protic solvent, especially anhydrous MeOH or anhydrous EtOH or a mixture thereof.
10. Method according to any one of the embodiments 1-9, wherein the compound (III) is

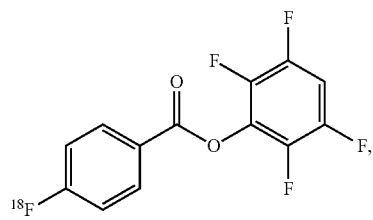

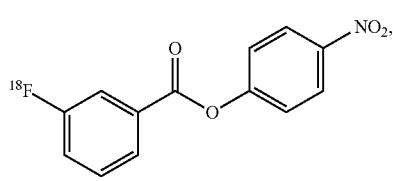

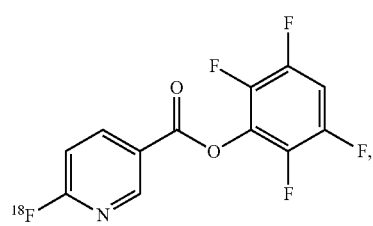

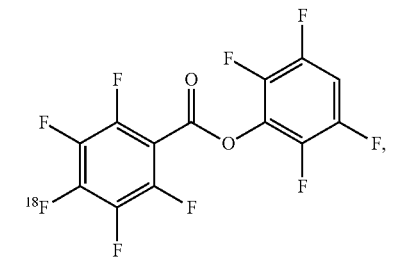
3d

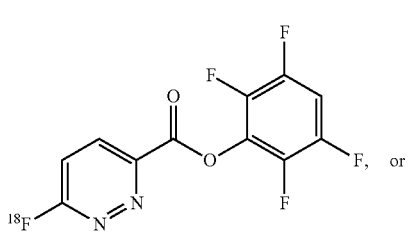
3e

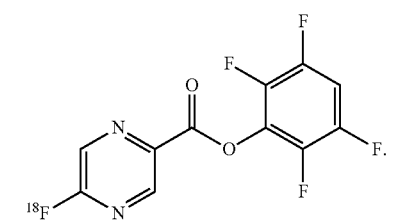
3f

11. Method according to any one of the embodiments 5-10, wherein the [$^{18}$F]fluoride is trapped on an anion exchange resin and then eluted directly.

12. Method according to any one of the embodiments 5-11, wherein the $C_3$-$C_6$ alcohol is tBuOH.

13. Method according to any one of the embodiments 1-12, wherein the compound of the formula (I) is selected from the group consisting of compounds 1-3, 1-10, 1-14, 1-17, 1-29, 1-31, 1-32, 1-33, and 1-34:

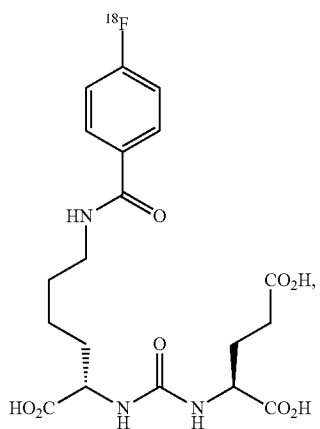
1-3

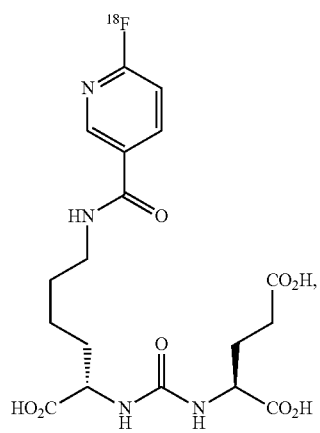
1-10

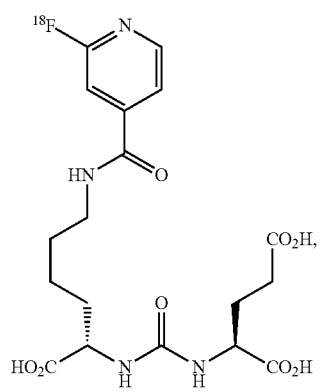
1-14

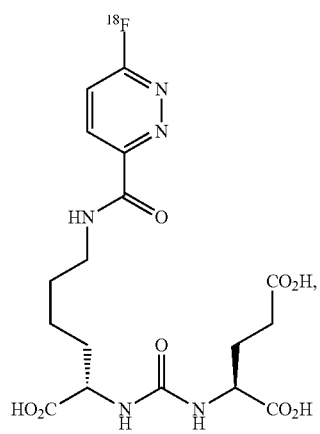
1-17

-continued

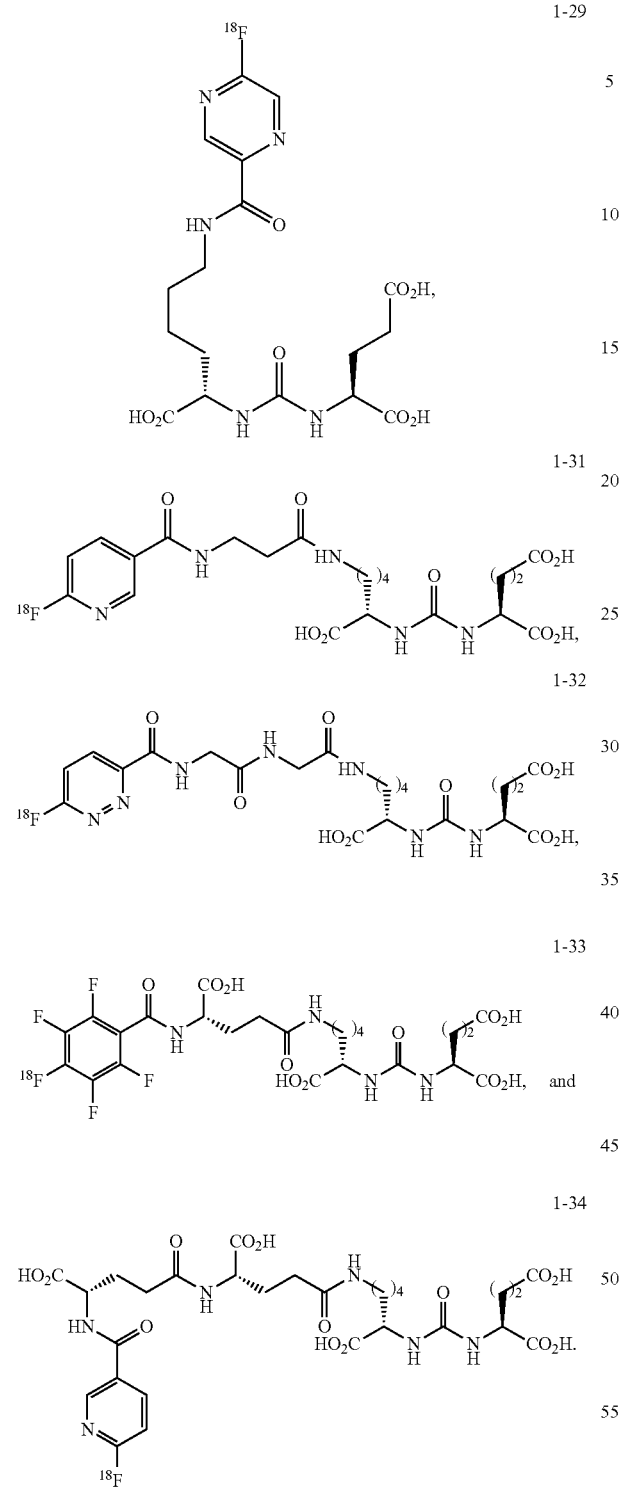

1-29

1-31

1-32

1-33

1-34

14. Pharmaceutical composition containing at least one compound of formula (I) as defined in embodiment 1 together with at least one pharmaceutically acceptable solvent, ingredient and/or diluent.

15. Pharmaceutical composition according to embodiment 14 for use in imaging prostate cancer cells or prostate cancerous tissue.

16. A method for preparing a compound of formula (I)

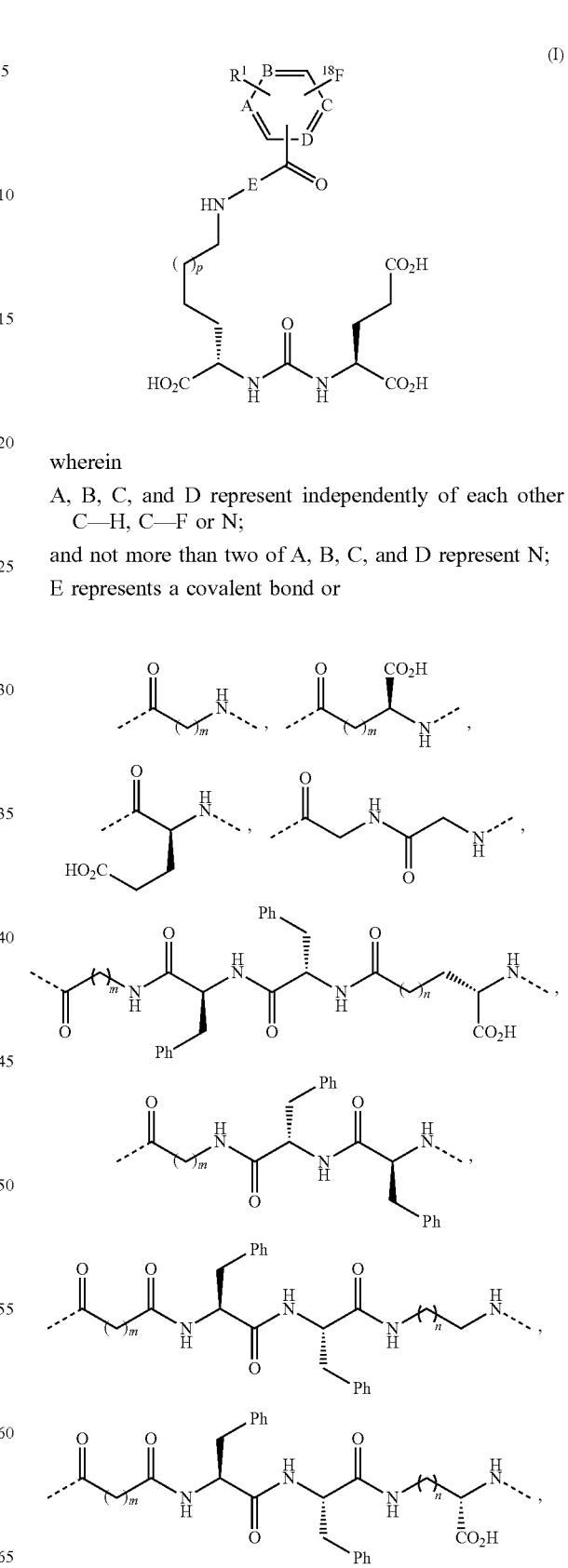

wherein

A, B, C, and D represent independently of each other C—H, C—F or N;

and not more than two of A, B, C, and D represent N;

E represents a covalent bond or

-continued

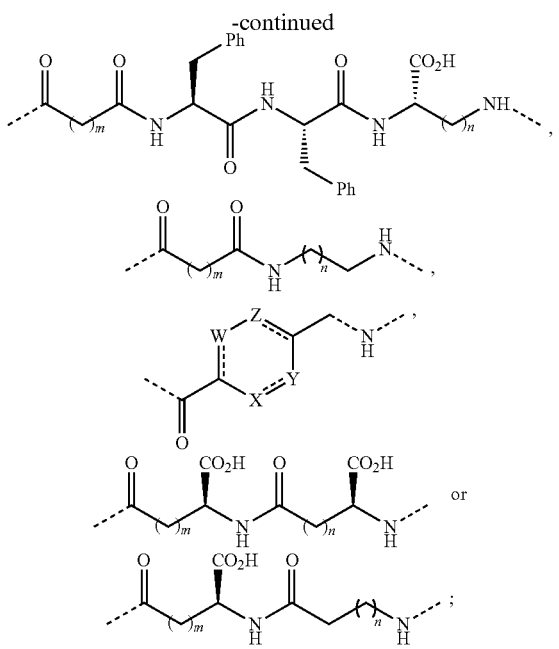

$R^1$ represents $C_1$-$C_3$ alkyl, $C_1$-$C_3$ alkoxy, $C_1$-$C_3$ haloalkyl, $C_1$-$C_4$ alkylcarboxy, aryloxy, arylcarboxy, cyano, or nitro;
n is an integer selected from 0 to 10;
m is an integer selected from 1 to 18;
p is an integer selected from 0 to 10;
X, Y, W, and Z represent independently of each other —$CH_2$—, C—H, —NH— or N;
---- represents a single or double bond;
and diastereomers, enantiomers, hydrates, and salts thereof;
comprising the steps:
(A) providing a solution of a compound of formulae (II) in a polar protic solvent or in a solvent mixture containing a polar protic solvent containing at least one base

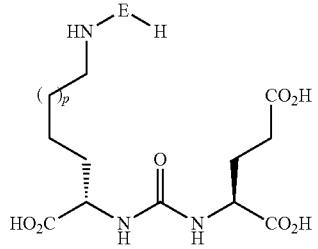
(II)

wherein E and p have the meanings as defined above,
(B) providing a solution of a compound of formula (III)

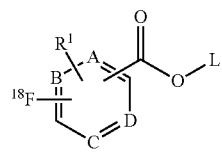
(III)

wherein
A, B, C, D and $R^1$ have the meanings as defined above, and
OL represents a leaving group
in a polar protic solvent or in a solvent mixture containing a polar protic solvent;
(C) mixing the solution of the compound of formula (II) and the solution of the compound of formula (III) and allowing the compound of formula (II) to react with the compound of formula (III) in order to obtain the compound of formula (I),
(D) purifying the compound of formula (I).
17. Method according to embodiment 16, wherein step (C) is performed at a reaction temperature T2 which is in the range of 30° C. to 60° C. and during a reaction time t2 which is 1-30 min and at a pH value of the reaction solution which is in the range of 7.0-11.0.
18. Method according to embodiment 16 or 17, wherein L in the leaving group OL represents:

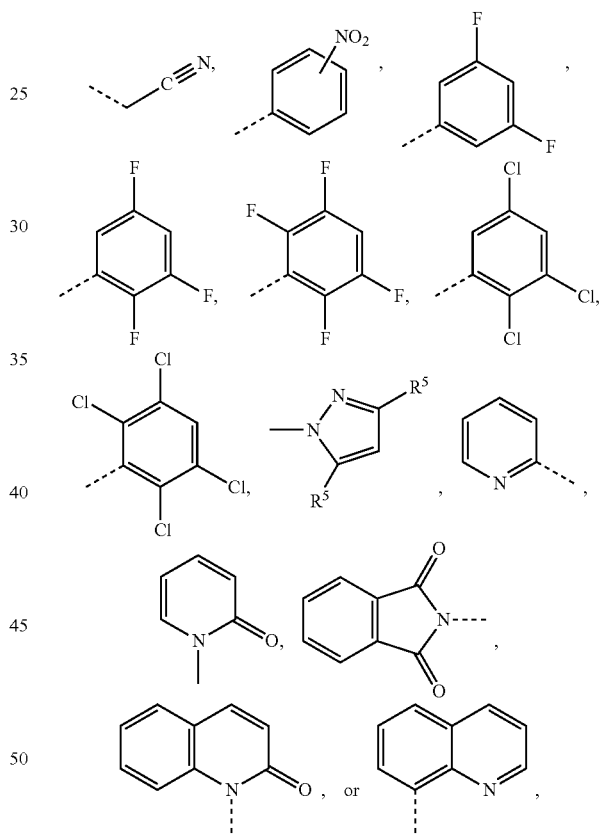

and wherein $R^5$ is selected from methyl, ethyl, or n-propyl;
19. Method according to any one of embodiments 16 to 18 further comprising the following step (E) after the step (D):
(E) sterilizing the solution of the compound of formula (I) via sterile filtration.
20. Method according to any one of embodiments 16 to 19 further comprising the following steps (A1)-(A8) after step (A) and before step (B):
(A1) providing a solution of a compound of the formula (IV) in at least one polar protic solvent or in a solvent mixture containing a polar protic solvent, wherein optionally the solution further contains a salt;

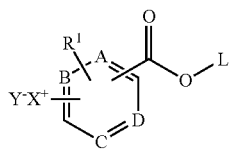

(IV)

wherein
A, B, C, D, OL and R¹ have the same meanings as defined in claim 1;
X represents $NR^2_3$, $IR^3$, $SR^3_2$;
Y represents Br, I, $BF_4$, $O_2CCF_3$, $OSO_2CF_3$, $ClO_4$, $NO_2$, $OSO_2C_6H_4CH_3$, $OSO_2CH_3$
$R^2$ represents $C_1$-$C_4$ alkyl; and
$R^3$ represents aryl;
(A2) providing an aqueous solution of [¹⁸F]fluoride;
(A3) loading the aqueous solution of [¹⁸F]fluoride onto an anion exchange resin;
(A4) washing the anion exchange resin with a polar protic solvent or with a polar aprotic solvent;
(A5) flushing of the solvent with air or inert gas flow;
(A6) eluting of [¹⁸F]fluoride with the solution of the compound of formula (IV) provided in step (A1) and diluting of the resulting solution with an aprotic solvent or with at least one $C_3$-$C_6$ alcohol or with a solvent mixture of at least one $C_3$-$C_6$ alcohol and an aprotic solvent;
or
eluting of [¹⁸F]fluoride with the solution of the compound of formula (IV) provided in step (A1), concentrating of the resulting solution and redissolving of the residue in an aprotic solvent;
(A7) allowing the compound of formula (IV) to react with [¹⁸F]fluoride in order to obtain the compound of the formula (III);

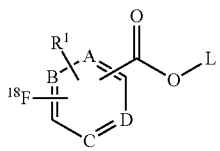

(III)

wherein A, B, C, D, OL and R¹ have the same meanings as defined in claim 1; and
(A8) purifying of the compound of formula (III).
21. Method according to any one of the embodiments 16-20 further comprising the following step (F) after the step (D) or (E):
(F) preparing a pharmaceutical composition containing the solution of the compound of formula (I).
22. Method according to any one of the embodiments 16 to 21, wherein the base in step (A) is selected from the group consisting of:
$LiHCO_3$, $NaHCO_3$, $KHCO_3$, $CsHCO_3$, $Me_4NHCO_3$, $Et_4NHCO_3$, $n-Pr_4NHCO_3$, $n-Bu_4NHCO_3$, $Et_3N$, pyridine, lutidine, collidine, diisopropylethylamine, $n-Bu_3N$, $Oct_3N$, N-methylmorpholine, N-ethylmorpholine, N-methylpiperidine, N-ethylpiperidine, N,N-dicyclohexylmethylamine, N,N-dimethylcyclohexylamine, N-methyldibutylamine, N-ethyldicyclohexylamine, N,N-dimethylbutylamine, and N,N-dimethylhexylamine.
23. Method according to any one of the embodiments 16 to 22, wherein the polar protic solvent is MeOH or EtOH.
24. Method according to any one of the embodiments 16 to 23, wherein the compound (III) is

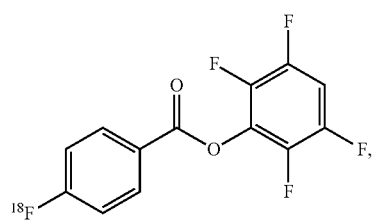

3a

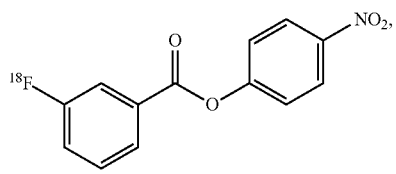

3b

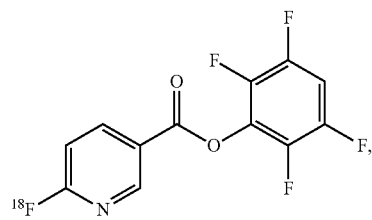

3c

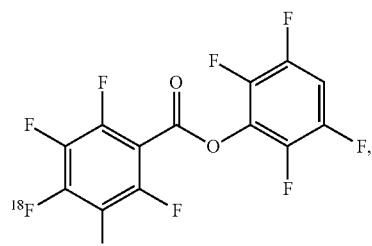

3d

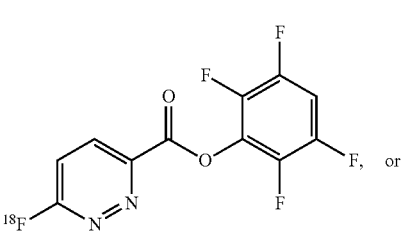

3e

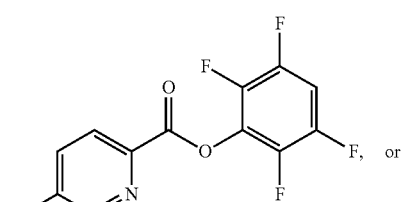

, or

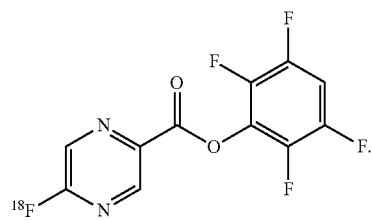

3f

25. Method according to any one of the embodiments 20-24, wherein the [¹⁸F]fluoride is trapped on an anion exchange resin and then eluted directly.

26. Method according to any one of the embodiments 20-24, wherein the $C_3$-$C_6$ alcohol is tBuOH.
27. Method according to any one of the embodiments 16-26, wherein the compound of the formula (I) is selected from the group consisting of compounds 1-3, 1-10, 1-14, 1-17, 1-29, 1-31, 1-32, 1-33, and 1-34:
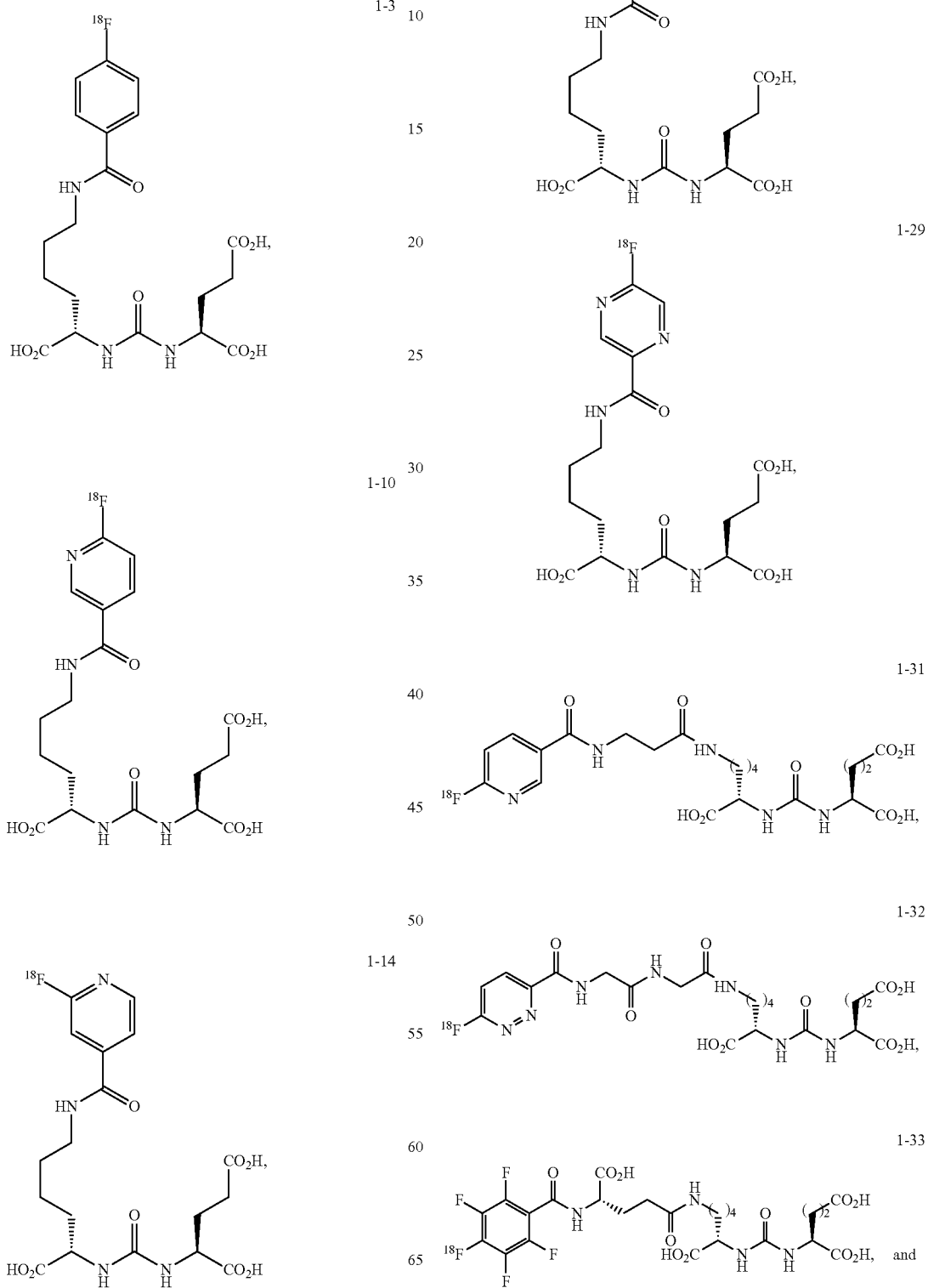

1-34

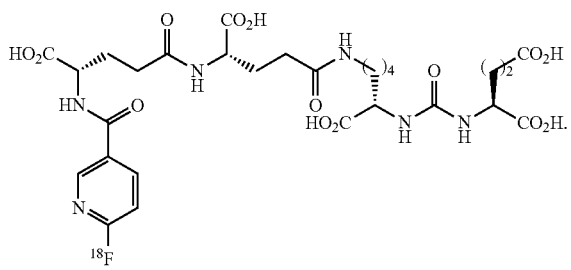

28. Pharmaceutical composition containing at least one compound of formula (I) as defined in embodiment 16 together with at least one pharmaceutically acceptable solvent, ingredient and/or diluent.

29. Pharmaceutical composition according to embodiment 28 for use in imaging prostate cancer cells or prostate cancerous tissue.

The invention claimed is:

1. A compound of formula (II)

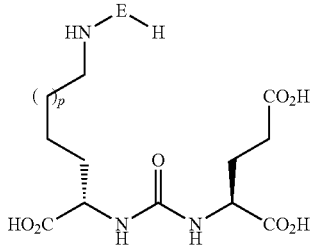
(II)

wherein, E represents a covalent bond or

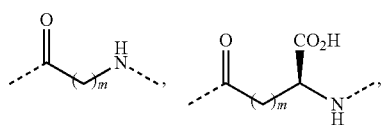

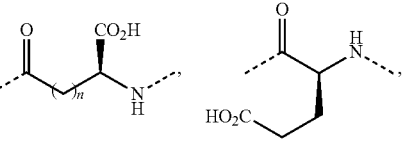

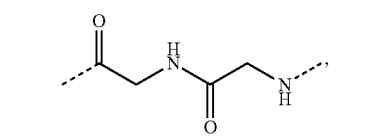

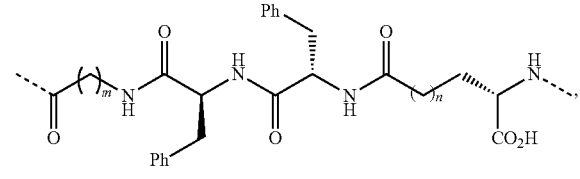

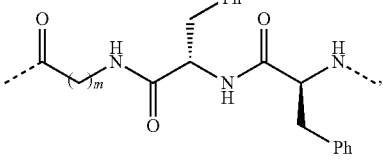

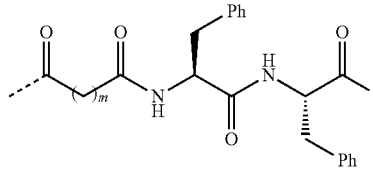

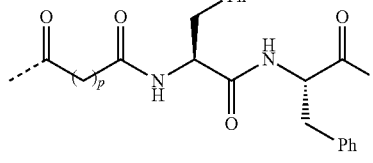

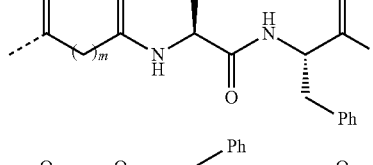

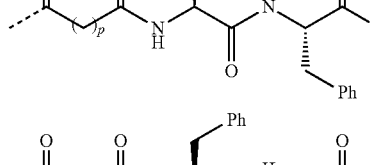

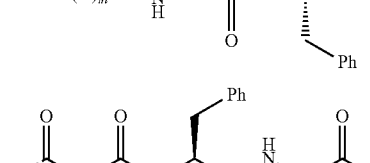

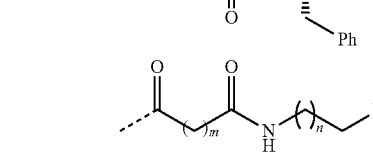

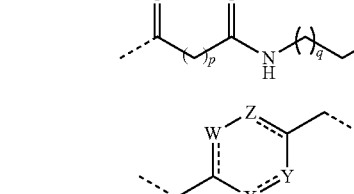

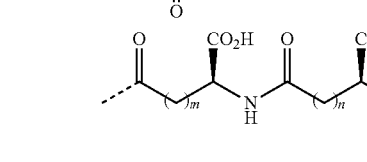

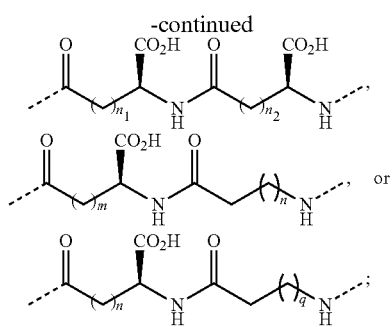

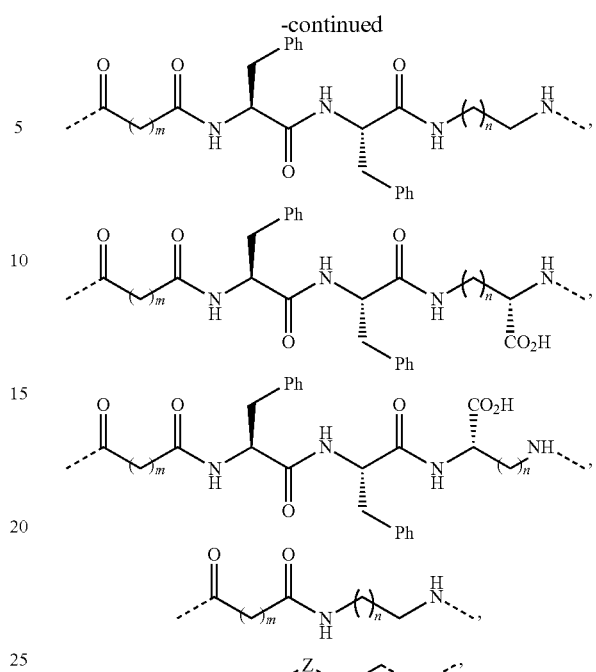

wherein
n is an integer selected from 0 to 10;
$n_1$ is an integer selected from 0 to 10;
$n_2$ is an integer selected from 0 to 10;
m is an integer selected from 1 to 18;
p is an integer selected from 0 to 10;
q is an integer selected from 1 to 18;
X, Y, W, and Z represent independently of each other —$CH_2$—, —CH—, —NH— or —N—;
---- represents a single or double bond;
and diastereomers, entantiomers, hydrates, and salts thereof.

2. A compound of formula (II)

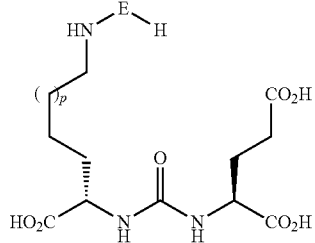
(II)

wherein, E represents a covalent bond or

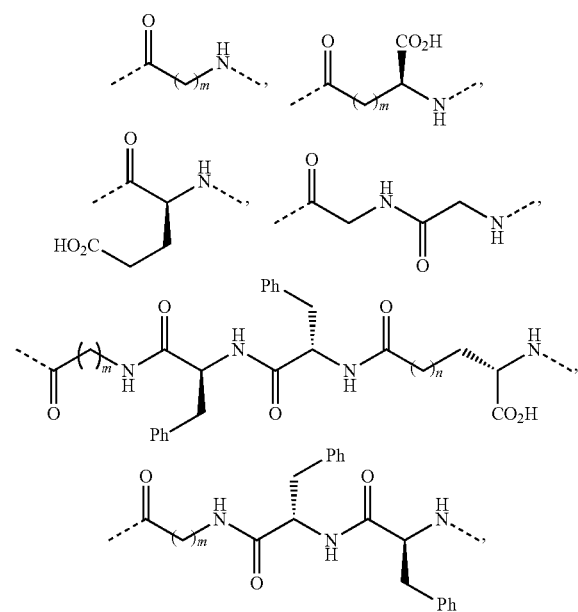

wherein
n is an integer selected from 0 to 10;
m is an integer selected from 1 to 18;
X, Y, W, and Z represent independently of each other —$CH_2$—, —CH—, —NH— or —N—;
---- represents a single or double bond;
and diastereomers, entantiomers, hydrates, and salts thereof.

3. A compound according to claim 1, wherein said compound is a direct precursor of the compound of formula (I)

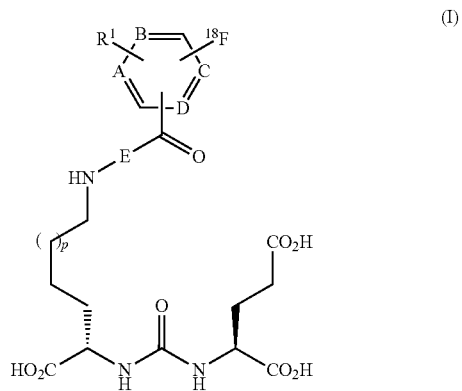
(I)

wherein A, B, C, and D represent independently of each other C—H, C—F, C—Cl, or N; and not more than two of A, B, C, and D represent N;

E represents a covalent bond or

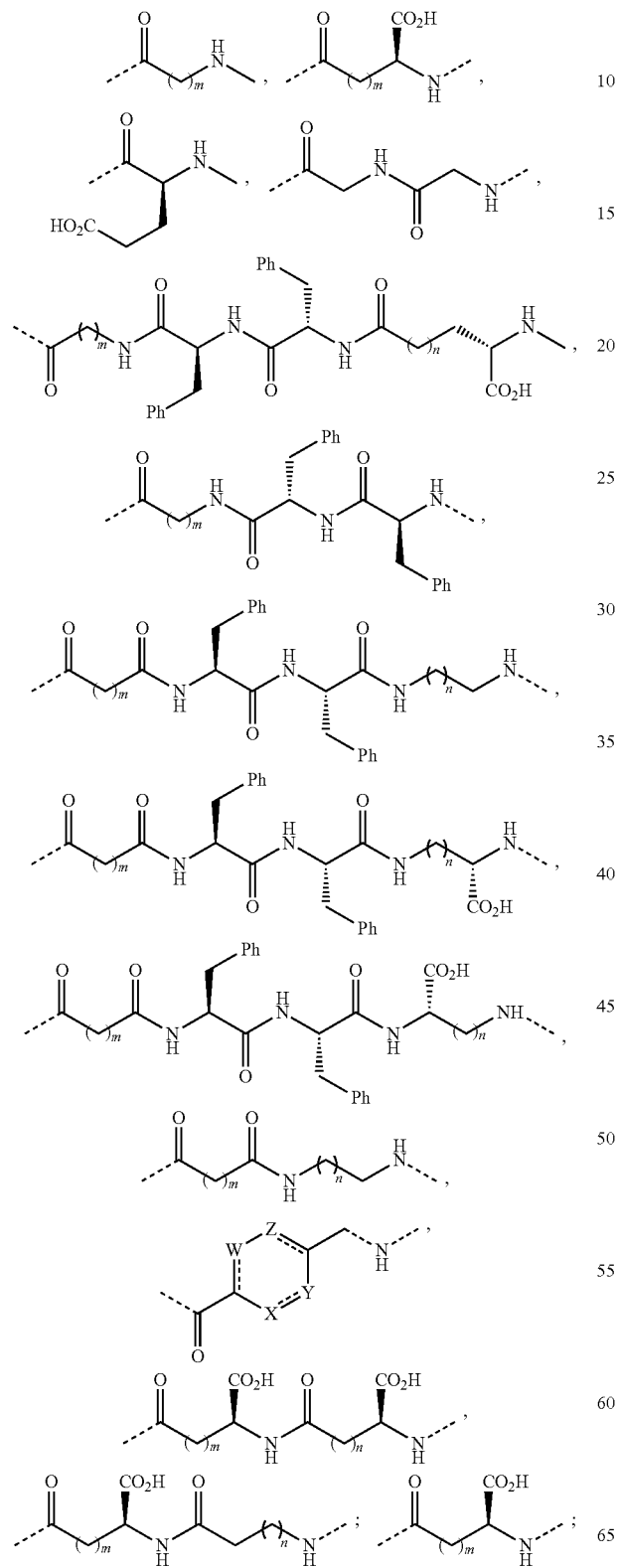

wherein

R$^1$ represents C$_1$-C$_3$ alkyl, C$_1$-C$_3$ alkoxy, C$_1$-C$_3$ haloalkyl, C$_1$-C$_3$ thioalkyl, perfluoralkyl, C$_1$-C$_3$ haloalkoxy, C$_1$-C$_4$ alkylcarbonyl, C$_1$-C$_4$ alkyloxycarbonyl, C$_1$-C$_4$alkylcarboxy, aryloxy, alkylaryl, aryl, arylcarboxy, halogen;

n is an integer selected from 0 to 10;

n$_1$ is an integer selected from 0 to 10;

n$_2$ is an integer selected from 0 to 10;

m is an integer selected from 1 to 18;

p is an integer selected from 0 to 10;

q is an integer selected from 1 to 18;

X, Y, W, and Z represent independently of each other —CH$_2$—, —CH—, —NH—, or —N;

==== represents a single or double bond;

and diastereomers, entantiomers, hydrates, and salts thereof.

4. The compound according to claim 3, wherein the compound is a direct precursor of the compound of formula (I) of claim 3,

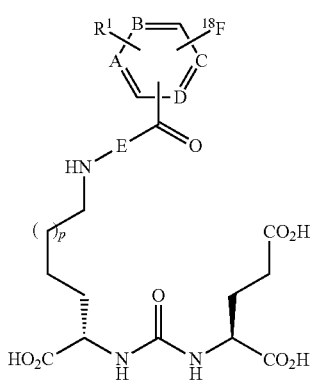

(I)

wherein A, B, C, and D represent independently of each other C—H, C—F or N; and not more than two of A, B, C, and D represent N;

E represents a covalent bond or

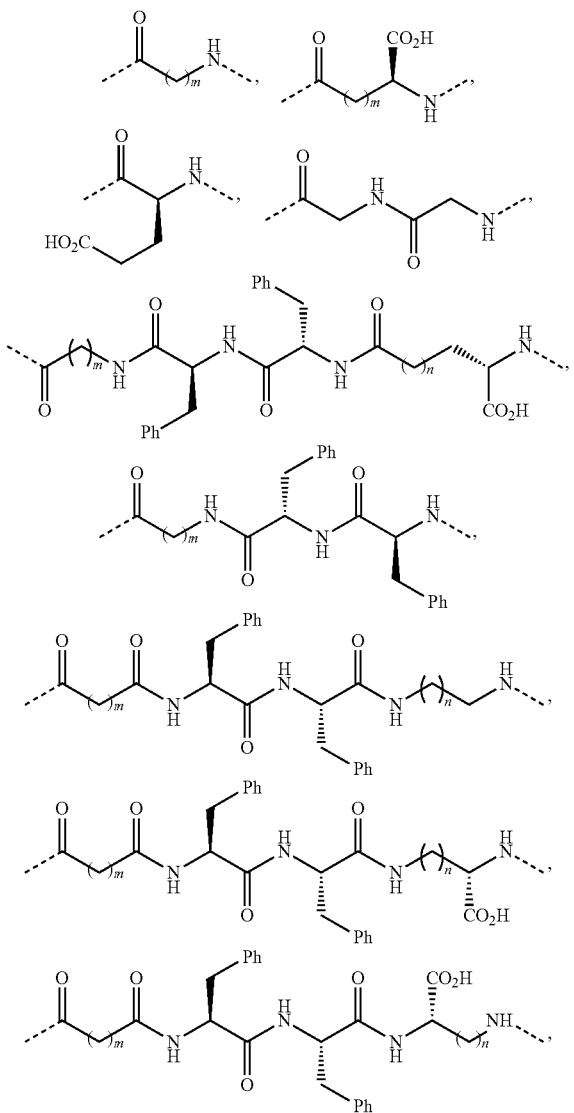

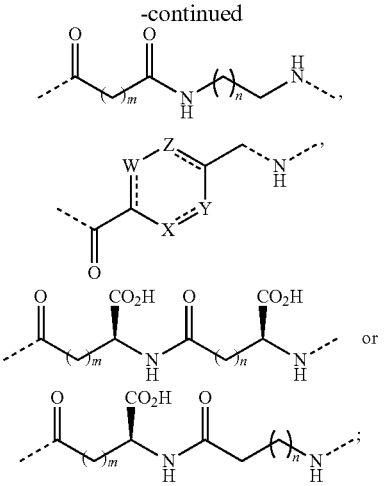

wherein

R¹ represents $C_1$-$C_3$ alkyl, $C_1$-$C_3$ alkoxy, $C_1$-$C_3$ haloalkyl, $C_1$-$C_3$ haloalkoxy, $C_2$-$C_4$ alkylcarbonyl, $C_2$-$C_4$ alkyloxycarbonyl, $C_2$-$C_4$ alkylcarboxy, aryloxy, arylcarboxy, cyano, or nitro;

n is an integer selected from 0 to 10;

m is an integer selected from 1 to 18;

X, Y, W, and Z represent independently of each other —$CH_2$—, —CH—, —NH— or —N—;

═══ represents a single or double bond;

and diastereomers, entantiomers, hydrates, and salts thereof.

5. The compound according to claim 1, wherein either of n or $n_1$ or $n_2$ is an integer selected from 1 to 4.

6. The compound according to claim 1, wherein either of n or $n_1$ or $n_2$ is an integer selected from 1 or 2.

7. The compound according to claim 1, wherein either of m is an integer selected from 1 to 10.

8. The compound according to claim 1, wherein either of m is an integer selected from 1 to 4.

9. The compound according to claim 1, wherein either of p is an integer selected from 0 to 6.

10. The compound according to claim 1, wherein either of p is an integer selected from 0, 2 to 4.

11. The compound according to claim 1, wherein either of q is an integer selected from 1 to 10.

12. The compound according to claim 1, wherein either of q is an integer selected from 1 to 3.

13. A compound according to claim 1 selected from compounds 2a-2p:

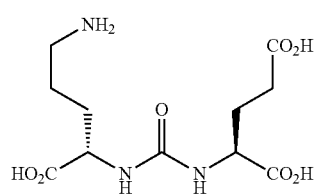

2a

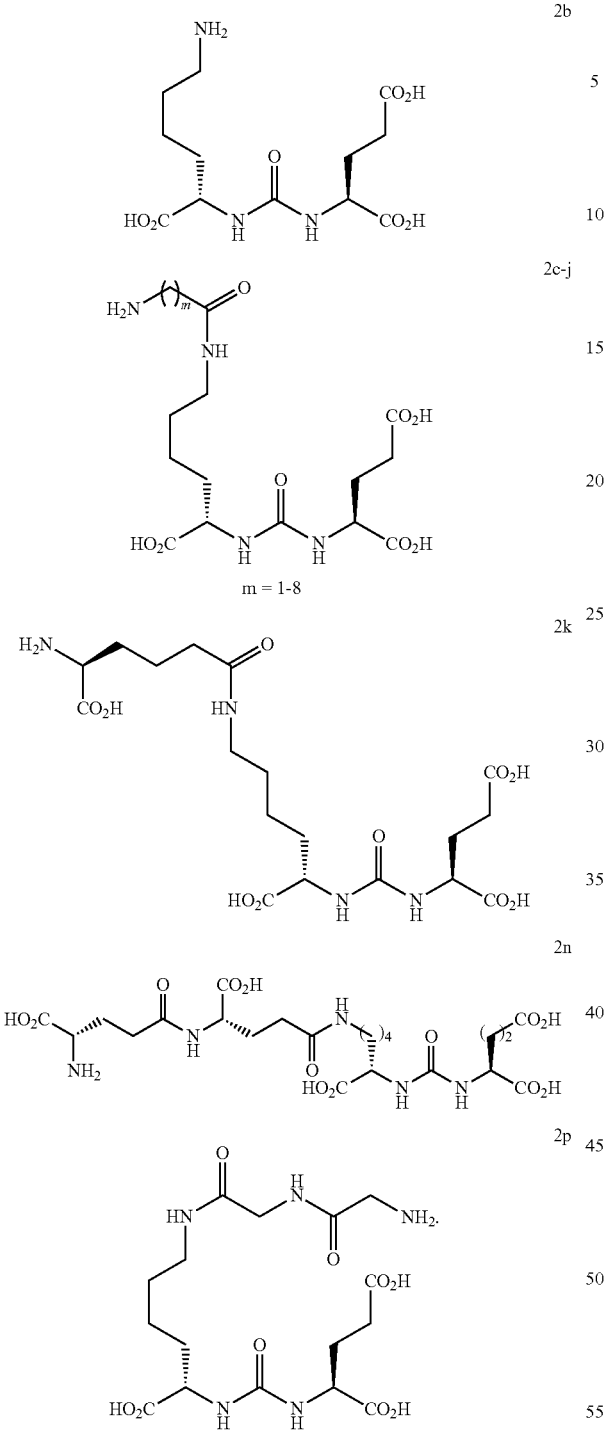

m = 1-8

14. The compound according to claim 1, wherein the salt is selected from acetate, trifluoroacetate, tosylate, mesylate, triflate, chloride, bromide, iodide, sulfate, hydrosulfate, nitrate, perchlorate, lithium, sodium, potassium, cesium, trialkylaryl-, tetraaryl-, tri- and tetralkylammonium salts.

15. A compound according to claim 3, wherein the direct precursor of the compound of formula (I) is capable of being coupled to a compound of formula (II), optionally in an anhydrous protic solvent, wherein formula (III) is

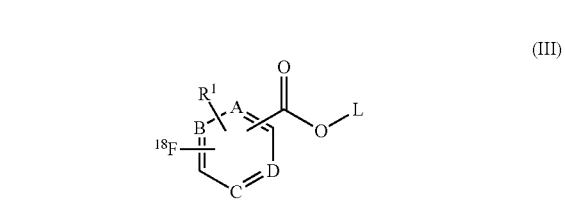

wherein A, B, C, D and $R^1$ have the meanings as defined, and

OL represents a leaving group.

16. A method of preparing a compound (III)

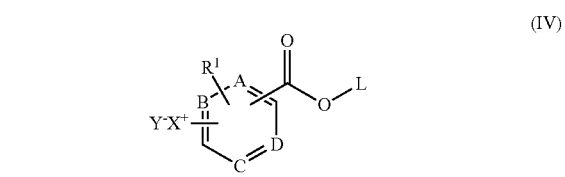

wherein A, B, C, and D represent independently of each other C—H, C—F, C—Cl, or N; and not more than two of A, B, C, and D represent N; and $R^1$ represents $C_1$-$C_3$ alkyl, $C_1$-$C_3$ alkoxy, $C_1$-$C_3$ haloalkyl, —$C_1$-$C_3$ thioalkyl, perfluoralkyl, $C_1$-$C_3$ haloalkoxy, $C_1$-$C_4$ alkylcarbonyl, $C_1$-$C_4$ alkyloxycarbonyl, $C_1$-$C_4$ alkylcarboxy, aryloxy, alkylaryl, aryl, arylcarboxy, halogen; and OL represents a leaving group comprising the following steps (A1)-(A8):

(A1) providing a solution of a compound of the formula (IV) in at least one polar protic solvent or in a solvent mixture containing a polar protic solvent, (IV)

wherein

A, B, C, D, OL and $R^1$ have the same meanings as defined above;

X represents $NR^2_3$, $IR^3$, or $SR^3_2$;

Y represents Br, I, $BF_4$, $O_2CCF_3$, $OSO_2CF_3$, $ClO_4$, $NO_2$, $OSO_2C_6H_4CH_3$, or $OSO_2CH_3$, $R^2$ represents $C_1$-$C_4$ alkyl; and $R^3$ represents aryl;

(A2) providing an aqueous solution of [$^{18}$F]fluoride;

(A3) loading the aqueous solution of [$^{18}$F]fluoride onto an anion exchange resin;

(A4) washing the anion exchange resin with a polar protic solvent or with a polar aprotic solvent;

(A5) flushing of the solvent with air or inert gas flow;

(A6) eluting of [$^{18}$F]fluoride with the solution of the compound of formula (IV) provided in step (A1) and diluting of the resulting solution with an aprotic solvent or with at least one $C_3$-$C_6$ alcohol or with a solvent mixture of at least one $C_3$-$C_6$ alcohol;

or
eluting of [$^{18}$F]fluoride with the solution of the compound of formula (IV) provided in step (A1) concentrating of the resulting solution and redissolving of the residue in an aprotic solvent;
(A7) allowing the compound of formula (IV) to react with [$^{18}$F]fluoride in order to obtain the compound of the formula (III);

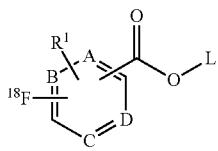
(III)

wherein A, B, C, D, OL and R$^1$ have the same meanings as defined above; and
(A8) purifying of the compound of formula (III).

17. A method for preparing a compound of formula (I) which comprises using a compound of formula (II) as defined in claim 1 in the method:

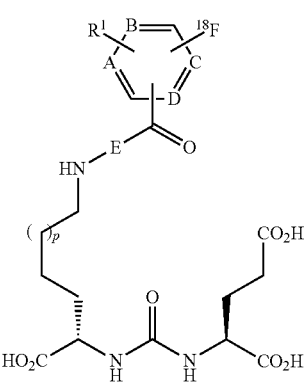
(I)

wherein A, B, C, and D represent independently of each other C—H, C—F, C—Cl, or N; and
not more than two of A, B, C, and D represent N;
E represents a covalent bond or

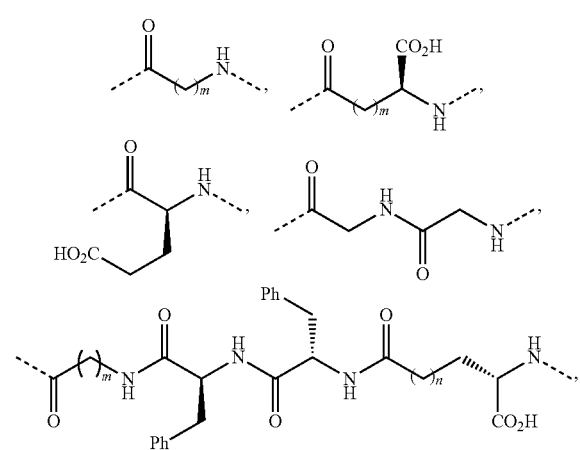

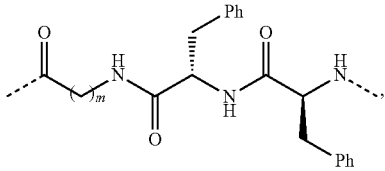

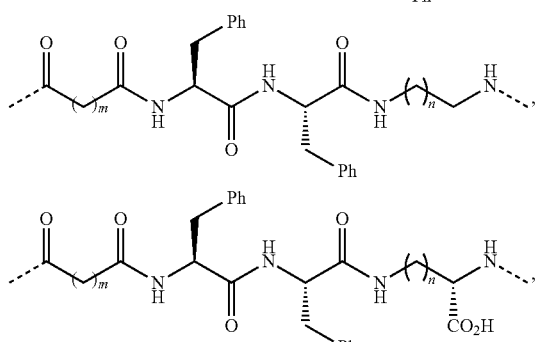

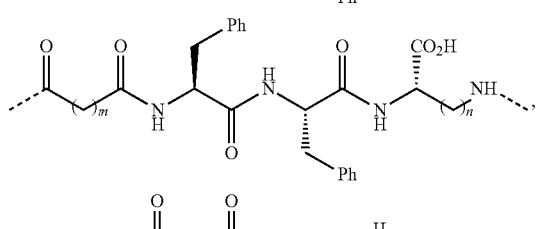

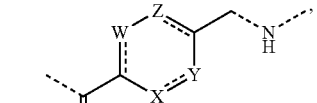

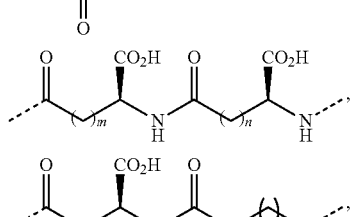

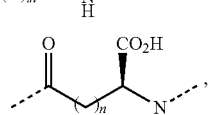

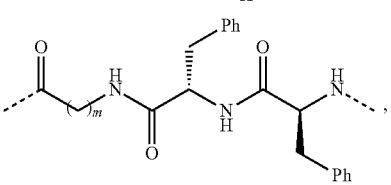

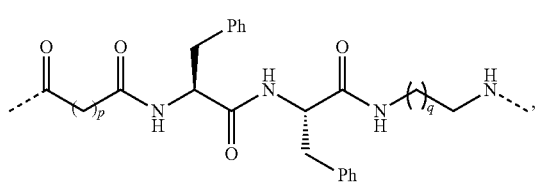

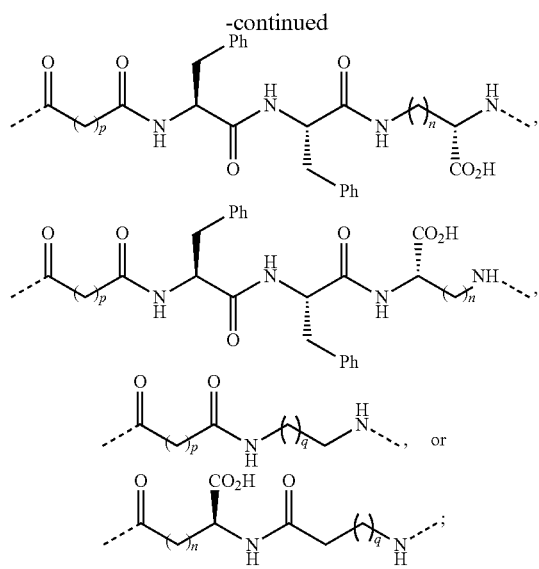

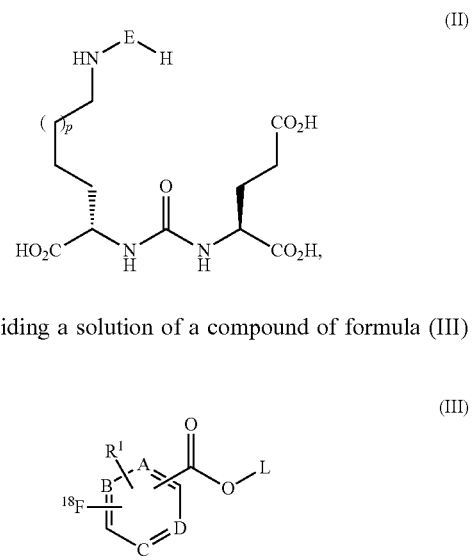

wherein

- $R^1$ represents $C_1$-$C_3$ alkyl, $C_1$-$C_3$ alkoxy, $C_1$-$C_3$ haloalkyl, $C_1$-$C_3$ thioalkyl, perfluoralkyl, $C_1$-$C_3$ haloalkoxy, $C_1$-$C_4$ alkylcarbonyl, $C_1$-$C_4$ alkyloxycarbonyl, $C_1$-$C_4$alkylcarboxy, aryloxy, alkylaryl, aryl, arylcarboxy, halogen;
- n is an integer selected from 0 to 10;
- $n_1$ is an integer selected from 0 to 10;
- $n_2$ is an integer selected from 0 to 10;
- m is an integer selected from 1 to 18;
- p is an integer selected from 0 to 10;
- q is an integer selected from 1 to 18;
- X, Y, W, and Z represent independently of each other —$CH_2$—, —CH—, —NH—, or —N;
- ---- represents a single or double bond;
- and diastereomers, entantiomers, hydrates, and salts thereof.

18. A method for preparing a compound of formula (I) as defined in claim 3,

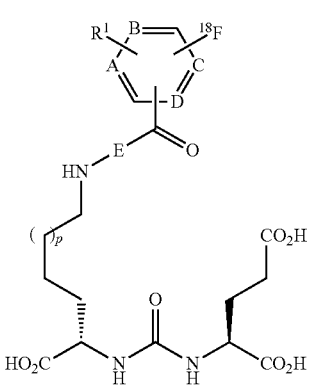

comprising the steps:

(A) providing a solution of a compound of formula (II) in a polar protic solvent or in a solvent mixture containing a polar protic solvent containing at least one base;

(B) providing a solution of a compound of formula (III)

wherein A, B, C, D and $R^1$ have the meanings as defined, and

OL represents a leaving group in a polar protic solvent or in a solvent mixture containing a polar protic solvent;

(C) mixing the solution of the compound of formula (II) and the solution of the compound of formula (III) and allowing the compound of formula (II) to react with the compound of formula (III) in order to obtain the compound of formula (I), (D) purifying the compound of formula (I).

19. Method according to claim 18, wherein step (C) is performed at a reaction temperature T2 which is in the range of 30° C. to 60° C., wherein the reaction time t2 of step (C) is 1-30 min, and wherein the pH value of the reaction solution in step (C) is in the range of 7.0-11.0.

20. Method according to claim 18, wherein the compound of formula (III) does not require purification via HPLC, and/or wherein the method does not comprise the application of a base and any other additives;

and/or wherein the method comprises the application of only onium salt precursor (IV) and [$^{18}$F]fluoride;

and/or wherein the method does not comprise any azeotropic drying steps;

and/or wherein the method does not require any evaporation steps.

21. Method according to claim 18, wherein the compound of formula (I) does not require purification via HPLC, and wherein the method comprises the application of environmentally benign solvents;

and/or wherein the method does not comprise any evaporation steps, and/or wherein the method does not require any deprotection steps, wherein said deprotection steps may be steps of p-methoxybenzyl (PMB) or tBu deprotection using anisol/TFA mixture;

and/or wherein the method does not require a neutralization step;

and/or wherein the method does not require a formulation step, and/or wherein the method does not require toxic solvents.

22. Method according to claim 18 further comprising the following step (E) after the step (D): (E) sterilizing the solution of the compound of formula (I) via sterile filtration.

23. Method according to claim 18 further comprising the following steps (A1)-(A8) after step (A) and before step (B):
(A1) providing a solution of a compound of the formula (IV) in at least one polar protic solvent or in a solvent mixture containing a polar protic solvent,

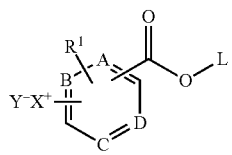

wherein
A, B, C, D, OL and $R^1$ have the same meanings as defined above;
X represents $NR^2_3$, $IR^3$, or $SR^3_2$;
Y represents Br, I, $BF_4$, $O_2CCF_3$, $OSO_2CF_3$, $ClO_4$, $NO_2$, $OSO_2C_6H_4CH_3$, or $OSO_2CH_3$;
$R^2$ represents $C_1$-$C_4$ alkyl; and
$R^3$ represents aryl;
(A2) providing an aqueous solution of [$^{18}$F]fluoride;
(A3) loading the aqueous solution of [$^{18}$F]fluoride onto an anion exchange resin;
(A4) washing the anion exchange resin with a polar protic solvent or with a polar aprotic solvent;
(A5) flushing of the solvent with air or inert gas flow;
(A6) eluting of [$^{18}$F]fluoride with the solution of the compound of formula (IV) provided in step (A1) and diluting of the resulting solution with an aprotic solvent or with at least one $C_3$-$C_6$ alcohol or with a solvent mixture of at least one $C_3$-$C_6$ alcohol;
or
eluting of [$^{18}$F]fluoride with the solution of the compound of formula (IV) provided in step (A1) concentrating of the resulting solution and redissolving of the residue in an aprotic solvent;
(A7) allowing the compound of formula (IV) to react with [$^{18}$F]fluoride in order to obtain the compound of the formula (II);

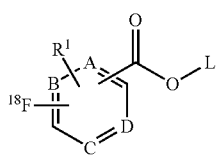

wherein A, B, C, D, OL and $R^1$ have the same meanings as defined above; and
(A8) purifying of the compound of formula (III).

24. Method according to claim 18 further comprising the following step (F) after the step (D) or (E): (F) preparing a pharmaceutical composition containing the solution of the compound of formula (I).

25. Method according to claim 18, wherein the base in step (A) is an organic nitrogen-containing base or a bicarbonate.

26. Method according to claim 25, wherein the organic nitrogen-containing base or the bicarbonate is selected from: $LiHCO_3$, $NaHCO_3$, $KHCO_3$, $CsHCO_3$, $Me_4NHCO_3$, $Me_4NHPO_4$, $Et_4NHCO_3$, $Et_4NHPO_4$, n-$Pr_4NHCO_3$, n-$Pr_4NHPO_4$, i-$Pr_4NHCO_3$, n-$Bu_4NHCO_3$, n-$Bu_4NHPO_4$, $BzlMe_3NHCO_3$, $BzlMe_3NHPO_4$, $BzlEt_3NHCO_3$, $BzlEt_3NHPO_4$, $BzlBu_3NHCO_3$, $BzlBu_3NHPO_4$, $Et_3N$, pyridine, lutidine, collidine, diisopropylethylamine, n-$Pr_3N$, i-$Pr_3N$, n-$Bu_3N$, i-$Bu_3N$, $Oct_3N$, N-methyl-morpholine, N-ethylmorpholine, N-methylpiperidine, N-ethylpiperidine, N,N-dicyclohexylmethylamine N,N-dimethylcyclohexylamine, N-methyl-dibutylamine, N-ethyldicyclohexylamine, N,N-dimethylbutylamine, and N,N-dimethylhexylamine.

27. Method according to claim 18, wherein the polar protic solvent in step A6 is an anhydrous polar protic solvent in methods without evaporation step, or anhydrous MeOH in methods comprising an evaporation step.

28. Method according to claim 18, wherein the [$^{18}$F]fluoride is trapped on an anion exchange resin and then eluted directly.

29. Method according to claim 18, wherein the $C_3$-$C_6$ alcohol is tBuOH, tertAmOH, or pinacol.

30. Method according to claim 18, wherein the compound of the formula (I) is selected from the group consisting of compounds 1-10, 1-14, 1-17, 1-29, 1-31, 1-32, 1-33, and 1-34:

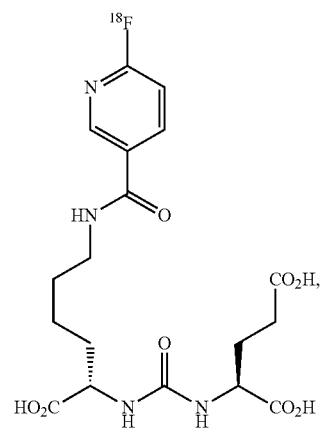

1-10

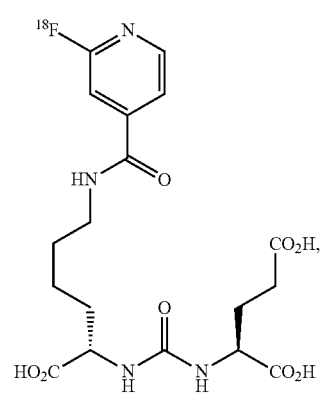

1-14

1-17

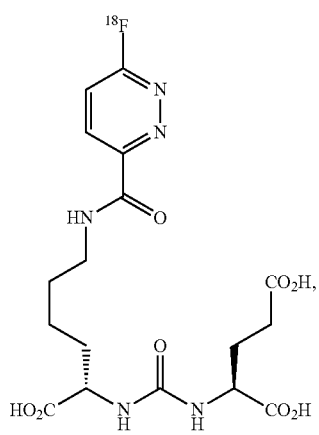

1-29

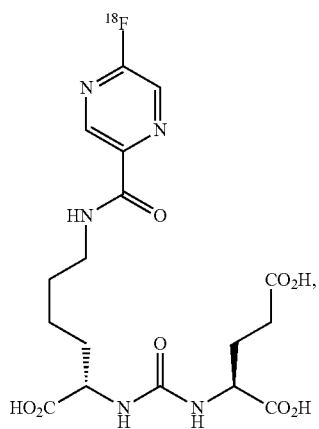

1-31

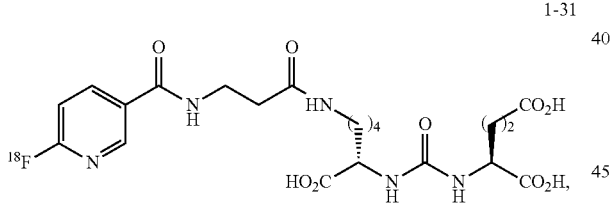

1-32

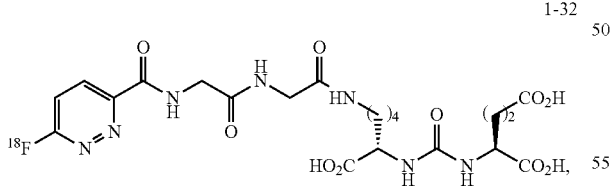

1-33

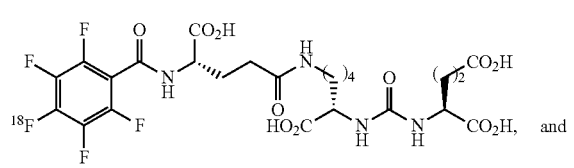

1-34

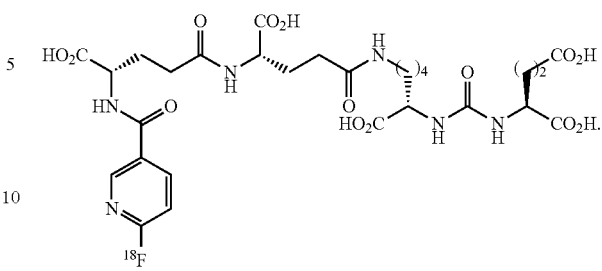

31. A kit for carrying out the method of claim 18 comprising one or more containers containing the compounds of formula (II) and (III), optionally a packaged pharmaceutical compositions comprising a pharmaceutically acceptable carrier, further optionally comprising instructions for preparing compounds according to the invention from supplied precursors and/or instructions for using the composition to image cells or tissues.

32. The method of claim 16, wherein the compound of formula (III) is of formula 3c, 3d, 3e or 3f:

3c

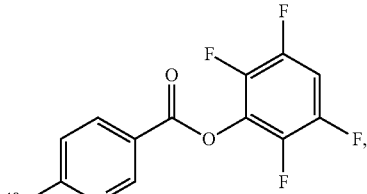

3d

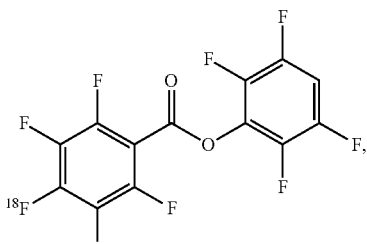

3e

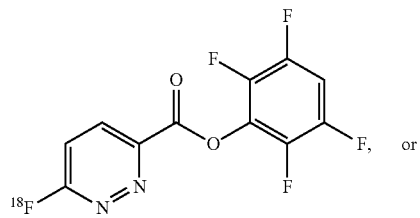

or

3f

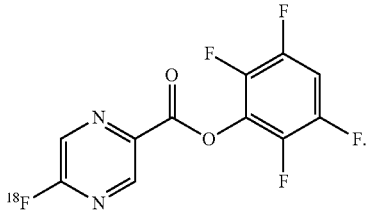

33. The method of claim 18, wherein the compound of formula (III) is of formula 3c, 3d, 3e or 3f:

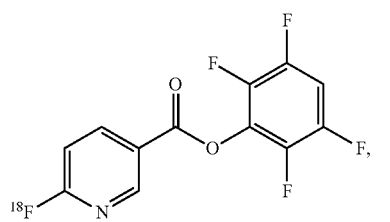
3c
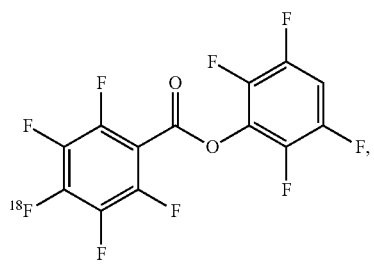
3d
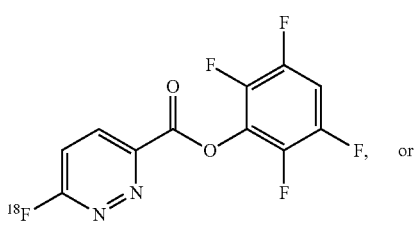
3e or
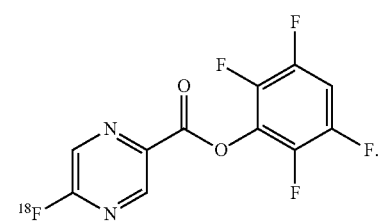
3f
34. The method of claim 15, wherein the compound of formula (III) is of formula 3c, 3d, 3e or 3f:
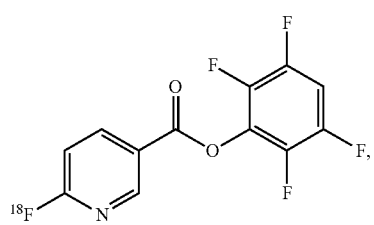
3c
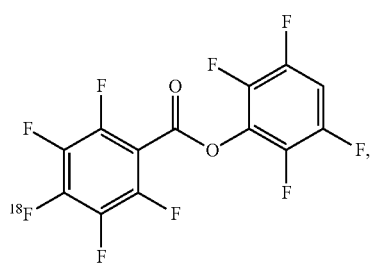
3d
-continued
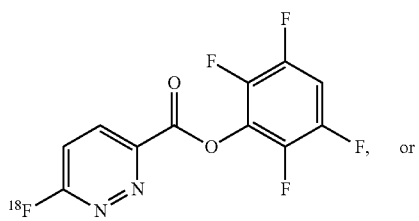
3e or
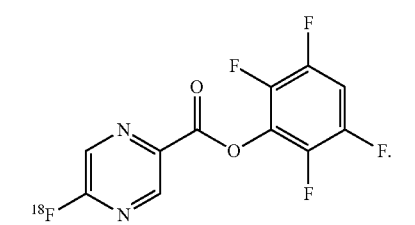
3f
35. The method of claim 15, wherein:
the anhydrous protic solvent is a $C_2$-$C_5$ alcohol;
wherein the residue L of the leaving group OL in formula (III) represents:
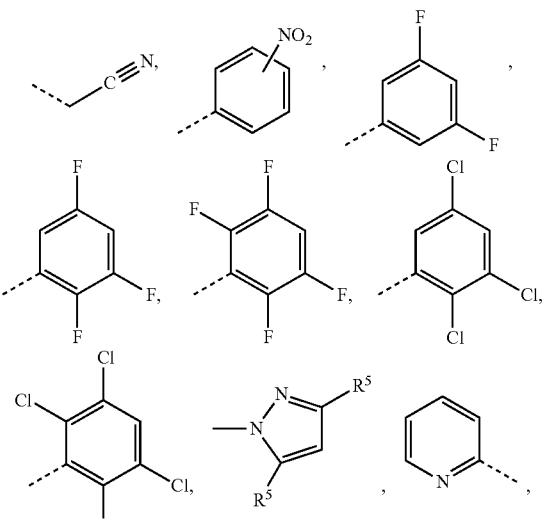
and wherein $R^5$ is selected from methyl, ethyl or n-propyl.
* * * * *

Disclaimer

10,112,974 B2 Max-Planck-Gesellschaft zur Foerderung der Wissenschaften e.V, Munchen, GERMANY; Universitat Zu Koln, Koln, GERMANY; Bernd NEUMAIER, Hurth, GERMANY; Boris ZLATOPOLSKIY, Koln, GERMANY; Rapheal RICHARZ, Leverkusen, GERMANY; Phillip KRAPF, Much, GERMANY. METHOD FOR THE PRODUCTION OF !SF-LABELED ACTIVE ESTERS AND THEIR APPLICATION EXEMPLIFIED BY THE PREPARATION OF A PSMA-SPECFIC PET-TRACER. Patent dated October 30, 2018. Disclaimer filed March 13, 2020 by the assignee, Max-Planck-Gesellschaft Zur Foerdefung Der Wissenschaften E.V. and Universotat Zu Kolo.

I hereby disclaim the claims 1-5, 7, 9, 13-15 and 31.

*(Official Gazette, July 13, 202l)*